US012735480B2

(12) United States Patent
Yin et al.

(10) Patent No.: US 12,735,480 B2
(45) Date of Patent: Sep. 15, 2026

(54) ANTI-CD47/ANTI-LAG-3 BISPECIFIC ANTIBODY, PREPARATION METHOD THEREFOR AND USE THEREOF

(71) Applicant: NANJING GENSCRIPT BIOTECH CO., LTD., Nanjing (CN)

(72) Inventors: Liusong Yin, Jiangsu (CN); Zhongdao Li, Jiangsu (CN); Tielin Zhou, Jiangsu (CN); Zhuo Fang, Jiangsu (CN)

(73) Assignee: Nanjing GenScript Biotech Co., Ltd., Nanjing (CN)

( * ) Notice: Subject to any disclaimer, the term of this patent is extended or adjusted under 35 U.S.C. 154(b) by 1272 days.

(21) Appl. No.: 17/628,614

(22) PCT Filed: Jul. 23, 2020

(86) PCT No.: PCT/CN2020/103744
§ 371 (c)(1),
(2) Date: Jan. 20, 2022

(87) PCT Pub. No.: WO2021/013215
PCT Pub. Date: Jan. 28, 2021

(65) Prior Publication Data

US 2022/0267436 A1 Aug. 25, 2022

(30) Foreign Application Priority Data

Jul. 23, 2019 (CN) ......................... 201910665603.6

(51) Int. Cl.
*A61P 35/00* (2006.01)
*C07K 16/28* (2006.01)

(52) U.S. Cl.
CPC .......... *C07K 16/2803* (2013.01); *A61P 35/00* (2018.01); *C07K 2317/31* (2013.01); (Continued)

(58) Field of Classification Search
None
See application file for complete search history.

(56) References Cited

U.S. PATENT DOCUMENTS 5,795,572 A 8/1998 Diegel et al.

FOREIGN PATENT DOCUMENTS

CN 103665165 A 3/2014
CN 107614013 A 1/2018
CN 109475617 A 3/2019
CN 109476762 A 3/2019
WO WO-2016024021 A1 * 2/2016 .............. A61P 35/00

(Continued)

OTHER PUBLICATIONS

Hoey RJ, Eom H, Horn JR. Structure and development of single domain antibodies as modules for therapeutics and diagnostics. Exp Biol Med (Maywood). 2019;244(17):1568-1576. (Year: 2019).*

(Continued)

*Primary Examiner* — Joanne Hama
*Assistant Examiner* — Hannah Sunshine
(74) *Attorney, Agent, or Firm* — Yong Chen; Lin Sun-Hoffman; Liu Chen & Hoffman LLP

(57) ABSTRACT

Disclosed are an anti-CD47/anti-LAG-3 bispecific antibody, a preparation method thereof and a use thereof. The bispecific antibody comprises (a) a first antigen binding portion, which comprises a heavy chain variable region ($V_H$) and a light chain variable region ($V_L$), wherein $V_H$ and $V_L$ form an antigen binding site for specifically binding to CD47; and (b) a second antigen binding portion, which comprises a single-domain antibody (sdAb) for specifically binding to LAG-3, wherein the first antigen binding portion and the second antigen binding portion fuse with each other. The bispecific antibody can simultaneously block two modes of tumor immune escape, thus providing a better effect in tumor immunotherapy.

16 Claims, 3 Drawing Sheets

Specification includes a Sequence Listing.

| | LAG3-E-HC | LAG3-G9-HC | LAG3-G15-HC | LAG3-E-HN | LAG3-G9-HN |
|---|---|---|---|---|---|
| EC50 | 0.8003 | 0.6018 | 0.6724 | 0.5258 | 0.4767 |

| | LAG3-G15-HN | Human IgG | sdab-LAG3-IgG4PE | Anti-CD47 antibody |
|---|---|---|---|---|
| EC50 | 0.5696 | 2.462 | 0.04034 | 4.929e+013 |

(52) U.S. Cl.
CPC .... *C07K 2317/53* (2013.01); *C07K 2317/565* (2013.01); *C07K 2317/569* (2013.01); *C07K 2317/92* (2013.01)

(56) References Cited

FOREIGN PATENT DOCUMENTS

| | | | | |
|---|---|---|---|---|
| WO | 2019094574 | A1 | 5/2019 | |
| WO | 2019/134710 | A1 | 7/2019 | |
| WO | WO-2019144895 | A1 * | 8/2019 | ......... C07K 16/2803 |
| WO | WO-2019185040 | A1 * | 10/2019 | ......... C07K 16/2803 |

OTHER PUBLICATIONS

Madsen AV, Kristensen P, Buell AK, Goletz S. Generation of robust bispecific antibodies through fusion of single-domain antibodies on IgG scaffolds: a comprehensive comparison of formats. MAbs. 2023;15(1):2189432. (Year: 2023).*

Kolfschoten, Marjin van der Neut, et al. Anti-Inflammatory Activity of Human IgG4 Antibodies by Dynamic Fab Arm Exchange, Science 317, 1554, 2007.

Labrijn, Aran F., et al. Bispecific Antibodies: a mechanistic review of the pipeline, Nature Reviews, Drug Discovery, vol. 18, Aug. 2019, p. 585-608.

Dickopf, Steffen, "Format and Geometries matter: Structure-based design defines the functionality of bispecific antibodies", Computational and Structural Biotechnology Journal 18 (2020) 1221-1227.

European Application No. 20843206.2, Extended Search Report dated Oct. 16, 2023.

Applicant: Nanjing Genscript Biotech Co., LTD; International Application No. PCT/CN2020/103744 filed: Jul. 23, 2020; International Search Report and Written Opinion; dated Oct. 28, 2020; 16 pgs.

* cited by examiner

| | LAG3-E-HC | LAG3-G9-HC | LAG3-G15-HC | LAG3-E-HN | LAG3-G9-HN |
|---|---|---|---|---|---|
| EC50 | 0.8003 | 0.6018 | 0.6724 | 0.5258 | 0.4767 |

| | LAG3-G15-HN | Human IgG | sdab-LAG3-IgG4PE | Anti-CD47 antibody |
|---|---|---|---|---|
| EC50 | 0.5696 | 2.462 | 0.04034 | 4.929e+013 |

| | LAG3-E-LC | LAG3-E-LN | LAG3-G9-LN | LAG3-G15-LN |
|---|---|---|---|---|
| EC50 | 0.5521 | 0.4475 | 0.3215 | 0.5352 |

| | sdab-LAG3-IgG4PE | Anti-CD47 antibody | Human IgG |
|---|---|---|---|
| EC50 | 0.04034 | 4.929e+013 | 2.462 |

| | LAG3-E-HC | LAG3-G9-HC | LAG3-G15-HC | LAG3-E-HN | LAG3-G9-HN |
|---|---|---|---|---|---|
| EC50 | 1.169 | 0.8645 | 0.9112 | 4.438 | 3.964 |

| | LAG3-G15-HN | Human IgG | sdab-LAG3-IgG4PE | Anti-CD47 antibody |
|---|---|---|---|---|
| EC50 | 3.853 | ~ 14.44 | | 1.006 |

| | LAG3-E-LC | LAG3-E-LN | LAG3-G9-LN | LAG3-G15-LN |
|---|---|---|---|---|
| EC50 | 1.204 | ~ 4.072 | 2.511 | 3.383 |

| | sdab-LAG3-IgG4PE | Anti-CD47 antibody | Human IgG |
|---|---|---|---|
| EC50 | | 1.006 | ~ 14.44 |

| | LAG-3 mAb(25F7) | LAG-3-G9-HC | LAG-3-E-HC | LAG-3-E-LC |
|---|---|---|---|---|
| EC50 | 0.5047 | 0.02346 | 0.08673 | 0.05326 |

| | Anti-CD47 antibody | LAG3-G9-HC |
|---|---|---|
| EC50 | ~ 0.3681 | 0.06201 |

ANTI-CD47/ANTI-LAG-3 BISPECIFIC ANTIBODY, PREPARATION METHOD THEREFOR AND USE THEREOF

TECHNICAL FIELD

The present invention relates to the field of antibodies, and specifically, to a bispecific antibody, a preparation method thereof, and use thereof. The bispecific antibody includes a first antigen binding portion that specifically binds to CD47 and a second antigen binding portion that specifically binds to LAG-3.

BACKGROUND

The mammalian immune system is a host defense system that protects a mammal from microbial infections and cancers (Chen et al., Frontiers Immunol. 9:320 (2018)). The immune system all over the body is an extremely complex network system. Different immune cells and specific tissues and organs exert a synergistic effect to form the immune system. When the immune system is functioning normally, diseased cells in the host body will be recognized from healthy cells and eliminated, thereby ensuring the stability of the body's environment. Therefore, maintaining the integrity of the immune system is essential to maintaining our own health. Conversely, loss of control of the immune system will cause autoimmune diseases, inflammation, cancers, etc (Ribas et al., Cancer Discovery 5:915-9 (2015); Yao and Chen, Eur. J. Immunol. 43:576-9 (2013)). The immune system can be divided into two categories, namely humoral immunity and cell-mediated immunity. Antibodies and other biological macromolecules regulate humoral immunity. In contrast, cell-mediated immunity is regulated at the cellular level, involving the activation of macrophages, natural killer cells, and antigen-specific killer T cells.

Activation and suppression of immune response are mainly regulated by two independent signaling pathways (Gorentla and Zhong, J. Clin. Cell. Immunol. (2012); Huse, J. Cell Sci. 122:1269-73 (2009); Mizota et al., J. Anesthesia 27:80-7 (2013)). The first signal is antigen-mediated. The first signal is generated when the T-cell receptor specifically recognizes and binds to the antigen peptide presented by the MHC on the surface of the antigen-presenting cell (APC). The second signal is provided by the interaction between the APCs and costimulators expressed on the surface of T cells. T cells can kill tumors only when the first and second signals are activated in turn. If the second signal is lacking, T cells will enter a state of unresponsiveness or will be immune tolerance, and even cause programmed cell death.

As described above, the second signaling pathway is very important to the activation of immune cells. Specifically, co-stimulatory and co-inhibitory receptors participate in the second signaling pathway to perform immune response and regulation on antigen-receptor presentation and balance positive and negative signals while maintaining immune tolerance to autoantigens, maximizing the immune response to invaders (Chen and Flies, Nat. Rev. Immunol. 13:227-42 (2013); Ewing et al., Int. J. Cardiol. 168:1965-74 (2013); Liu et al., Immunol. Invest. 45:813-31 (2016); Shen et al., Frontiers in Biosci. 24:96-132 (2019); Zhang and Vignali, Immunity 44:1034-51 (2016)).

Lymphocyte-activation gene 3 (LAG-3) is a transmembrane protein, which is expressed on activated T cells, natural killer cells, B cells, and plasmacytoid dendritic cells. LAG-3 is one of the immune checkpoint receptors on APC that bind to MHC II and negatively regulate T cell receptor signaling. In recent years, fibrinogen-like protein 1 FGL1, a liver-secreted protein, is identified as another LAG-3 functional ligand. Because LAG-3 is also expressed on Treg cells, blocking LAG-3 can inhibit the activity of Treg cells and enhance the anti-tumor immune function.

CD47, also known as integrin associated protein, is a transmembrane protein that is encoded by the CD47 gene, and belongs to the immunoglobulin superfamily CD47 is widely expressed on the surface of normal cells and can interact with signal-regulatory protein alpha (SIRPα), thrombospondin-1 (TSP-1), and integrin to mediate cell apoptosis, proliferation, and immunity responses, and the like. CD47, as an innate immune checkpoint receptor, binds to SIRPα mainly expressed on macrophages and dendritic cells and then releases a "don't eat me" signal to the macrophages to inhibit phagocytosis, thereby avoiding the attack of the body's immune system. Cancer cells escape phagocytosis by upregulating the expression of CD47, thereby evading immune surveillance. The overexpression of CD47 in blood and solid tumors is highly correlated with the poor prognosis of clinical treatment. Therefore, the use of anti-CD47 antibodies or high-affinity SIRPα variants to block the CD47-SIRPα signaling pathway has become a potential strategy to promote the phagocytosis of tumor cells by macrophages. However, in view of the wide expression of CD47, the anti-CD47 antibodies have a high risk of binding to healthy cells, especially red blood cells, which will increase the risk of blood toxicity. In addition, more and more studies have shown that blocking CD47 alone is not sufficient to generate anti-tumor immunity in immunocompetent hosts. Moreover, researchers at Stanford University reported that the interference in the CD47/SIRPα pathway by SIRPα treatment cannot induce phagocytosis (Sockolosky et al., PNAS 113:E2646-2654 (2016)). Therefore, considering the effectiveness and safety of cancer treatment, the anti-CD47 antibodies need to be further optimized to improve tumor targeting specificity.

SUMMARY

According to an aspect, the present invention provides an isolated bispecific binding protein, and the protein includes a first antigen binding portion that specifically binds to CD47 and a second antigen binding portion that specifically binds to LAG-3. Specifically, the present invention provides an isolated anti-CD47/anti-LAG-3 bispecific antigen-binding protein or a fragment thereof, including (a) a first antigen binding portion including a heavy chain variable region ($V_H$) and a light chain variable region ($V_L$), $V_H$ and $V_L$ forming an antigen binding site that specifically binds to CD47; and (b) a second antigen binding portion including a single-domain antibody (sdAb) that specifically binds to LAG-3, where the first antigen binding portion and the second antigen binding portion are fused to each other.

In some embodiments, the $V_H$ of the first antigen binding portion includes heavy chain complementarity-determining regions (CDRs) HCDR1, HCDR2, and HCDR3, and the amino acid sequences of the HCDR1, HCDR2, and HCDR3 are respectively as set forth in SEQ ID NO:33, SEQ ID NO:34, and SEQ ID NO:35, or the sequences respectively including at most three (three, two, or one) amino acid mutations thereto; and the $V_L$ of the first antigen binding portion includes light chain CDRs LCDR1, LCDR2, and LCDR3, amino acid sequences of the LCDR1, LCDR2, and LCDR3 are respectively as set forth in SEQ ID NO:36, SEQ ID NO:37, and SEQ ID NO:38, or the sequences respectively including at most three (three, two, or one) amino acid mutations thereto. In some embodiments, the $V_H$ of the first antigen binding portion includes heavy chain CDRs HCDR1, HCDR2, and HCDR3, amino acid sequences of the HCDR1, HCDR2, and HCDR3 are respectively as set forth in SEQ ID NO:33, SEQ ID NO:34, and SEQ ID NO:35, or the sequences respectively including at most three (three, two, or one) amino acid substitutions thereto; and the $V_L$ of the first antigen binding portion includes light chain CDRs LCDR1, LCDR2, and LCDR3, amino acid sequences of the LCDR1, LCDR2, and LCDR3 are respectively as set forth in SEQ ID NO:36, SEQ ID NO:37, and SEQ ID NO:38, or the sequences respectively including at most three (three, two, or one) amino acid substitutions thereto. In some embodiments, the $V_H$ of the first antigen binding portion includes heavy chain CDRs HCDR1, HCDR2, and HCDR3, and amino acid sequences of the HCDR1, HCDR2, and HCDR3 are respectively as set forth in SEQ ID NO:33, SEQ ID NO:34, and SEQ ID NO:35; and the $V_L$ of the first antigen binding portion includes light chain CDRs LCDR1, LCDR2, and LCDR3, and amino acid sequences of the LCDR1, LCDR2, and LCDR3 are respectively as set forth in SEQ ID NO:36, SEQ ID NO:37, and SEQ ID NO:38.

In some embodiments, sdAb of the second antigen binding portion includes CDRs CDR1, CDR2, and CDR3, amino acid sequences of the CDRs CDR1, CDR2, and CDR3 are respectively as set forth in SEQ ID NO:41, SEQ ID NO:42, and SEQ ID NO:43, or the sequences respectively including at most three (three, two, or one) amino acid mutations thereto. In some embodiments, sdAb of the second antigen binding portion includes CDRs CDR1, CDR2, and CDR3, amino acid sequences of the CDRs CDR1, CDR2, and CDR3 are respectively as set forth in SEQ ID NO:41, SEQ ID NO:42, and SEQ ID NO:43, or the sequences respectively including at most three (three, two, or one) amino acid substitutions thereto. In some specific embodiments, sdAb of the second antigen binding portion includes CDRs CDR1, CDR2, and CDR3, and amino acid sequences of the CDRs CDR1, CDR2, and CDR3 are respectively as set forth in SEQ ID NO:41, SEQ ID NO:42, and SEQ ID NO:43.

In some embodiments, the first antigen binding portion is a full-length antibody including two heavy chains and two light chains, the heavy chain includes $V_H$, and the light chain includes $V_L$.

In some embodiments, the first antigen binding portion and the second antigen binding portion are fused. In some embodiments, the C-terminus of the second antigen binding portion is fused to the N-terminus of at least one heavy chain of the first antigen binding portion or the N-terminus of at least one light chain of the first antigen binding portion. In some embodiments, the N-terminus of the second antigen binding portion is fused to the C-terminus of at least one heavy chain of the first antigen binding portion or the C-terminus of at least one light chain of the first antigen binding portion.

In some embodiments, the first antigen binding portion and the second antigen binding portion are fused by a peptide bond or a peptide linker. In some embodiments, the peptide linker is selected from a mutated human IgG1 hinge region or a GS linker. In some preferred embodiments, an amino acid sequence of the peptide linker is as set forth in SEQ ID NO:45, SEQ ID NO:47, or SEQ ID NO:49.

In some embodiments, the heavy chain of the first antigen binding portion includes a sequence that is at least 80%, 85%, 90%, 95%, 96%, 97%, 98%, or 99% identical to the amino acid sequence as set forth in SEQ ID NO:4, and the light chain of the first antigen binding portion includes a sequence that is at least 80%, 85%, 90%, 95%, 96%, 97%, 98%, or 99% identical to the amino acid sequence as set forth in SEQ ID NO:6. In some embodiments, the heavy chain of the first antigen binding portion includes a sequence that is at least 95% identical to the amino acid sequence as set forth in SEQ ID NO:4, and the light chain of the first antigen binding portion includes a sequence that is at least 95% identical to the amino acid sequence as set forth in SEQ ID NO:6. In some specific embodiments, the heavy chain of the first antigen binding portion includes the amino acid sequence as set forth in SEQ ID NO:4, and the light chain of the first antigen binding portion includes the amino acid sequence as set forth in SEQ ID NO:6.

In some embodiments, the second antigen binding portion includes a sequence that is at least 80%, 85%, 90%, 95%, 96%, 97%, 98%, or 99% identical to the amino acid sequence as set forth in SEQ ID NO:40. In some embodiments, the second antigen binding portion includes a sequence that is at least 95% identical to the amino acid sequence as set forth in SEQ ID NO:40. In some specific embodiments, the second antigen binding portion includes the amino acid sequence as set forth in SEQ ID NO:40.

In some embodiments, an isolated anti-CD47/anti-LAG-3 bispecific antigen-binding protein or a fragment thereof is provided, the heavy chain of the first antigen binding portion includes a sequence that is at least 80%, 85%, 90%, 95%, 96%, 97%, 98%, or 99% identical to the amino acid sequence as set forth in SEQ ID NO:4, and the light chain of the first antigen binding portion includes a sequence that is at least 80%, 85%, 90%, 95%, 96%, 97%, 98%, or 99% identical to the amino acid sequence as set forth in SEQ ID NO:6; and the second antigen binding portion includes a sequence that is at least 80%, 85%, 90%, 95%, 96%, 97%, 98%, or 99% identical to the amino acid sequence as set forth in SEQ ID NO:40. In some embodiments, an isolated anti-CD47/anti-LAG-3 bispecific antigen-binding protein or a fragment thereof is provided, the heavy chain of the first antigen binding portion includes a sequence that is at least 95% identical to the amino acid sequence as set forth in SEQ ID NO:4, and the light chain of the first antigen binding portion includes a sequence that is at least 95% identical to the amino acid sequence as set forth in SEQ ID NO:6; and the second antigen binding portion includes a sequence that is at least 95% identical to the amino acid sequence as set forth in SEQ ID NO:40. In some embodiments, an isolated anti-CD47/anti-LAG-3 bispecific antigen-binding protein or a fragment thereof is provided; the heavy chain of the first antigen binding portion includes the amino acid sequence as set forth in SEQ ID NO:4, and the light chain of the first antigen binding portion includes the amino acid sequence as set forth in SEQ ID NO:6; and the second antigen binding portion includes the amino acid sequence as set forth in SEQ ID NO:40.

In some embodiments, the first antigen binding portion includes a human, humanized, or chimeric antibody or a fragment thereof. In some embodiments, the second antigen binding portion includes sdAb that specifically binds to LAG-3, and the sdAb is a camelid, chimeric, humanized, or human antibody.

In some embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two heavy chains of the anti-CD47 antibody, wherein the heavy chain fusion polypeptide includes a sequence that is at least 80%, 85%, 90%, 95%, 96%, 97%, 98%, or 99% identical to the amino acid sequence as set forth in SEQ ID NO:8, SEQ ID NO:12, or SEQ ID NO:24, and the light chain polypeptide includes a sequence that is at least 80%, 85%, 90%, 95%, 96%, 97%, 98%, or 99% identical to the amino acid sequence as set forth in SEQ ID NO:6. In some embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two heavy chains of the anti-CD47 antibody, wherein the heavy chain fusion polypeptide includes a sequence that is at least 95% identical to the amino acid sequence as set forth in SEQ ID NO:8, SEQ ID NO:12, or SEQ ID NO:24, and the light chain polypeptide includes a sequence that is at least 95% identical to the amino acid sequence as set forth in SEQ ID NO:6. In some specific embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two heavy chains of the anti-CD47 antibody, wherein the heavy chain fusion polypeptide includes the amino acid sequence as set forth in SEQ ID NO:8, SEQ ID NO:12, or SEQ ID NO:24, and the light chain polypeptide includes the amino acid sequence as set forth in SEQ ID NO:6. In some other specific embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two heavy chains of the anti-CD47 antibody, wherein the heavy chain fusion polypeptide includes the amino acid sequence as set forth in SEQ ID NO: 8, and the light chain polypeptide includes the amino acid sequence as set forth in SEQ ID NO:6. In some specific embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two heavy chains of the anti-CD47 antibody, wherein the heavy chain fusion polypeptide includes the amino acid sequence as set forth in SEQ ID NO:12, and the light chain polypeptide includes the amino acid sequence as set forth in SEQ ID NO:6. In some other specific embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two heavy chains of the anti-CD47 antibody, wherein the heavy chain fusion polypeptide includes the amino acid sequence as set forth in SEQ ID NO:24, and the light chain polypeptide includes the amino acid sequence as set forth in SEQ ID NO:6.

In some embodiments, another isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two heavy chains of the anti-CD47 antibody, wherein the heavy chain fusion polypeptide includes a sequence that is at least 80%, 85%, 90%, 95%, 96%, 97%, 98%, or 99% identical to the amino acid sequence as set forth in SEQ ID NO:10, SEQ ID NO:14, or SEQ ID NO:26, and the light chain polypeptide includes a sequence that is at least 80%, 85%, 90%, 95%, 96%, 97%, 98%, or 99% identical to the amino acid sequence as set forth in SEQ ID NO:6. In some embodiments, another isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two heavy chains of the anti-CD47 antibody, wherein the heavy chain fusion polypeptide includes a sequence that is at least 95% identical to the amino acid sequence as set forth in SEQ ID NO:10, SEQ ID NO:14, or SEQ ID NO:26, and the light chain polypeptide includes a sequence that is at least 95% identical to the amino acid sequence as set forth in SEQ ID NO:6. In some specific embodiments, another isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two heavy chains of the anti-CD47 antibody, wherein the heavy chain fusion polypeptide includes the amino acid sequence as set forth in SEQ ID NO:10, SEQ ID NO:14, or SEQ ID NO:26, and the light chain polypeptide includes the amino acid sequence as set forth in SEQ ID NO:6. In some other specific embodiments, another isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two heavy chains of the anti-CD47 antibody, wherein the heavy chain fusion polypeptide includes the amino acid sequence as set forth in SEQ ID NO:10, and the light chain polypeptide includes the amino acid sequence as set forth in SEQ ID NO:6. In some specific embodiments, another isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two heavy chains of the anti-CD47 antibody, wherein the heavy chain fusion polypeptide includes the amino acid sequence as set forth in SEQ ID NO:14, and the light chain polypeptide includes the amino acid sequence as set forth in SEQ ID NO:6. In some other specific embodiments, another isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two heavy chains of the anti-CD47 antibody, wherein the heavy chain fusion polypeptide includes the amino acid sequence as set forth in SEQ ID NO:26, and the light chain polypeptide includes the amino acid sequence as set forth in SEQ ID NO:6.

In some embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two light chains of the anti-CD47 antibody, wherein the light chain fusion polypeptide includes a sequence that is at least 80%, 85%, 90%, 95%, 96%, 97%, 98%, or 99% identical to the amino acid sequence as set forth in SEQ ID NO:16, SEQ ID NO:20, or SEQ ID NO:28, and the heavy chain polypeptide includes a sequence that is at least 80%, 85%, 90%, 95%, 96%, 97%, 98%, or 99% identical to the amino acid sequence as set forth in SEQ ID NO:4. In some embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two light chains of the anti-CD47 antibody, wherein the light chain fusion polypeptide includes a sequence that is at least 95% identical to the amino acid sequence as set forth in SEQ ID NO:16, SEQ ID NO:20, or SEQ ID NO:28, and the heavy chain polypeptide includes a sequence that is at least 95% identical to the amino acid sequence as set forth in SEQ ID NO:4. In some specific embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two light chains of the anti-CD47 antibody, wherein the light chain fusion polypeptide includes the amino acid sequence as set forth in SEQ ID NO:16, SEQ ID NO:20, or SEQ ID NO:28, and the heavy chain polypeptide includes the amino acid sequence as set forth in SEQ ID NO:4. In some other embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two light chains of the anti-CD47 antibody, wherein the light chain fusion polypeptide includes the amino acid sequence as set forth in SEQ ID NO:16, and the heavy chain polypeptide includes the amino acid sequence as set forth in SEQ ID NO:4. In some specific embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two light chains of the anti-CD47 antibody, wherein the light chain fusion polypeptide includes the amino acid sequence as set forth in SEQ ID NO:20, and the heavy chain polypeptide includes the amino acid sequence as set forth in SEQ ID NO:4. In some other specific embodiments, an isolated anti-CD47/anti-LAG-3 bispecific antigen-binding protein or a fragment thereof is provided, including an anti-CD47 antibody and an anti-LAG-3 sdAb, with the N-terminus of the anti-LAG-3 sdAb fused to the C-terminus of two light chains of the anti-CD47 antibody, wherein the light chain fusion polypeptide includes the amino acid sequence as set forth in SEQ ID NO:28, and the heavy chain polypeptide includes the amino acid sequence as set forth in SEQ ID NO:4.

In some embodiments, an isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two light chains of the anti-CD47 antibody, wherein the light chain fusion polypeptide includes a sequence that is at least 80%, 85%, 90%, 95%, 96%, 97%, 98%, or 99% identical to the amino acid sequence as set forth in SEQ ID NO:18, SEQ ID NO:22, or SEQ ID NO:30, and the heavy chain polypeptide includes a sequence that is at least 80%, 85%, 90%, 95%, 96%, 97%, 98%, or 99% identical to the amino acid sequence as set forth in SEQ ID NO:4. In some embodiments, an isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two light chains of the anti-CD47 antibody, wherein the light chain fusion polypeptide includes a sequence that is at least 95% identical to the amino acid sequence as set forth in SEQ ID NO:18, SEQ ID NO:22, or SEQ ID NO:30, and the heavy chain polypeptide includes a sequence that is at least 95% identical to the amino acid sequence as set forth in SEQ ID NO:4. In some specific embodiments, an isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two light chains of the anti-CD47 antibody, wherein the light chain fusion polypeptide includes the amino acid sequence as set forth in SEQ ID NO:18, SEQ ID NO:22, or SEQ ID NO:30, and the heavy chain polypeptide includes the amino acid sequence as set forth in SEQ ID NO:4. In some other specific embodiments, an isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two light chains of the anti-CD47 antibody, wherein the light chain fusion polypeptide includes the amino acid sequence as set forth in SEQ ID NO:18, and the heavy chain polypeptide includes the amino acid sequence as set forth in SEQ ID NO:4. In some specific embodiments, an isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two light chains of the anti-CD47 antibody, wherein the light chain fusion polypeptide includes the amino acid sequence as set forth in SEQ ID NO:22, and the heavy chain polypeptide includes the amino acid sequence as set forth in SEQ ID NO:4. In some other specific embodiments, an isolated anti-CD47/anti-LAG-3 bispecific antigen-binding protein or a fragment thereof is provided, including an anti-CD47 antibody and an anti-LAG-3 sdAb, with the C-terminus of the anti-LAG-3 sdAb fused to the N-terminus of two light chains of the anti-CD47 antibody, wherein the light chain fusion polypeptide includes the amino acid sequence as set forth in SEQ ID NO:30, and the heavy chain polypeptide includes the amino acid sequence as set forth in SEQ ID NO:4.

According to another aspect, the present invention provides an isolated polynucleotide encoding the anti-CD47/anti-LAG-3 bispecific antigen-binding protein or the fragment thereof. It can be commonly known to those skilled in the art that the change (such as replacement or deletion) of sequences encoding the protein does not change the amino acid of the protein. In some embodiments, the polynucleotide encoding the heavy chain fusion protein of the anti-CD47/anti-LAG-3 bispecific antigen-binding protein or the fragment thereof includes a sequence that is at least 80%, 85%, 90%, 95%, 96%, 97%, 98%, or 99% identical to the nucleotide sequence as set forth in SEQ ID NO:7, SEQ ID NO:9, SEQ ID NO:11, SEQ ID NO:13, SEQ ID NO:23, or SEQ ID NO:25, and the polynucleotide encoding the light chain polypeptide of the anti-CD47/anti-LAG-3 bispecific antigen-binding protein or the fragment thereof includes a sequence that is at least 80%, 85%, 90%, 95%, 96%, 97%, 98%, or 99% identical to the nucleotide sequence as set forth in SEQ ID NO:5. In some specific embodiments, the polynucleotide encoding the heavy chain fusion protein of the anti-CD47/anti-LAG-3 bispecific antigen-binding protein or the fragment thereof includes the nucleotide sequence as set forth in SEQ ID NO:7, SEQ ID NO:9, SEQ ID NO:11, SEQ ID NO:13, SEQ ID NO:23, or SEQ ID NO:25, and the polynucleotide encoding the light chain polypeptide of the anti-CD47/anti-LAG-3 bispecific antigen-binding protein or the fragment thereof includes the nucleotide sequence as set forth in SEQ ID NO:5. In some embodiments, the polynucleotide encoding the light chain fusion protein of the anti-CD47/anti-LAG-3 bispecific antigen-binding protein or the fragment thereof includes a sequence that is at least 80%, 85%, 90%, 95%, 96%, 97%, 98%, or 99% identical to the nucleotide sequence as set forth in SEQ ID NO:15, SEQ ID NO:17, SEQ ID NO:19, SEQ ID NO:21, SEQ ID NO:27, or SEQ ID NO:29, and the polynucleotide encoding the heavy chain polypeptide of the anti-CD47/anti-LAG-3 bispecific antigen-binding protein or the fragment thereof includes a sequence that is at least 80%, 85%, 90%, 95%, 96%, 97%, 98%, or 99% identical to the nucleotide sequence as set forth in SEQ ID NO:3. In some specific embodiments, the polynucleotide encoding the light chain fusion protein of the anti-CD47/anti-LAG-3 bispecific antigen-binding protein or the fragment thereof includes the nucleotide sequence as set forth in SEQ ID NO:15, SEQ ID NO:17, SEQ ID NO:19, SEQ ID NO:21, SEQ ID NO:27, or SEQ ID NO:29, and the polynucleotide encoding the heavy chain polypeptide of the anti-CD47/anti-LAG-3 bispecific antigen-binding protein or the fragment thereof includes the nucleotide sequence as set forth in SEQ ID NO:3.

Further, a vector including the isolated polynucleotide encoding the isolated anti-CD47/anti-LAG-3 bispecific antigen-binding protein or the fragment thereof is provided. It can be commonly known to those skilled in the art that a vector is a plasmid, a phage vector, or a viral vector. In some specific embodiments, the vector is a recombinant expression vector, for example, a plasmid. These vectors include various elements to support the functions thereof as conventional expression vectors, for example, including promoters, ribosome binding elements, terminators, enhancers, selective markers, and origins of replication. The promoters may be conventional promoters, inducible promoters, or repressible promoters. It can be commonly known in the art that many expression vectors can deliver nucleic acids into cells and can be used to produce antibodies or antigen-binding fragments thereof in cells. According to the method in examples of the present invention, conventional cloning techniques or artificial gene synthesis can be used to produce recombinant expression vectors.

Further, a host cell including the isolated polynucleotide or the vector is provided. In the present invention, any host cell conventional in the art can be used for the expression of antibodies or antigen-binding fragments thereof. In some embodiments, the host cell is *E. coli* TG1 or BL21 (used to express scFv or Fab antibodies), CHO-DG44, CHO-3E7, CHO-K1, or HEK293. According to specific examples, the recombinant expression vector is transfected into the host cell by a conventional method (such as chemical transfection, thermal transfection, or electro-transfection), and is stably integrated into the host cell genome, so that the recombinant nucleic acids can be effectively expressed.

According to another aspect, the present invention provides a method for producing an isolated anti-CD47/anti-LAG-3 bispecific antigen-binding protein or a fragment thereof, including culturing the host cell including the polynucleotide encoding the bispecific antigen-binding protein or the fragment thereof in the present invention under proper conditions, and recovering an antibody or a fragment thereof from the cell or a cell culture medium. The expression antibody or the fragment thereof may be obtained from cells or extracted and purified by using conventional methods in the art.

According to another aspect, the present invention provides a pharmaceutical composition, including the isolated anti-CD47/anti-LAG-3 bispecific antigen-binding protein or the fragment thereof and a pharmaceutically acceptable carrier. The "pharmaceutically acceptable carrier" refers to a solid or liquid diluent, a filler, an antioxidant, a stabilizer, or other substances that can be administered safely. These substances are suitable for human and/or animal administration without excessive side effects, and are suitable for maintaining the activity of drugs or active agents therein. Different carriers well known in the art may be administered according to the route of administration, including, but not limited to, carbohydrates, starch, cellulose and derivatives thereof, maltose, gelatin, talc, calcium sulfate, vegetable oils, synthetic oils, polyols, alginic acid, phosphate buffers, emulsifiers, isotonic saline, and/or pyrogen-free water. The pharmaceutical composition provided in the present invention may be prepared into clinically acceptable dosage forms such as powders and injections. Any proper route may be used to administer the pharmaceutical composition of the present invention to subjects, for example, it may be administered by oral, intravenous infusion, intramuscular injection, subcutaneous injection, subperitoneal, rectal, sublingual, inhalation, or transdermal.

According to another aspect, the present invention provides a method for treating subjects suffering from or at risk of suffering from diseases related to abnormal expression of CD47 and/or LAG-3, including administering the pharmaceutical composition with an effective amount to the subjects.

According to another aspect, the present invention provides use of the anti-CD47/anti-LAG-3 bispecific antigen-binding protein or the fragment thereof, the polynucleotide, the vector, and the host cell in preparing medicines for diseases related to abnormal expression of CD47 and/or LAG-3.

In some embodiments, the diseases related to abnormal expression of CD47 and/or LAG-3 are cancers. In some embodiments, the cancers include hematological tumors and solid tumors, wherein the hematological tumors include myeloma, leukemia, lymphoma, and the like, and the solid tumors include colorectal cancer, non-small cell lung cancer, small cell lung cancer, ovarian cancer, breast cancer, pancreatic cancer, stomach cancer, bladder cancer, esophageal cancer, mesothelioma, melanoma, head and neck cancer, Hodgkin lymphoma, hepatocellular carcinoma, advanced kidney cancer, thyroid cancer, and the like. In a preferred embodiment, the cancers include lymphoma, melanoma, pancreatic cancer, non-small cell lung cancer, breast cancer, stomach cancer, colorectal cancer, head and neck cancer, hepatocellular carcinoma, ovarian cancer, and prostate cancer.

In some embodiments, the method further includes administering additional tumor treatment to the subjects, such as surgery, radiation therapy, chemotherapy, immunotherapy, hormone therapy, or a combination thereof.

In the present invention, the LAG-3 sdAb is linked to the C-terminus of the heavy chain of the anti-CD47 monoclonal antibody in a specific way, and the produced anti-CD47/anti-LAG-3 bispecific antigen-binding protein has significantly increased affinity for LAG-3 antigen. It was indicated based on the cell phagocytosis experiment result of the anti-CD47 antibody that the biological activity of the bispecific antibody is higher than that of the anti-CD47 antibody control. In addition, this bispecific antibody can also block the LAG-3 signaling pathway, so that it can block two ways of tumor immune escape at the same time.

Explanation of Terms

An "antigen-binding protein fragment" means a fragment of an antibody and an antibody mimetic, generally including at least part of the antigen binding regions or variable regions (for example, one or more CDRs) of a parental antibody. The antibody fragment retains at least some of the binding specificity of the parental antibody. For example, the antigen-binding protein fragment that can bind to CD47 or part of it includes, but is not limited to, sdAb, Fab (for example, obtained by papain digestion of antibodies), F(ab')$_2$ (for example, obtained by pepsin digestion), and Fv or scFv (for example, obtained by molecular biology techniques).

"single domain antibody (sdAb)" refers to single antigen-binding polypeptide with three CDRs. The sdAb can bind to the antigen independently without pairing with corresponding CDR-containing polypeptide. In some cases, sdAb is artificially engineered from camelid heavy chain antibodies and is referred to as a "$V_H$H domain" Cartilaginous fishes also have heavy chain antibodies (immunoglobulin new antigen receptor (IgNAR)), and sdAb referred to as a "VNAR domain" may also be produced from this class of antibodies. Camelid sdAb is a smallest known antigen-binding antibody fragment (Refer to e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). The basic $V_H$H has the following structure from the N-terminus to the C-terminus: FR1-CDR1-FR2-CDR2-FR3-CDR3-FR4, where FR1 to FR4 are framework regions 1 to 4, and CDR1 to CDR3 are CDRs 1 to 3. The anti-LAG-3 sdAb in the present invention refers to sdAb that can specifically bind to LAG-3, in particular, sdAb that can bind to human LAG-3. The anti-LAG-3 sdAb in the present invention may be selected from the anti-LAG-3 sdAb specifically described in the patent application PCT/CN2019/080528. The construction, expression, extraction, and purification methods of the anti-LAG-3 sdAb in the present invention may refer to the patent application PCT/CN2019/080528.

A "full-length antibody" refers to an antibody having four full-length chains, including heavy chains and light chains containing Fc regions. The anti-CD47 antibody in the present invention refers to an antibody that can specifically bind to CD47, in particular, an antibody that can bind to human CD47. The anti-CD47 antibody in the present invention may be selected from the anti-CD47 antibody specifically described in PCT/CN2019/072929. The construction, expression, extraction, and purification methods of the anti-CD47 antibody in the present invention may refer to the patent application PCT/CN2019/072929.

A "mutation" is an alteration of one or more (several) amino acid residues at one or more (several) locations included in an antigen-binding protein or a protein fragment, that is, a polypeptide includes substitution(s), insertion(s), and/or deletion(s). The substitutions refer to substituting different amino acids for the amino acid occupying a certain location. The deletions refer to deleting the amino acid occupying a certain location. The insertions refer to inserting 1 to 5 amino acids after the amino acid occupying a certain location.

The "amino acid sequence identity" is defined as the percentage of amino acid residues in a candidate sequence identical to the amino acid residues in a specific peptide or polypeptide sequence after the sequences are compared and gaps are introduced when necessary to obtain the maximum percent sequence identity without considering any conservative substitutions as part of the sequence identity. Sequence comparison can be performed in a variety of ways within the skill of the art to determine percent amino acid sequence identity, for example, publicly available computer software such as BLAST, BLAST-2, ALIGN or Megalign (DNASTAR) software is used. Those skilled in the art can determine appropriate parameters for measuring the comparison, including any algorithm required to obtain the maximum comparison over the full length of the compared sequences.

A "GS linker" refers to the GS combination of glycine (G) and serine (S), and is used to link a plurality of proteins together to form a fusion protein. The commonly used GS combination is (GGGGS)n, which changes the length of the linker sequence by changing n, and most of the GS combination is (GGGGS)3. In addition, glycine and serine may also produce different linker sequences through other combinations, for example, the GS combination of G15-linker used in the present invention is GGGGSGGGSGGGGS, and the GS combination of G9-linker is GGGGSGGGS.

DETAILED DESCRIPTION

Figure 1:
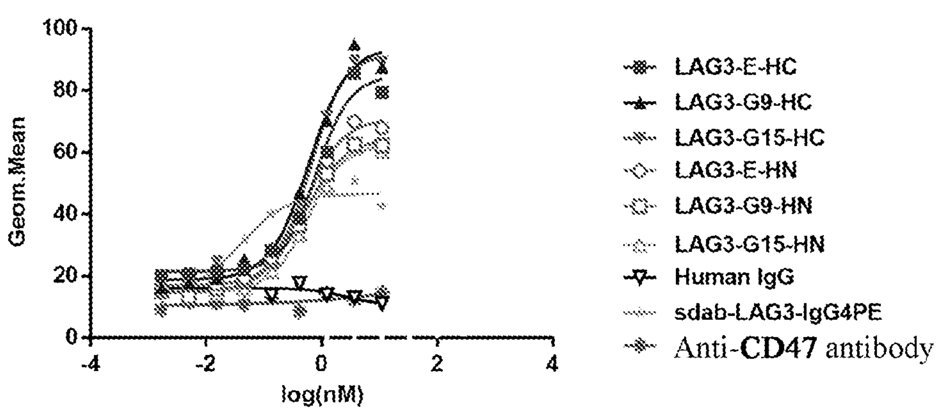
FIG. 1 shows the affinity between a sample and CHO-K1 cells expressing human LAG-3 measured by a flow cytometer.

The present invention is described in detail below with reference to specific implementations. It should be understood that these implementations are merely intended to describe the present invention rather than to limit the scope of the present invention. In addition, it should be understood that, after reading the teaching of the present invention, those skilled in the art may make various changes or modifications to the present invention, and these equivalent forms also fall within the scope defined by the appended claims of this application. Unless otherwise specified, the methods and materials in the examples described below are commercially available and conventional products.

Example 1 Construction and Expression of Anti-CD47/aNti-LAG-3 Bispecific Antibody A series of anti-CD47/anti-LAG-3 bispecific antibodies were designed by using an anti-CD47 monoclonal antibody (mAb) (the CDR, full-length nucleotide, and amino acid sequence of the antibody are shown in Table 1) and a LAG-3 sdAb (the CDR, full-length nucleotide, and amino acid sequence of the antibody are shown in Table 2). The LAG-3 sdAb was fused to the N-terminus or C-terminus of the heavy chain or light chain of the anti-CD47 mAb by using three linker sequences (E-linker: EPKSSDKTHTSPPSP, G15-linker: GGGGSGGGGSGGGGS, or G9-linker: GGGGSGGGS). Each bispecific antibody structure was composed of two identical fused polypeptide chains and two identical natural polypeptide chains. The DNA sequence expressing each polypeptide chain was inserted on the pTT5 vector between EcoRI and HindIII restriction sites. Each plasmid also includes a secretion signal sequence of a protein secreted into a growth medium. The LAG-3 sdAb was fused to the N-terminus of IgG4-Fc with site mutation (S228P and L235E), as a control for in vitro biological activity measurement. The plasmids expressing the bispecific antibody proteins are shown in Table 3.

TABLE 1

| DNA and amino acid sequences of anti-CD47 mAb | | |
|---|---|---|
| | Sequence | SEQ ID NO: |
| Heavy chain DNA sequence of anti-CD47 antibody | GAGGTGCAGCTGGTGCAGTCCGGAGCTGAGGTGAA GAAGCCAGGATCCAGCGTGAAGGTGAGCTGCAAGG CTAGCGGCTACTCTTTCACCCACCATTGGATCCACTG GGTGAGGCAGGCTCCTGGACAGGGACTGGAGTGGAT GGGCATGATCGACGCTTCCGATAGCGAGACAAGACT GTCTCAGAAGTTTAAGGACCGCGTGACCATCACAGC CGATAAGTCTACCTCCACAGCTTACATGGAGCTGTCT TCCCTGAGATCCGAGGACACCGCCGTGTACTATTGTG CTAGGCTGGGCCGGTACTATTTCGATTATTGGGGCCA GGGCACCACAGTGACAGTGAGCTCTGCCAGCACAA AGGGCCCTTCCGTGTTCCCACTGGCTCCCTGCTCCAG AAGCACATCTGAGTCCACCGCCGCTCTGGGCTGTCT GGTGAAGGACTACTTCCCTGAGCCAGTGACCGTGTC CTGGAACAGCGGCGCCCTGACATCTGGCGTGCACAC CTTTCCAGCTGTGCTGCAGTCCAGCGGCCTGTACTCC CTGTCTTCCGTGGTGACAGTGCCCAGCTCTTCCCTGG GCACCAAGACATATACCTGCAACGTGGACCATAAGC CTTCCAATACCAAGGTGGATAAGAGGGTGGAGAGCA AGTACGGACCACCTTGCCCACCATGTCCAGCTCCTG AGTTTGAGGGAGGACCATCCGTGTTCCTGTTTCCTCC AAAGCCTAAGGACACCCTGATGATCAGCCGGACACC TGAGGTGACCTGCGTGGTGGTGGACGTGTCTCAGGA GGATCCAGAGGTGCAGTTCAACTGGTACGTGGATGG CGTGGAGGTGCACAATGCTAAGACCAAGCCAAGAG AGGAGCAGTTTAATTCCACATACCGCGTGGTGAGCG TGCTGACCGTGCTGCATCAGGATTGGCTGAACGGCA AGGAGTATAAGTGCAAGGTGTCCAATAAGGGCCTGC CCAGCTCTATCGAGAAGACAATCAGCAAGGCTAAGG GACAGCCTAGGGAGCCACAGGTGTACACCCTGCCCC CTTCTCAGGAGGAGATGACAAAGAACCAGGTGTCCC TGACCTGTCTGGTGAAGGGCTTCTATCCAAGCGACAT CGCTGTGGAGTGGGAGTCTAATGGCCAGCCCGAGAA CAATTACAAGACCACACCACCCGTGCTGGACTCTGA TGGCTCCTTCTTTCTGTATTCTAGGCTGACAGTGGATA AGTCCCGGTGGCAGGAGGGCAACGTGTTTAGCTGCT CTGTGATGCACGAGGCCCTGCACAATCATTATACCCA GAAGTCCCTGAGCCTGTCTCTGGGCAAG | 3 |
| Heavy chain amino acid sequence H0 of anti-CD47 antibody | EVQLVQSGAEVKKPGSSVKVSCKASGYSFTHHWIHWV RQAPGQGLEWMGMIDASDSETRLSQKFKDRVTITADK STSTAYMELSSLRSEDTAVYYCARLGRYYFDYWGQGT TVTVSSASTKGPSVFPLAPCSRSTSESTAALGCLVKDYF PEPVTVSWNSGALTSGVHTFPAVLQSSGLYSLSSVVTVP SSSLGTKTYTCNVDHKPSNTKVDKRVESKYGPPCPPCP APEFEGGPSVFLFPPKPKDTLMISRTPEVTCVVVDVSQE DPEVQFNWYVDGVEVHNAKTKPREEQFNSTYRVVSV LTVLHQDWLNGKEYKCKVSNKGLPSSIEKTISKAKGQP REPQVYTLPPSQEEMTKNQVSLTCLVKGFYPSDIAVEW ESNGQPENNYKTTPPVLDSDGSFFLYSRLTVDKSRWQE GNVFSCSVMHEALHNHYTQKSLSLSLGK | 4 |
| Light chain DNA sequence of anti-CD47 antibody | GAGATCGTGCTGACCCAGTCTCCAGCCACACTGTCT CTGTCCCCAGGAGAGAGGGCCACCCTGAGCTGCCGG GCTTCTGAGAACGTGGGCACATACATCTCCTGGTATC AGCAGAAGCCAGGACAGGCTCCTAGGCTGCTGATCT ACGGCGCTAGCAATAGATATACCGGCATCCCTGCTCG CTTCAGCGGATCTGGATCCGGCACAGACTTTACCCTG ACAATCTCCAGCCTGGAGCCAGAGGATTTCGCCGTG TACTATTGTGGCGAGTCCTACGGCCACCTGTATACCTT TGGCGGCGGCACAAAGGTGGAGATCAAGCGAACGG TGGCTGCACCATCTGTCTTCATCTTCCCGCCATCTGAT GAGCAGTTGAAATCTGGAACTGCCTCTGTTGTGTGC CTGCTGAATAACTTCTATCCCAGAGAGGCCAAAGTAC AGTGGAAGGTGGATAACGCCCTCCAATCGGGTAACT CCCAGGAGAGTGTCACAGAGCAGGACAGCAAGGAC AGCACCTACAGCCTCAGCAGCACCCTGACGCTGAGC AAAGCAGACTACGAGAAACACAAAGTCTACGCCTGC GAAGTCACCCATCAGGGCCTGAGCTCGCCCGTCACA AAGAGCTTCAACAGGGGAGAGTGT | 5 |

TABLE 1-continued

| DNA and amino acid sequences of anti-CD47 mAb | | | | | | |
|---|---|---|---|---|---|---|
| Light chain amino acid sequence L0 of anti-CD47 antibody | EIVLTQSPATLSLSPGERATLSCRASENVGTYISWYQQK PGQAPRLLIYGASNRYTGIPARFSGSGSGTDFTLTISSLE PEDFAVYYCGESYGHLYTFGGGTKVEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC | | | | 6 | |
| | CDR1 sequence | SEQ ID NO: | CDR2 sequence | SEQ ID NO: | CDR3 sequence | SEQ ID NO: |
| Heavy chain CDR sequence of anti-CD47 antibody | GYSFTH HWIH | 33 | MIDASDSET RLSQKFKD | 34 | LGRYYF DY | 35 |
| Light chain CDR sequence of anti-CD47 antibody | RASEN VGTYIS | 36 | GASNRYT | 37 | GESYGH LYT | 38 |

TABLE 2

| DNA and amino acid sequences of LAG-3 sdAb | | | | | | |
|---|---|---|---|---|---|---|
| | Sequence | | | | SEQ ID NO: | |
| DNA LAG-3 sdAb | GAGGTGCAGCTGGTGGAGTCCGGAGGAGGACTGGTGC GGCTACACCGTGTCCAGCTATTGTATGGGCTGGTTCAGG CAGGCTCCTGGCAAGGGAAGGGAGGGCGTGTCCGCTAT CGACAGCGATGGCAGCGTGTCTTACGCCGACAGCGTGA AGGGCAGATTCACCATCTCTAAGGATAACTCCAAGAATA CACTGTACCTGCAGATGAACTCTCTGCGCGCCGAGGAC ACCGCCGTGTACTTTTGCGCTGCTGACCTGTGCTGGGTG GACCAGGATCAGGGCGAGTATAATACATGGGGCCAGGG CACCCTGGTGACAGTGTCTTCC | | | | 39 | |
| Amino acid sequence of LAG-3 sdAb | EVQLVESGGGLVQPGGSLRLSCAASGYTVSSYCMGWFRQ APGKGREGVSAIDSDGSVSYADSVKGRFTISKDNSKNTLY LQMNSLRAEDTAVYFCAADLCWVDQDQGEYNTWGQGT LVTVSS | | | | 40 | |
| | CDR1 sequence | SEQ ID NO: | CDR2 sequence | SEQ ID NO: | CDR3 sequence | SEQ ID NO: |
| CDR amino acid sequence of LAG-3 sdAb | GYTVSS YCMG | 41 | AIDSDGSV SYADSVKG | 42 | DLCWVDQ DQGEYNT | 43 |

After the expression plasmids were transfected into CHO-3E7 host cells, the resulting host cells were cultured in an incubator at 37° C. and 100 rpm for 6 days. The supernatants were extracted by centrifugation, and bispecific antibody proteins were purified with a Protein A column.

As described above, the anti-CD47 mAb was composed of the heavy chain H0 and the light chain L0. The LAG-3 sdAb was fused to the N-terminus or C-terminus of the heavy chain or light chain of the anti-CD47 mAb by three linker sequences (E-linker: EPKSSDKTHTSPPSP, G15-linker: GGGGSGGGGSGGGGS, or G9-linker: GGGGSGGGS) to produce a series of different bispecific antibodies. First, the E-linker sequence was used to construct the following fusion proteins: (1). the LAG-3 sdAb was fused to the C-terminus of the heavy chain H0 to produce a new polypeptide referred to as H1; (2). the LAG-3 sdAb was fused to the N-terminus of the heavy chain H0 to produce a new polypeptide referred to as H2; (3). the LAG-3 sdAb was fused to the C-terminus of the light chain L0 to produce a new polypeptide referred to as L1; and (4). the LAG-3 sdAb was fused to the N-terminus of the light chain L0 to produce a new polypeptide referred to as L2. Similarly, the G9-linker sequence was used to construct the following fusion proteins: (1). the LAG-3 sdAb was fused to the C-terminus of the heavy chain H0 to produce a new polypeptide referred to as H3; (2). the LAG-3 sdAb was fused to the N-terminus of the heavy chain H0 to produce a new polypeptide referred to as H4; (3). the LAG-3 sdAb was fused to the C-terminus of the light chain L0 to produce a new polypeptide referred to as L3; and (4). the LAG-3 sdAb was fused to the N-terminus of the light chain L0 to produce a new polypeptide referred to as L4. Then, the G15-linker sequence was used to construct the following fusion proteins: (1). the LAG-3 sdAb was fused to the C-terminus of the heavy chain H0 to produce a new polypeptide referred to as H5; (2). the LAG-3 sdAb was fused to the N-terminus of the heavy chain H0 to produce a new polypeptide referred to as H6; (3). the LAG-3 sdAb was fused to the C-terminus of the light chain L0 to produce a new polypeptide referred to as L5; and (4). the LAG-3 sdAb was fused to the N-terminus of the light chain L0 to produce a new polypeptide referred to as L6.

These constructed heavy chain fusion proteins H1, H2, H3, H4, H5, and H6 were separately combined with the unmodified parental light chain polypeptide chain L0, or these constructed light chain fusion proteins L1, L2, L3, L4, L5, and L6 were separately combined with the unmodified heavy chain polypeptide chain H0, to produce a series of bispecific antibodies. The heavy chain fusion protein H1 was combined with the parental light chain L0 to produce a bispecific antibody LAG3-E-HC. The heavy chain fusion protein H2 was combined with the parental light chain L0 to produce a bispecific antibody LAG3-E-HN. The heavy chain fusion protein H3 was combined with the parental light chain L0 to produce a bispecific antibody LAG3-G9-HC. The heavy chain fusion protein H4 was combined with the parental light chain L0 to produce a bispecific antibody LAG3-G9-HN. The heavy chain fusion protein H5 was combined with the parental light chain L0 to produce a bispecific antibody LAG3-G15-HC. The heavy chain fusion protein H6 was combined with the parental light chain L0 to produce a bispecific antibody LAG3-G15-HN. The light chain fusion protein L1 was combined with the parental heavy chain H0 to produce a bispecific antibody LAG3-E-LC. The light chain fusion protein L2 was combined with the parental heavy chain H0 to produce a bispecific antibody LAG3-E-LN. The light chain fusion protein L3 was combined with the parental heavy chain H0 to produce a bispecific antibody LAG3-G9-LC. The light chain fusion protein L4 was combined with the parental heavy chain H0 to produce a bispecific antibody LAG3-G9-LN. The light chain fusion protein L5 was combined with the parental heavy chain H0 to produce a bispecific antibody LAG3-G15-LC. The light chain fusion protein L6 was combined with the parental heavy chain H0 to produce a bispecific antibody LAG3-G15-LN.

TABLE 3

Plasmids and proteins for construction of bispecific antibodies

| Protein | Component | Plasmid | Amino acid SEQ ID NO: |
|---|---|---|---|
| CD47 | H0 | pTT5-CD47HC | 4 |
| | L0 | pTT5-CD47LC | 6 |
| LAG3-E-HC | H1 | pTT5 -CD47HC-E-LAG3 | 8 |
| | L0 | pTT5-CD47LC | 6 |
| LAG3-E-HN | H2 | pTT5-LAG3-E-CD47HC | 10 |
| | L0 | pTT5-CD47LC | 6 |
| LAG3-E-LC | L1 | pTT5 -CD47LC-E-LAG3 | 16 |
| | H0 | pTT5-CD47HC | 4 |
| LAG3-E-LN | L2 | pTT5-LAG3-E-CD47LC | 18 |
| | H0 | pTT5-CD47HC | 4 |
| LAG3-G9-HC | H3 | pTT5-CD47HC-G9-LAG3 | 12 |
| | L0 | pTT5-CD47LC | 6 |
| LAG3-G9-HN | H4 | pTT5-LAG3-G9-CD47HC | 14 |
| | L0 | pTT5-CD47LC | 6 |
| LAG3-G9-LC | L3 | pTT5-CD47LC-G9-LAG3 | 20 |
| | H0 | pTT5-CD47HC | 4 |
| LAG3-G9-LN | L4 | pTT5-LAG3-G9-CD47LC | 22 |
| | H0 | pTT5-CD47HC | 4 |
| LAG3-G15-HC | H5 | pTT5-CD47HC-G15-LAG3 | 24 |
| | L0 | pTT5-CD47LC | 6 |
| LAG3-G15-HN | H6 | pTT5-LAG3-G15-CD47HC | 26 |
| | L0 | pTT5-CD47LC | 6 |
| LAG3-G15-LC | L5 | pTT5 -CD47LC-G15-LAG3 | 28 |
| | H0 | pTT5-CD47HC | 4 |
| LAG3-G15-LN | L6 | pTT5-LAG3-G15-CD47LC | 30 |
| | H0 | pTT5-CD47HC | 4 |
| sdAb-LAG3-IgG4PE | H7 | pTT5-sdAb-LAG3-IgG4PE | 32 |

The human IgG4-Fc was modified by site mutation (S228P and L235E), and then the LAG-3 sdAb was linked to the N-terminus of the human IgG4-Fc, to produce a new fusion protein H7, to further construct the Fc fusion protein sdAb-LAG3-IgG4PE.

```
DNA sequence of secretion signal peptide
                                                    (SEQ ID NO: 1)
ATGGGCTGGTCCTGCATCATCCTGTTCCTGGTGGCTACCGCCACCGGCGTGCA

CTCC

Amino acid sequence of secretion signal peptide
                                                    (SEQ ID NO: 2)
MGWSCIILFLVATATGVHS
```

-continued

DNA sequence of polypeptide chain H0

(SEQ ID NO: 3)

GAGGTGCAGCTGGTGCAGTCCGGAGCTGAGGTGAAGAAGCCAGGATCCAGC

GTGAAGGTGAGCTGCAAGGCTAGCGGCTACTCTTTCACCCACCATTGGATCCACT

GGGTGAGGCAGGCTCCTGGACAGGGACTGGAGTGGATGGGCATGATCGACGCTT

CCGATAGCGAGACAAGACTGTCTCAGAAGTTTAAGGACCGCGTGACCATCACAGC

CGATAAGTCTACCTCCACAGCTTACATGGAGCTGTCTTCCCTGAGATCCGAGGACA

CCGCCGTGTACTATTGTGCTAGGCTGGGCCGGTACTATTTCGATTATTGGGGCCAG

GGCACCACAGTGACAGTGAGCTCTGCCAGCACAAAGGGCCCTTCCGTGTTCCCA

CTGGCTCCCTGCTCCAGAAGCACATCTGAGTCCACCGCCGCTCTGGGCTGTCTGG

TGAAGGACTACTTCCCTGAGCCAGTGACCGTGTCCTGGAACAGCGGCGCCCTGAC

ATCTGGCGTGCACACCTTTCCAGCTGTGCTGCAGTCCAGCGGCCTGTACTCCCTGT

CTTCCGTGGTGACAGTGCCCAGCTCTTCCCTGGGCACCAAGACATATACCTGCAA

CGTGGACCATAAGCCTTCCAATACCAAGGTGGATAAGAGGGTGGAGAGCAAGTAC

GGACCACCTTGCCCACCATGTCCAGCTCCTGAGTTTGAGGGAGGACCATCCGTGT

TCCTGTTTCCTCCAAAGCCTAAGGACACCCTGATGATCAGCCGGACACCTGAGGT

GACCTGCGTGGTGGTGGACGTGTCTCAGGAGGATCCAGAGGTGCAGTTCAACTG

GTACGTGGATGGCGTGGAGGTGCACAATGCTAAGACCAAGCCAAGAGAGGAGCA

GTTTAATTCCACATACCGCGTGGTGAGCGTGCTGACCGTGCTGCATCAGGATTGGC

TGAACGGCAAGGAGTATAAGTGCAAGGTGTCCAATAAGGGCCTGCCCAGCTCTAT

CGAGAAGACAATCAGCAAGGCTAAGGGACAGCCTAGGGAGCCACAGGTGTACAC

CCTGCCCCCTTCTCAGGAGGAGATGACAAAGAACCAGGTGTCCCTGACCTGTCTG

GTGAAGGGCTTCTATCCAAGCGACATCGCTGTGGAGTGGGAGTCTAATGGCCAGC

CCGAGAACAATTACAAGACCACACCACCCGTGCTGGACTCTGATGGCTCCTTCTT

TCTGTATTCTAGGCTGACAGTGGATAAGTCCCGGTGGCAGGAGGGCAACGTGTTT

AGCTGCTCTGTGATGCACGAGGCCCTGCACAATCATTATACCCAGAAGTCCCTGAG

CCTGTCTCTGGGCAAG

Amino acid sequence of polypeptide chain H0

(SEQ ID NO: 4)

EVQLVQSGAEVKKPGSSVKVSCKASGYSFTHHWIHWVRQAPGQGLEWMGMID

ASDSETRLSQKFKDRVTITADKSTSTAYMELSSLRSEDTAVYYCARLGRYYPDYWGQ

GTTVTVSSASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPCPP

CPAPEFEGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

DNA sequence of polypeptide chain L0

(SEQ ID NO: 5)

GAGATCGTGCTGACCCAGTCTCCAGCCACACTGTCTCTGTCCCCAGGAGAGA

GGGCCACCCTGAGCTGCCGGGCTTCTGAGAACGTGGGCACATACATCTCCTGGTA

TCAGCAGAAGCCAGGACAGGCTCCTAGGCTGCTGATCTACGGCGCTAGCAATAGA

TATACCGGCATCCCTGCTCGCTTCAGCGGATCTGGATCCGGCACAGACTTTACCCT

-continued

GACAATCTCCAGCCTGGAGCCAGAGGATTTCGCCGTGTACTATTGTGGCGAGTCCT

ACGGCCACCTGTATACCTTTGGCGGCGGCACAAAGGTGGAGATCAAGCGAACGGT

GGCTGCACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGC

AGGACAGCAAGGACAGCACCTACAGCCTCAGCAGCACCCTGACGCTGAGCAAAG

CAGACTACGAGAAACACAAAGTCTACGCCTGCGAAGTCACCCATCAGGGCCTGA

GCTCGCCCGTCACAAAGAGCTTCAACAGGGGAGAGTGT

Amino acid sequence of polypeptide chain L0

(SEQ ID NO: 6)

EIVLTQSPATLSLSPGERATLSCRASENVGTYISWYQQKPGQAPRLLIYGASNRYT

GIPARFSGSGSGTDFTLTISSLEPEDFAVYYCGESYGHLYTFGGGTKVEIKRTVAAPSVF

IFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

DNA sequence of polypeptide chain H1

(SEQ ID NO: 7)

GAGGTGCAGCTGGTGCAGTCCGGAGCTGAGGTGAAGAAGCCAGGATCCAGC

GTGAAGGTGAGCTGCAAGGCTAGCGGCTACTCTTTCACCCACCATTGGATCCACT

GGGTGAGGCAGGCTCCTGGACAGGGACTGGAGTGGATGGGCATGATCGACGCTT

CCGATAGCGAGACAAGACTGTCTCAGAAGTTTAAGGACCGCGTGACCATCACAGC

CGATAAGTCTACCTCCACAGCTTACATGGAGCTGTCTTCCCTGAGATCCGAGGACA

CCGCCGTGTACTATTGTGCTAGGCTGGGCCGGTACTATTTCGATTATTGGGGCCAG

GGCACCACAGTGACAGTGAGCTCTGCCAGCACAAAGGGCCCTTCCGTGTTCCCA

CTGGCTCCCTGCTCCAGAAGCACATCTGAGTCCACCGCCGCTCTGGGCTGTCTGG

TGAAGGACTACTTCCCTGAGCCAGTGACCGTGTCCTGGAACAGCGGCGCCCTGAC

ATCTGGCGTGCACACCTTTCCAGCTGTGCTGCAGTCCAGCGGCCTGTACTCCCTGT

CTTCCGTGGTGACAGTGCCCAGCTCTTCCCTGGGCACCAAGACATATACCTGCAA

CGTGGACCATAAGCCTTCCAATACCAAGGTGGATAAGAGGGTGGAGAGCAAGTAC

GGACCACCTTGCCCACCATGTCCAGCTCCTGAGTTTGAGGGAGGACCATCCGTGT

TCCTGTTTCCTCCAAAGCCTAAGGACACCCTGATGATCAGCCGGACACCTGAGGT

GACCTGCGTGGTGGTGGACGTGTCTCAGGAGGATCCAGAGGTGCAGTTCAACTG

GTACGTGGATGGCGTGGAGGTGCACAATGCTAAGACCAAGCCAAGAGAGGAGCA

GTTTAATTCCACATACCGCGTGGTGAGCGTGCTGACCGTGCTGCATCAGGATTGGC

TGAACGGCAAGGAGTATAAGTGCAAGGTGTCCAATAAGGGCCTGCCCAGCTCTAT

CGAGAAGACAATCAGCAAGGCTAAGGGACAGCCTAGGGAGCCACAGGTGTACAC

CCTGCCCCCTTCTCAGGAGGAGATGACAAAGAACCAGGTGTCCCTGACCTGTCTG

GTGAAGGGCTTCTATCCAAGCGACATCGCTGTGGAGTGGGAGTCTAATGGCCAGC

CCGAGAACAATTACAAGACCACACCACCCGTGCTGGACTCTGATGGCTCCTTCTT

TCTGTATTCTAGGCTGACAGTGGATAAGTCCCGGTGGCAGGAGGGCAACGTGTTT

AGCTGCTCTGTGATGCACGAGGCCCTGCACAATCATTATACCCAGAAGTCCCTGAG

CCTGTCTCTGGGCAAGGAACCTAAGTCTAGCGACAAAACTCATACCAGCCCCCCT

AGTCCAGAGGTGCAGCTGGTGGAGTCCGGAGGAGGACTGGTGCAGCCAGGAGGC

TCCCTGAGGCTGAGCTGCGCCGCTTCTGGCTACACCGTGTCCAGCTATTGTATGGG

-continued

CTGGTTCAGGCAGGCTCCTGGCAAGGGAAGGGAGGGCGTGTCCGCTATCGACAG

CGATGGCAGCGTGTCTTACGCCGACAGCGTGAAGGGCAGATTCACCATCTCTAAG

GATAACTCCAAGAATACACTGTACCTGCAGATGAACTCTCTGCGCGCCGAGGACA

CCGCCGTGTACTTTTGCGCTGCTGACCTGTGCTGGGTGGACCAGGATCAGGGCGA

GTATAATACATGGGGCCAGGGCACCCTGGTGACAGTGTCTTCC

Amino acid sequence of polypeptide chain H1

(SEQ ID NO: 8)

EVQLVQSGAEVKKPGSSVKVSCKASGYSFTHHWIHWVRQAPGQGLEWMGMID

ASDSETRLSQKFKDRVTITADKSTSTAYMELSSLRSEDTAVYYCARLGRYYPDYWGQ

GTTVTVSASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPCPP

CPAPEFEGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKEPKSSDKTHT

SPPSPEVQLVESGGGLVQPGGSLRLSCAASGYTVSSYCMGWFRQAPGKGREGVSAID

SDGSVSYADSVKGRFTISKDNSKNTLYLQMNSLRAEDTAVYFCAADLCWVDQDQGE

YNTWGQGTLVTVSS

DNA sequence of polypeptide chain H2

(SEQ ID NO: 9)

GAGGTGCAGCTGGTGGAGTCCGGAGGAGGACTGGTGCAGCCAGGAGGCTCC

CTGAGGCTGAGCTGCGCCGCTTCTGGCTACACCGTGTCCAGCTATTGTATGGGCTG

GTTCAGGCAGGCTCCTGGCAAGGGAAGGGAGGGCGTGTCCGCTATCGACAGCGA

TGGCAGCGTGTCTTACGCCGACAGCGTGAAGGGCAGATTCACCATCTCTAAGGAT

AACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTA

TAATACATGGGGCCAGGGCACCCTGGTGACAGTGTCTTCCGAACCTAAGTCTAGC

GACAAAACTCATACCAGCCCCCCTAGTCCAGAGGTGCAGCTGGTGCAGTCCGGAG

CTGAGGTGAAGAAGCCAGGATCCAGCGTGAAGGTGAGCTGCAAGGCTAGCGGCT

ACTCTTTCACCCACCATTGGATCCACTGGGTGAGGCAGGCTCCTGGACAGGGACT

GGAGTGGATGGGCATGATCGACGCTTCCGATAGCGAGACAAGACTGTCTCAGAAG

TTTAAGGACCGCGTGACCATCACAGCCGATAAGTCTACCTCCACAGCTTACATGGA

GCTGTCTTCCCTGAGATCCGAGGACACCGCCGTGTACTATTGTGCTAGGCTGGGCC

GGTACTATTTCGATTATTGGGGCCAGGGCACCACAGTGACAGTGAGCTCTGCCAG

CACAAAGGGCCCTTCCGTGTTCCCACTGGCTCCCTGCTCCAGAAGCACATCTGAG

TCCACCGCCGCTCTGGGCTGTCTGGTGAAGGACTACTTCCCTGAGCCAGTGACCG

TGTCCTGGAACAGCGGCGCCCTGACATCTGGCGTGCACACCTTTCCAGCTGTGCT

GCAGTCCAGCGGCCTGTACTCCCTGTCTTCCGTGGTGACAGTGCCCAGCTCTTCCC

TGGGCACCAAGACATATACCTGCAACGTGGACCATAAGCCTTCCAATACCAAGGT

GGATAAGAGGGTGGAGAGCAAGTACGGACCACCTTGCCCACCATGTCCAGCTCCT

GAGTTTGAGGGAGGACCATCCGTGTTCCTGTTTCCTCCAAAGCCTAAGGACACCC

TGATGATCAGCCGGACACCTGAGGTGACCTGCGTGGTGGTGGACGTGTCTCAGGA

-continued

GGATCCAGAGGTGCAGTTCAACTGGTACGTGGATGGCGTGGAGGTGCACAATGCT
AAGACCAAGCCAAGAGAGGAGCAGTTTAATTCCACATACCGCGTGGTGAGCGTG
CTGACCGTGCTGCATCAGGATTGGCTGAACGGCAAGGAGTATAAGTGCAAGGTGT
CCAATAAGGGCCTGCCCAGCTCTATCGAGAAGACAATCAGCAAGGCTAAGGGACA
GCCTAGGGAGCCACAGGTGTACACCCTGCCCCCTTCTCAGGAGGAGATGACAAA
GAACCAGGTGTCCCTGACCTGTCTGGTGAAGGGCTTCTATCCAAGCGACATCGCT
GTGGAGTGGGAGTCTAATGGCCAGCCCGAGAACAATTACAAGACCACACCACCC
GTGCTGGACTCTGATGGCTCCTTCTTTCTGTATTCTAGGCTGACAGTGGATAAGTC
CCGGTGGCAGGAGGGCAACGTGTTTAGCTGCTCTGTGATGCACGAGGCCCTGCAC
AATCATTATACCCAGAAGTCCCTGAGCCTGTCTCTGGGCAAG

Amino acid sequence of polypeptide chain H2
(SEQ ID NO: 10)
EVQLVESGGGLVQPGGSLRLSCAASGYTVSSYCMGWFRQAPGKGREGVSAIDSD
GSVSYADSVKGRFTISKDNSKNTLYLQMNSLRAEDTAVYFCAADLCWVDQDQGEYN
TWGQGTLVTVSSEPKSSDKTHTSPPSPEVQLVQSGAEVKKPGSSVKVSCKASGYSFT
HHWIHWVRQAPGQGLEWMGMIDASDSETRLSQKFKDRVTITADKSTSTAYMELSSL
RSEDTAVYYCARLGRYYFDYWGQGTTVTVSSASTKGPSVFPLAPCSRSTSESTAALG
CLVKDYFPEPVTVSWNSGALTSGVHTFPAVLQSSGLYSLSSVVTVPSSSLGTKTYTCN
VDHKPSNTKVDKRVESKYGPPCPPCPAPEFEGGPSVFLFPPKPKDTLMISRTPEVTCVV
VDVSQEDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCLVKGFYPSDI
AVEWESNGQPENNYKTTPPVLDSDGSFFLYSRLTVDKSRWQEGNVFSCSVMHEALH
NHYTQKSLSLSLGK DNA sequence of polypeptide chain H3
(SEQ ID NO: 11)
GAGGTGCAGCTGGTGCAGTCCGGAGCTGAGGTGAAGAAGCCAGGATCCAGC
GTGAAGGTGAGCTGCAAGGCTAGCGGCTACTCTTTCACCCACCATTGGATCCACT
GGGTGAGGCAGGCTCCTGGACAGGGACTGGAGTGGATGGGCATGATCGACGCTT
CCGATAGCGAGACAAGACTGTCTCAGAAGTTTAAGGACCGCGTGACCATCACAGC
CGATAAGTCTACCTCCACAGCTTACATGGAGCTGTCTTCCCTGAGATCCGAGGACA
CCGCCGTGTACTATTGTGCTAGGCTGGGCCGGTACTATTTCGATTATTGGGGCCAG
GGCACCACAGTGACAGTGAGCTCTGCCAGCACAAAGGGCCCTTCCGTGTTCCCA
CTGGCTCCCTGCTCCAGAAGCACATCTGAGTCCACCGCCGCTCTGGGCTGTCTGG
TGAAGGACTACTTCCCTGAGCCAGTGACCGTGTCCTGGAACAGCGGCGCCCTGAC
ATCTGGCGTGCACACCTTTCCAGCTGTGCTGCAGTCCAGCGGCCTGTACTCCCTGT
CTTCCGTGGTGACAGTGCCCAGCTCTTCCCTGGGCACCAAGACATATACCTGCAA
CGTGGACCATAAGCCTTCCAATACCAAGGTGGATAAGAGGGTGGAGAGCAAGTAC
GGACCACCTTGCCCACCATGTCCAGCTCCTGAGTTTGAGGGAGGACCATCCGTGT
TCCTGTTTCCTCCAAAGCCTAAGGACACCCTGATGATCAGCCGGACACCTGAGGT
GACCTGCGTGGTGGTGGACGTGTCTCAGGAGGATCCAGAGGTGCAGTTCAACTG
GTACGTGGATGGCGTGGAGGTGCACAATGCTAAGACCAAGCCAAGAGAGGAGCA
GTTTAATTCCACATACCGCGTGGTGAGCGTGCTGACCGTGCTGCATCAGGATTGGC
TGAACGGCAAGGAGTATAAGTGCAAGGTGTCCAATAAGGGCCTGCCCAGCTCTAT -continued

CGAGAAGACAATCAGCAAGGCTAAGGGACAGCCTAGGGAGCCACAGGTGTACAC

CCTGCCCCCTTCTCAGGAGGAGATGACAAAGAACCAGGTGTCCCTGACCTGTCTG

GTGAAGGGCTTCTATCCAAGCGACATCGCTGTGGAGTGGGAGTCTAATGGCCAGC

CCGAGAACAATTACAAGACCACACCACCCGTGCTGGACTCTGATGGCTCCTTCTT

TCTGTATTCTAGGCTGACAGTGGATAAGTCCCGGTGGCAGGAGGGCAACGTGTTT

AGCTGCTCTGTGATGCACGAGGCCCTGCACAATCATTATACCCAGAAGTCCCTGAG

CCTGTCTCTGGGCAAGGGTGGAGGCGGTAGTGGAGGCGGTTCAGAGGTGCAGCT

GGTGGAGTCCGGAGGAGGACTGGTGCAGCCAGGAGGCTCCCTGAGGCTGAGCTG

CGCCGCTTCTGGCTACACCGTGTCCAGCTATTGTATGGGCTGGTTCAGGCAGGCTC

CTGGCAAGGGAAGGGAGGGCGTGTCCGCTATCGACAGCGATGGCAGCGTGTCTTA

CGCCGACAGCGTGAAGGGCAGATTCACCATCTCTAAGGATAACTCCAAGAATACA

CTGTACCTGCAGATGAACTCTCTGCGCGCCGAGGACACCGCCGTGTACTTTTGCG

CTGCTGACCTGTGCTGGGTGGACCAGGATCAGGGCGAGTATAATACATGGGGCCA

GGGCACCCTGGTGACAGTGTCTTCC

Amino acid sequence of polypeptide chain H3

(SEQ ID NO: 12)

EVQLVQSGAEVKKPGSSVKVSCKASGYSFTHHWIHWVRQAPGQGLEWMGMID

ASDSETRLSQKFKDRVTITADKSTSTAYMELSSLRSEDTAVYYCARLGRYYPDYWGQ

GTTVTVSSASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPCPP

CPAPEFEGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKGGGGSGGGS

EVQLVESGGGLVQPGGSLRLSCAASGYTVSSYCMGWFRQAPGKGREGVSAIDSDGS

VSYADSVKGRFTISKDNSKNTLYLQMNSLRAEDTAVYFCAADLCWVDQDQGEYNT

WGQGTLVTVSS

DNA sequence of polypeptide chain H4

(SEQ ID NO: 13)

GAGGTGCAGCTGGTGGAGTCCGGAGGAGGACTGGTGCAGCCAGGAGGCTCC

CTGAGGCTGAGCTGCGCCGCTTCTGGCTACACCGTGTCCAGCTATTGTATGGGCTG

GTTCAGGCAGGCTCCTGGCAAGGGAAGGGAGGGCGTGTCCGCTATCGACAGCGA

TGGCAGCGTGTCTTACGCCGACAGCGTGAAGGGCAGATTCACCATCTCTAAGGAT

AACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTA

TAATACATGGGGCCAGGGCACCCTGGTGACAGTGTCTTCCGGTGGAGGCGGTAGT

GGAGGCGGTTCAGAGGTGCAGCTGGTGCAGTCCGGAGCTGAGGTGAAGAAGCCA

GGATCCAGCGTGAAGGTGAGCTGCAAGGCTAGCGGCTACTCTTTCACCCACCATT

GGATCCACTGGGTGAGGCAGGCTCCTGGACAGGGACTGGAGTGGATGGGCATGAT

CGACGCTTCCGATAGCGAGACAAGACTGTCTCAGAAGTTTAAGGACCGCGTGACC

ATCACAGCCGATAAGTCTACCTCCACAGCTTACATGGAGCTGTCTTCCCTGAGATC

CGAGGACACCGCCGTGTACTATTGTGCTAGGCTGGGCCGGTACTATTTCGATTATT

-continued

GGGGCCAGGGCACCACAGTGACAGTGAGCTCTGCCAGCACAAAGGGCCCTTCCG

TGTTCCCACTGGCTCCCTGCTCCAGAAGCACATCTGAGTCCACCGCCGCTCTGGG

CTGTCTGGTGAAGGACTACTTCCCTGAGCCAGTGACCGTGTCCTGGAACAGCGGC

GCCCTGACATCTGGCGTGCACACCTTTCCAGCTGTGCTGCAGTCCAGCGGCCTGT

ACTCCCTGTCTTCCGTGGTGACAGTGCCCAGCTCTTCCCTGGGCACCAAGACATAT

ACCTGCAACGTGGACCATAAGCCTTCCAATACCAAGGTGGATAAGAGGGTGGAGA

GCAAGTACGGACCACCTTGCCCACCATGTCCAGCTCCTGAGTTTGAGGGAGGACC

ATCCGTGTTCCTGTTTCCTCCAAAGCCTAAGGACACCCTGATGATCAGCCGGACAC

CTGAGGTGACCTGCGTGGTGGTGGACGTGTCTCAGGAGGATCCAGAGGTGCAGTT

CAACTGGTACGTGGATGGCGTGGAGGTGCACAATGCTAAGACCAAGCCAAGAGA

GGAGCAGTTTAATTCCACATACCGCGTGGTGAGCGTGCTGACCGTGCTGCATCAG

GATTGGCTGAACGGCAAGGAGTATAAGTGCAAGGTGTCCAATAAGGGCCTGCCCA

GCTCTATCGAGAAGACAATCAGCAAGGCTAAGGGACAGCCTAGGGAGCCACAGG

TGTACACCCTGCCCCCTTCTCAGGAGGAGATGACAAAGAACCAGGTGTCCCTGAC

CTGTCTGGTGAAGGGCTTCTATCCAAGCGACATCGCTGTGGAGTGGGAGTCTAAT

GGCCAGCCCGAGAACAATTACAAGACCACACCACCCGTGCTGGACTCTGATGGCT

CCTTCTTTCTGTATTCTAGGCTGACAGTGGATAAGTCCCGGTGGCAGGAGGGCAAC

GTGTTTAGCTGCTCTGTGATGCACGAGGCCCTGCACAATCATTATACCCAGAAGTC

CCTGAGCCTGTCTCTGGGCAAG

Amino acid sequence of polypeptide chain H4

(SEQ ID NO: 14)

EVQLVESGGGLVQPGGSLRLSCAASGYTVSSYCMGWFRQAPGKGREGVSAIDSD

GSVSYADSVKGRFTISKDNSKNTLYLQMNSLRAEDTAVYFCAADLCWVDQDQGEYN

TWGQGTLVTVSSGGGGSGGGSEVQLVQSGAEVKKPGSSVKVSCKASGYSFTHHWIH

WVRQAPGQGLEWMGMIDASDSETRLSQKFKDRVTITADKSTSTAYMELSSLRSEDTA

VYYCARLGRYYFDYWGQGTTVTVSSASTKGPSVFPLAPCSRSTSESTAALGCLVKDY

FPEPVTVSWNSGALTSGVHTFPAVLQSSGLYSLSSVVTVPSSSLGTKTYTCNVDHKPS

NTKVDKRVESKYGPPCPPCPAPEFEGGPSVFLFPPKPKDTLMISRTPEVTCVVVDVSQ

EDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEALHNHYTQ

KSLSLSLGK

DNA sequence of polypeptide chain L1

(SEQ ID NO: 15)

GAGATCGTGCTGACCCAGTCTCCAGCCACACTGTCTCTGTCCCCAGGAGAGA

GGGCCACCCTGAGCTGCCGGGCTTCTGAGAACGTGGGCACATACATCTCCTGGTA

TCAGCAGAAGCCAGGACAGGCTCCTAGGCTGCTGATCTACGGCGCTAGCAATAGA

TATACCGGCATCCCTGCTCGCTTCAGCGGATCTGGATCCGGCACAGACTTTACCCT

GACAATCTCCAGCCTGGAGCCAGAGGATTTCGCCGTGTACTATTGTGGCGAGTCCT

ACGGCCACCTGTATACCTTTGGCGGCGGCACAAAGGTGGAGATCAAGCGAACGGT

GGCTGCACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGC

-continued

AGGACAGCAAGGACAGCACCTACAGCCTCAGCAGCACCCTGACGCTGAGCAAAG

CAGACTACGAGAAACACAAAGTCTACGCCTGCGAAGTCACCCATCAGGGCCTGA

GCTCGCCCGTCACAAAGAGCTTCAACAGGGGAGAGTGTGAACCTAAGTCTAGCG

ACAAAACTCATACCAGCCCCCCTAGTCCAGAGGTGCAGCTGGTGGAGTCCGGAG

GAGGACTGGTGCAGCCAGGAGGCTCCCTGAGGCTGAGCTGCGCCGCTTCTGGCT

ACACCGTGTCCAGCTATTGTATGGGCTGGTTCAGGCAGGCTCCTGGCAAGGGAAG

GGAGGGCGTGTCCGCTATCGACAGCGATGGCAGCGTGTCTTACGCCGACAGCGTG

AAGGGCAGATTCACCATCTCTAAGGATAACTCCAAGAATACACTGTACCTGCAGAT

GAACTCTCTGCGCGCCGAGGACACCGCCGTGTACTTTTGCGCTGCTGACCTGTGC

TGGGTGGACCAGGATCAGGGCGAGTATAATACATGGGGCCAGGGCACCCTGGTGA

CAGTGTCTTCC

Amino acid sequence of polypeptide chain L1

(SEQ ID NO: 16)

EIVLTQSPATLSLSPGERATLSCRASENVGTYISWYQQKPGQAPRLLIYGASNRYT

GIPARFSGSGSGTDFTLTISSLEPEDFAVYYCGESYGHLYTFGGGTKVEIKRTVAAPSVF

IFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGECEPKSSDKTHTSPPSPEV

QLVESGGGLVQPGGSLRLSCAASGYTVSSYCMGWFRQAPGKGREGVSAIDSDGSVS

YADSVKGRFTISKDNSKNTLYLQMNSLRAEDTAVYFCAADLCWVDQDQGEYNTWG

QGTLVTVSS

DNA sequence of polypeptide chain L2

(SEQ ID NO: 17)

GAGGTGCAGCTGGTGGAGTCCGGAGGAGGACTGGTGCAGCCAGGAGGCTCC

CTGAGGCTGAGCTGCGCCGCTTCTGGCTACACCGTGTCCAGCTATTGTATGGGCTG

GTTCAGGCAGGCTCCTGGCAAGGGAAGGGAGGGCGTGTCCGCTATCGACAGCGA

TGGCAGCGTGTCTTACGCCGACAGCGTGAAGGGCAGATTCACCATCTCTAAGGAT

AACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTA

TAATACATGGGGCCAGGGCACCCTGGTGACAGTGTCTTCCGAACCTAAGTCTAGC

GACAAAACTCATACCAGCCCCCCTAGTCCAGAGATCGTGCTGACCCAGTCTCCAG

CCACACTGTCTCTGTCCCCAGGAGAGAGGGCCACCCTGAGCTGCCGGGCTTCTGA

GAACGTGGGCACATACATCTCCTGGTATCAGCAGAAGCCAGGACAGGCTCCTAGG

CTGCTGATCTACGGCGCTAGCAATAGATATACCGGCATCCCTGCTCGCTTCAGCGG

ATCTGGATCCGGCACAGACTTTACCCTGACAATCTCCAGCCTGGAGCCAGAGGAT

TTCGCCGTGTACTATTGTGGCGAGTCCTACGGCCACCTGTATACCTTTGGCGGCGG

CACAAAGGTGGAGATCAAGCGAACGGTGGCTGCACCATCTGTCTTCATCTTCCCG

CCATCTGATGAGCAGTTGAAATCTGGAACTGCCTCTGTTGTGTGCCTGCTGAATAA

CTTCTATCCCAGAGAGGCCAAAGTACAGTGGAAGGTGGATAACGCCCTCCAATCG

GGTAACTCCCAGGAGAGTGTCACAGAGCAGGACAGCAAGGACAGCACCTACAGC

CTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAAC

AGGGGAGAGTGT

-continued

Amino acid sequence of polypeptide chain L2
(SEQ ID NO: 18)

EVQLVESGGGLVQPGGSLRLSCAASGYTVSSYCMGWFRQAPGKGREGVSAIDSD

GSVSYADSVKGRFTISKDNSKNTLYLQMNSLRAEDTAVYFCAADLCWVDQDQGEYN

TWGQGTLVTVSSEPKSSDKTHTSPPSPEIVLTQSPATLSLSPGERATLSCRASENVGTYI

SWYQQKPGQAPRLLIYGASNRYTGIPARFSGSGSGTDFTLTISSLEPEDFAVYYCGESY

GHLYTFGGGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTK

SFNRGEC

DNA sequence of polypeptide chain L3
(SEQ ID NO: 19)

GAGATCGTGCTGACCCAGTCTCCAGCCACACTGTCTCTGTCCCCAGGAGAGA

GGGCCACCCTGAGCTGCCGGGCTTCTGAGAACGTGGGCACATACATCTCCTGGTA

TCAGCAGAAGCCAGGACAGGCTCCTAGGCTGCTGATCTACGGCGCTAGCAATAGA

TATACCGGCATCCCTGCTCGCTTCAGCGGATCTGGATCCGGCACAGACTTTACCCT

GACAATCTCCAGCCTGGAGCCAGAGGATTTCGCCGTGTACTATTGTGGCGAGTCCT

ACGGCCACCTGTATACCTTTGGCGGCGGCACAAAGGTGGAGATCAAGCGAACGGT

GGCTGCACCATCTGTCTTCATCTTCCCGCCATCTGATGAGCAGTTGAAATCTGGAA

CTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGC

AGGACAGCAAGGACAGCACCTACAGCCTCAGCAGCACCCTGACGCTGAGCAAAG

CAGACTACGAGAAACACAAAGTCTACGCCTGCGAAGTCACCCATCAGGGCCTGA

GCTCGCCCGTCACAAAGAGCTTCAACAGGGGAGAGTGTGGTGGAGGCGGTAGTG

GAGGCGGTTCAGAGGTGCAGCTGGTGGAGTCCGGAGGAGGACTGGTGCAGCCAG

GAGGCTCCCTGAGGCTGAGCTGCGCCGCTTCTGGCTACACCGTGTCCAGCTATTG

TATGGGCTGGTTCAGGCAGGCTCCTGGCAAGGGAAGGGAGGGCGTGTCCGCTATC

GACAGCGATGGCAGCGTGTCTTACGCCGACAGCGTGAAGGGCAGATTCACCATCT

CTAAGGATAACTCCAAGAATACACTGTACCTGCAGATGAACTCTCTGCGCGCCGA

GGACACCGCCGTGTACTTTTGCGCTGCTGACCTGTGCTGGGTGGACCAGGATCAG

GGCGAGTATAATACATGGGGCCAGGGCACCCTGGTGACAGTGTCTTCC

Amino acid sequence of polypeptide chain L3
(SEQ ID NO: 20)

EIVLTQSPATLSLSPGERATLSCRASENVGTYISWYQQKPGQAPRLLIYGASNRYT

GIPARFSGSGSGTDFTLTISSLEPEDFAVYYCGESYGHLYTFGGGTKVEIKRTVAAPSVF

IFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGECGGGGSGGGSEVQLVES

GGGLVQPGGSLRLSCAASGYTVSSYCMGWFRQAPGKGREGVSAIDSDGSVSYADSV

KGRFTISKDNSKNTLYLQMNSLRAEDTAVYFCAADLCWVDQDQGEYNTWGQGTLV

TVSS

DNA sequence of polypeptide chain L4
(SEQ ID NO: 21)

GAGGTGCAGCTGGTGGAGTCCGGAGGAGGACTGGTGCAGCCAGGAGGCTCC

CTGAGGCTGAGCTGCGCCGCTTCTGGCTACACCGTGTCCAGCTATTGTATGGGCTG

GTTCAGGCAGGCTCCTGGCAAGGGAAGGGAGGGCGTGTCCGCTATCGACAGCGA

TGGCAGCGTGTCTTACGCCGACAGCGTGAAGGGCAGATTCACCATCTCTAAGGAT

-continued

AACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTA

TAATACATGGGGCCAGGGCACCCTGGTGACAGTGTCTTCCGGTGGAGGCGGTAGT

GGAGGCGGTTCAGAGATCGTGCTGACCCAGTCTCCAGCCACACTGTCTCTGTCCC

CAGGAGAGAGGGCCACCCTGAGCTGCCGGGCTTCTGAGAACGTGGGCACATACA

TCTCCTGGTATCAGCAGAAGCCAGGACAGGCTCCTAGGCTGCTGATCTACGGCGC

TAGCAATAGATATACCGGCATCCCTGCTCGCTTCAGCGGATCTGGATCCGGCACAG

ACTTTACCCTGACAATCTCCAGCCTGGAGCCAGAGGATTTCGCCGTGTACTATTGT

GGCGAGTCCTACGGCCACCTGTATACCTTTGGCGGCGGCACAAAGGTGGAGATCA

AGCGAACGGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGGC

CAAAGTACAGTGGAAGGTGGATAACGCCCTCCAATCGGGTAACTCCCAGGAGAGT

GTCACAGAGCAGGACAGCAAGGACAGCACCTACAGCCTCAGCAGCACCCTGACG

CTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGT

Amino acid sequence of polypeptide chain L4

(SEQ ID NO: 22)

EVQLVESGGGLVQPGGSLRLSCAASGYTVSSYCMGWFRQAPGKGREGVSAIDSD

GSVSYADSVKGRFTISKDNSKNTLYLQMNSLRAEDTAVYFCAADLCWVDQDQGEYN

TWGQGTLVTVSSGGGGSGGGSEIVLTQSPATLSLSPGERATLSCRASENVGTYISWYQ

QKPGQAPRLLIYGASNRYTGIPARFSGSGSGTDFTLTISSLEPEDFAVYYCGESYGHLY

TFGGGTKVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSPVTKSFNR

GEC

DNA sequence of polypeptide chain H5

(SEQ ID NO: 23)

GAGGTGCAGCTGGTGCAGTCCGGAGCTGAGGTGAAGAAGCCAGGATCCAGC

GTGAAGGTGAGCTGCAAGGCTAGCGGCTACTCTTTCACCCACCATTGGATCCACT

GGGTGAGGCAGGCTCCTGGACAGGGACTGGAGTGGATGGGCATGATCGACGCTT

CCGATAGCGAGACAAGACTGTCTCAGAAGTTTAAGGACCGCGTGACCATCACAGC

CGATAAGTCTACCTCCACAGCTTACATGGAGCTGTCTTCCCTGAGATCCGAGGACA

CCGCCGTGTACTATTGTGCTAGGCTGGGCCGGTACTATTTCGATTATTGGGGCCAG

GGCACCACAGTGACAGTGAGCTCTGCCAGCACAAAGGGCCCTTCCGTGTTCCCA

CTGGCTCCCTGCTCCAGAAGCACATCTGAGTCCACCGCCGCTCTGGGCTGTCTGG

TGAAGGACTACTTCCCTGAGCCAGTGACCGTGTCCTGGAACAGCGGCGCCCTGAC

ATCTGGCGTGCACACCTTTCCAGCTGTGCTGCAGTCCAGCGGCCTGTACTCCCTGT

CTTCCGTGGTGACAGTGCCCAGCTCTTCCCTGGGCACCAAGACATATACCTGCAA

CGTGGACCATAAGCCTTCCAATACCAAGGTGGATAAGAGGGTGGAGAGCAAGTAC

GGACCACCTTGCCCACCATGTCCAGCTCCTGAGTTTGAGGGAGGACCATCCGTGT

TCCTGTTTCCTCCAAAGCCTAAGGACACCCTGATGATCAGCCGGACACCTGAGGT

GACCTGCGTGGTGGTGGACGTGTCTCAGGAGGATCCAGAGGTGCAGTTCAACTG

GTACGTGGATGGCGTGGAGGTGCACAATGCTAAGACCAAGCCAAGAGAGGAGCA

-continued

GTTTAATTCCACATACCGCGTGGTGAGCGTGCTGACCGTGCTGCATCAGGATTGGC

TGAACGGCAAGGAGTATAAGTGCAAGGTGTCCAATAAGGGCCTGCCCAGCTCTAT

CGAGAAGACAATCAGCAAGGCTAAGGGACAGCCTAGGGAGCCACAGGTGTACAC

CCTGCCCCCTTCTCAGGAGGAGATGACAAAGAACCAGGTGTCCCTGACCTGTCTG

GTGAAGGGCTTCTATCCAAGCGACATCGCTGTGGAGTGGGAGTCTAATGGCCAGC

CCGAGAACAATTACAAGACCACACCACCCGTGCTGGACTCTGATGGCTCCTTCTT

TCTGTATTCTAGGCTGACAGTGGATAAGTCCCGGTGGCAGGAGGGCAACGTGTTT

AGCTGCTCTGTGATGCACGAGGCCCTGCACAATCATTATACCCAGAAGTCCCTGAG

CCTGTCTCTGGGCAAGGGTGGAGGCGGTAGTGGAGGCGGTGGTTCAGGCGGAGG

CGGATCTGAGGTGCAGCTGGTGGAGTCCGGAGGAGGACTGGTGCAGCCAGGAGG

CTCCCTGAGGCTGAGCTGCGCCGCTTCTGGCTACACCGTGTCCAGCTATTGTATGG

GCTGGTTCAGGCAGGCTCCTGGCAAGGGAAGGGAGGGCGTGTCCGCTATCGACA

GCGATGGCAGCGTGTCTTACGCCGACAGCGTGAAGGGCAGATTCACCATCTCTAA

GGATAACTCCAAGAATACACTGTACCTGCAGATGAACTCTCTGCGCGCCGAGGAC

ACCGCCGTGTACTTTTGCGCTGCTGACCTGTGCTGGGTGGACCAGGATCAGGGCG

AGTATAATACATGGGGCCAGGGCACCCTGGTGACAGTGTCTTCC

Amino acid sequence of polypeptide chain H5

(SEQ ID NO: 24)

EVQLVQSGAEVKKPGSSVKVSCKASGYSFTHHWIHWVRQAPGQGLEWMGMID

ASDSETRLSQKFKDRVTITADKSTSTAYMELSSLRSEDTAVYYCARLGRYYPDYWGQ

GTTVTVSSASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVESKYGPPCPP

CPAPEFEGGPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGKGGGGSGGGG

SGGGGSEVQLVESGGGLVQPGGSLRLSCAASGYTVSSYCMGWFRQAPGKGREGVSA

IDSDGSVSYADSVKGRFTISKDNSKNTLYLQMNSLRAEDTAVYFCAADLCWVDQDQ

GEYNTWGQGTLVTVSS

DNA sequence of polypeptide chain H6

(SEQ ID NO: 25)

GAGGTGCAGCTGGTGGAGTCCGGAGGAGGACTGGTGCAGCCAGGAGGCTCC

CTGAGGCTGAGCTGCGCCGCTTCTGGCTACACCGTGTCCAGCTATTGTATGGGCTG

GTTCAGGCAGGCTCCTGGCAAGGGAAGGGAGGGCGTGTCCGCTATCGACAGCGA

TGGCAGCGTGTCTTACGCCGACAGCGTGAAGGGCAGATTCACCATCTCTAAGGAT

AACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTA

TAATACATGGGGCCAGGGCACCCTGGTGACAGTGTCTTCCGGTGGAGGCGGTAGT

GGAGGCGGTGGTTCAGGCGGAGGCGGATCTGAGGTGCAGCTGGTGCAGTCCGGA

GCTGAGGTGAAGAAGCCAGGATCCAGCGTGAAGGTGAGCTGCAAGGCTAGCGGC

TACTCTTTCACCCACCATTGGATCCACTGGGTGAGGCAGGCTCCTGGACAGGGAC

TGGAGTGGATGGGCATGATCGACGCTTCCGATAGCGAGACAAGACTGTCTCAGAA

GTTTAAGGACCGCGTGACCATCACAGCCGATAAGTCTACCTCCACAGCTTACATGG

-continued

AGCTGTCTTCCCTGAGATCCGAGGACACCGCCGTGTACTATTGTGCTAGGCTGGGC
CGGTACTATTTCGATTATTGGGGCCAGGGCACCACAGTGACAGTGAGCTCTGCCA
GCACAAAGGGCCCTTCCGTGTTCCCACTGGCTCCCTGCTCCAGAAGCACATCTGA
GTCCACCGCCGCTCTGGGCTGTCTGGTGAAGGACTACTTCCCTGAGCCAGTGACC
GTGTCCTGGAACAGCGGCGCCCTGACATCTGGCGTGCACACCTTTCCAGCTGTGC
TGCAGTCCAGCGGCCTGTACTCCCTGTCTTCCGTGGTGACAGTGCCCAGCTCTTCC
CTGGGCACCAAGACATATACCTGCAACGTGGACCATAAGCCTTCCAATACCAAGG
TGGATAAGAGGGTGGAGAGCAAGTACGGACCACCTTGCCCACCATGTCCAGCTCC
TGAGTTTGAGGGAGGACCATCCGTGTTCCTGTTTCCTCCAAAGCCTAAGGACACC
CTGATGATCAGCCGGACACCTGAGGTGACCTGCGTGGTGGTGGACGTGTCTCAGG
AGGATCCAGAGGTGCAGTTCAACTGGTACGTGGATGGCGTGGAGGTGCACAATGC
TAAGACCAAGCCAAGAGAGGAGCAGTTTAATTCCACATACCGCGTGGTGAGCGTG
CTGACCGTGCTGCATCAGGATTGGCTGAACGGCAAGGAGTATAAGTGCAAGGTGT
CCAATAAGGGCCTGCCCAGCTCTATCGAGAAGACAATCAGCAAGGCTAAGGGACA
GCCTAGGGAGCCACAGGTGTACACCCTGCCCCCTTCTCAGGAGGAGATGACAAA
GAACCAGGTGTCCCTGACCTGTCTGGTGAAGGGCTTCTATCCAAGCGACATCGCT
GTGGAGTGGGAGTCTAATGGCCAGCCCGAGAACAATTACAAGACCACACCACCC
GTGCTGGACTCTGATGGCTCCTTCTTTCTGTATTCTAGGCTGACAGTGGATAAGTC
CCGGTGGCAGGAGGGCAACGTGTTTAGCTGCTCTGTGATGCACGAGGCCCTGCAC
AATCATTATACCCAGAAGTCCCTGAGCCTGTCTCTGGGCAAG

Amino acid sequence of polypeptide chain H6

(SEQ ID NO: 26)

EVQLVESGGGLVQPGGSLRLSCAASGYTVSSYCMGWFRQAPGKGREGVSAIDSD
GSVSYADSVKGRFTISKDNSKNTLYLQMNSLRAEDTAVYFCAADLCWVDQDQGEYN
TWGQGTLVTVSSGGGGSGGGGSGGGGSEVQLVQSGAEVKKPGSSVKVSCKASGYSF
THHWIHWVRQAPGQGLEWMGMIDASDSETRLSQKFKDRVTITADKSTSTAYMELSS
LRSEDTAVYYCARLGRYYFDYWGQGTTVTVSSASTKGPSVFPLAPCSRSTSESTAAL
GCLVKDYFPEPVTVSWNSGALTSGVHTFPAVLQSSGLYSLSSVVTVPSSSLGTKTYTC
NVDHKPSNTKVDKRVESKYGPPCPPCPAPEFEGGPSVFLFPPKPKDTLMISRTPEVTCV
VVDVSQEDPEVQFNWYVDGVEVHNAKTKPREEQFNSTYRVVSVLTVLHQDWLNGK
EYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEAL
HNHYTQKSLSLSLGK

DNA sequence of polypeptide chain L5

(SEQ ID NO: 27)

GAGATCGTGCTGACCCAGTCTCCAGCCACACTGTCTCTGTCCCCAGGAGAGA
GGGCCACCCTGAGCTGCCGGGCTTCTGAGAACGTGGGCACATACATCTCCTGGTA
TCAGCAGAAGCCAGGACAGGCTCCTAGGCTGCTGATCTACGGCGCTAGCAATAGA
TATACCGGCATCCCTGCTCGCTTCAGCGGATCTGGATCCGGCACAGACTTTACCCT
GACAATCTCCAGCCTGGAGCCAGAGGATTTCGCCGTGTACTATTGTGGCGAGTCCT
ACGGCCACCTGTATACCTTTGGCGGCGGCACAAAGGTGGAGATCAAGCGAACGGT
GGCTGCACCATCTGTCTTCATCTTCCCGCCATCTGATGAGCAGTTGAAATCTGGAA

-continued

CTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGC

AGGACAGCAAGGACAGCACCTACAGCCTCAGCAGCACCCTGACGCTGAGCAAAG

CAGACTACGAGAAACACAAAGTCTACGCCTGCGAAGTCACCCATCAGGGCCTGA

GCTCGCCCGTCACAAAGAGCTTCAACAGGGGAGAGTGTGGTGGAGGCGGTAGTG

GAGGCGGTGGTTCAGGCGGAGGCGGATCTGAGGTGCAGCTGGTGGAGTCCGGAG

GAGGACTGGTGCAGCCAGGAGGCTCCCTGAGGCTGAGCTGCGCCGCTTCTGGCT

ACACCGTGTCCAGCTATTGTATGGGCTGGTTCAGGCAGGCTCCTGGCAAGGGAAG

GGAGGGCGTGTCCGCTATCGACAGCGATGGCAGCGTGTCTTACGCCGACAGCGTG

AAGGGCAGATTCACCATCTCTAAGGATAACTCCAAGAATACACTGTACCTGCAGAT

GAACTCTCTGCGCGCCGAGGACACCGCCGTGTACTTTTGCGCTGCTGACCTGTGC

TGGGTGGACCAGGATCAGGGCGAGTATAATACATGGGGCCAGGGCACCCTGGTGA

CAGTGTCTTCC

Amino acid sequence of polypeptide chain L5

(SEQ ID NO: 28)

EIVLTQSPATLSLSPGERATLSCRASENVGTYISWYQQKPGQAPRLLIYGASNRYT

GIPARFSGSGSGTDFTLTISSLEPEDFAVYYCGESYGHLYTFGGGTKVEIKRTVAAPSVF

IFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGECGGGGSGGGGSGGGGSE

VQLVESGGGLVQPGGSLRLSCAASGYTVSSYCMGWFRQAPGKGREGVSAIDSDGSV

SYADSVKGRFTISKDNSKNTLYLQMNSLRAEDTAVYFCAADLCWVDQDQGEYNTW

GQGTLVTVSS

DNA sequence of polypeptide chain L6

(SEQ ID NO: 29)

GAGGTGCAGCTGGTGGAGTCCGGAGGAGGACTGGTGCAGCCAGGAGGCTCC

CTGAGGCTGAGCTGCGCCGCTTCTGGCTACACCGTGTCCAGCTATTGTATGGGCTG

GTTCAGGCAGGCTCCTGGCAAGGGAAGGGAGGGCGTGTCCGCTATCGACAGCGA

TGGCAGCGTGTCTTACGCCGACAGCGTGAAGGGCAGATTCACCATCTCTAAGGAT

AACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTA

TAATACATGGGGCCAGGGCACCCTGGTGACAGTGTCTTCCGGTGGAGGCGGTAGT

GGAGGCGGTGGTTCAGGCGGAGGCGGATCTGAGATCGTGCTGACCCAGTCTCCA

GCCACACTGTCTCTGTCCCCAGGAGAGAGGGCCACCCTGAGCTGCCGGGCTTCTG

AGAACGTGGGCACATACATCTCCTGGTATCAGCAGAAGCCAGGACAGGCTCCTAG

GCTGCTGATCTACGGCGCTAGCAATAGATATACCGGCATCCCTGCTCGCTTCAGCG

GATCTGGATCCGGCACAGACTTTACCCTGACAATCTCCAGCCTGGAGCCAGAGGA

TTTCGCCGTGTACTATTGTGGCGAGTCCTACGGCCACCTGTATACCTTTGGCGGCG

GCACAAAGGTGGAGATCAAGCGAACGGTGGCTGCACCATCTGTCTTCATCTTCCC

GCCATCTGATGAGCAGTTGAAATCTGGAACTGCCTCTGTTGTGTGCCTGCTGAATA

ACTTCTATCCCAGAGAGGCCAAAGTACAGTGGAAGGTGGATAACGCCCTCCAATC

GGGTAACTCCCAGGAGAGTGTCACAGAGCAGGACAGCAAGGACAGCACCTACAG

-continued

CCTCAGCAGCACCCTGACGCTGAGCAAAGCAGACTACGAGAAACACAAAGTCTA

CGCCTGCGAAGTCACCCATCAGGGCCTGAGCTCGCCCGTCACAAAGAGCTTCAAC

AGGGGAGAGTGT

Amino acid sequence of polypeptide chain L6

(SEQ ID NO: 30)

EVQLVESGGGLVQPGGSLRLSCAASGYTVSSYCMGWFRQAPGKGREGVSAIDSD

GSVSYADSVKGRFTISKDNSKNTLYLQMNSLRAEDTAVYFCAADLCWVDQDQGEYN

TWGQGTLVTVSSGGGGSGGGGSGGGGSEIVLTQSPATLSLSPGERATLSCRASENVGT

YISWYQQKPGQAPRLLIYGASNRYTGIPARFSGSGSGTDFTLTISSLEPEDFAVYYCGE

SYGHLYTFGGGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPV

TKSFNRGEC

DNA sequence of polypeptide chain H7

(SEQ ID NO: 31)

GAGGTGCAGCTGGTGGAGTCCGGAGGAGGACTGGTGCAGCCAGGAGGCTCC

CTGAGGCTGAGCTGCGCCGCTTCTGGCTACACCGTGTCCAGCTATTGTATGGGCTG

GTTCAGGCAGGCTCCTGGCAAGGGAAGGGAGGGCGTGTCCGCTATCGACAGCGA

TGGCAGCGTGTCTTACGCCGACAGCGTGAAGGGCAGATTCACCATCTCTAAGGAT

AACTCCAAGAATACACTGTACCTGCAGATGAACTCTCTGCGCGCCGAGGACACCG

CCGTGTACTTTTGCGCTGCTGACCTGTGCTGGGTGGACCAGGATCAGGGCGAGTA

TAATACATGGGGCCAGGGCACCCTGGTGACAGTGTCTTCCGAGAGCAAGTACGGA

CCACCTTGCCCACCATGTCCAGCTCCTGAGTTTGAGGGAGGACCATCCGTGTTCCT

GTTTCCTCCAAAGCCTAAGGACACCCTGATGATCAGCCGGACACCTGAGGTGACC

TGCGTGGTGGTGGACGTGTCTCAGGAGGATCCAGAGGTGCAGTTCAACTGGTACG

TGGATGGCGTGGAGGTGCACAATGCTAAGACCAAGCCAAGAGAGGAGCAGTTTA

ATTCCACATACCGCGTGGTGAGCGTGCTGACCGTGCTGCATCAGGATTGGCTGAA

CGGCAAGGAGTATAAGTGCAAGGTGTCCAATAAGGGCCTGCCCAGCTCTATCGAG

AAGACAATCAGCAAGGCTAAGGGACAGCCTAGGGAGCCACAGGTGTACACCCTG

CCCCCTTCTCAGGAGGAGATGACAAAGAACCAGGTGTCCCTGACCTGTCTGGTGA

AGGGCTTCTATCCAAGCGACATCGCTGTGGAGTGGGAGTCTAATGGCCAGCCCGA

GAACAATTACAAGACCACACCACCCGTGCTGGACTCTGATGGCTCCTTCTTTCTGT

ATTCTAGGCTGACAGTGGATAAGTCCCGGTGGCAGGAGGGCAACGTGTTTAGCTG

CTCTGTGATGCACGAGGCCCTGCACAATCATTATACCCAGAAGTCCCTGAGCCTGT

CTCTGGGCAAG

Amino acid sequence of polypeptide chain H7

(SEQ ID NO: 32)

EVQLVESGGGLVQPGGSLRLSCAASGYTVSSYCMGWFRQAPGKGREGVSAIDSD

GSVSYADSVKGRFTISKDNSKNTLYLQMNSLRAEDTAVYFCAADLCWVDQDQGEYN

TWGQGTLVTVSSESKYGPPCPPCPAPEFEGGPSVFLFPPKPKDTLMISRTPEVTCVVVD

VSQEDPEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVMHEALHNH

YTQKSLSLSLGK

TABLE 4

Linker sequences and IgG4-Fc sequences

| | Sequence | SEQ ID NO: |
|---|---|---|
| DNA sequence of E-Linker | GAACCTAAGTCTAGCGACAAAACTCATACCAGCCC CCCTAGTCCA | 44 |
| Amino acid sequence of E-Linker | EPKSSDKTHTSPPSP | 45 |
| DNA sequence of G15-Linker | GGTGGAGGCGGTAGTGGAGGCGGTGGTTCAGGCG GAGGCGGATCT | 46 |
| Amino acid sequence of G15-Linker | GGGGSGGGGSGGGGS | 47 |
| DNA sequence of G9-Linker | GGTGGAGGCGGTAGTGGAGGCGGTTCA | 48 |
| Amino acid sequence of G9-Linker | GGGGSGGGS | 49 |
| DNA sequence of IgG4 Fc | GAGAGCAAGTACGGACCACCTTGCCCACCATGTCC AGCTCCTGAGTTTGAGGGAGGACCATCCGTGTTCC TGTTTCCTCCAAAGCCTAAGGACACCCTGATGATCA GCCGGACACCTGAGGTGACCTGCGTGGTGGTGGAC GTGTCTCAGGAGGATCCAGAGGTGCAGTTCAACTG GTACGTGGATGGCGTGGAGGTGCACAATGCTAAGA CCAAGCCAAGAGAGGAGCAGTTTAATTCCACATAC CGCGTGGTGAGCGTGCTGACCGTGCTGCATCAGGA TTGGCTGAACGGCAAGGAGTATAAGTGCAAGGTGT CCAATAAGGGCCTGCCCAGCTCTATCGAGAAGACA ATCAGCAAGGCTAAGGGACAGCCTAGGGAGCCAC AGGTGTACACCCTGCCCCCTTCTCAGGAGGAGATG ACAAAGAACCAGGTGTCCCTGACCTGTCTGGTGAA GGGCTTCTATCCAAGCGACATCGCTGTGGAGTGGG AGTCTAATGGCCAGCCCGAGAACAATTACAAGACC ACACCACCCGTGCTGGACTCTGATGGCTCCTTCTTT CTGTATTCTAGGCTGACAGTGGATAAGTCCCGGTGG CAGGAGGGCAACGTGTTTAGCTGCTCTGTGATGCA CGAGGCCCTGCACAATCATTATACCCAGAAGTCCCT GAGCCTGTCTCTGGGCAAG | 50 |
| Amino acid sequence of IgG4 Fc | ESKYGPPCPPCPAPEPEGGPSVFLFPPKPKDTLMISRTP EVTCVVVDVSQEDPEVQFNWYVDGVEVHNAKTKPR EEQFNSTYRVVSVLTVLHQDWLNGKEYKCKVSNKG LPSSIEKTISKAKGQPREPQVYTLPPSQEEMTKNQVSL TCLVKGFYPSDIAVEWESNGQPENNYKTTPPVLDSDG SFFLYSRLTVDKSRWQEGNVFSCSVMHEALHNHYTQ KSLSLSLGK | 51 |

Example 2 FACS Affinity Analysis

For the constructed series of bispecific antibodies, the affinity of these samples with antigens was measured by using a flow cytometer. A sample with an initial concentration of 300 nM undergone serial dilution by 3 times, and then the affinities between samples with different concentrations and LAG-3 antigens or CD47 antigens expressed on CHO-K1 cells were separately tested. Then, an antibody-antigen binding curve was generated based on the geometric mean, raw data of four parameters was plotted by using the GRAPHPAD Prism V6.02 software, and a best fitted value program was compiled to analyze $EC_{50}$.

Figure 2:
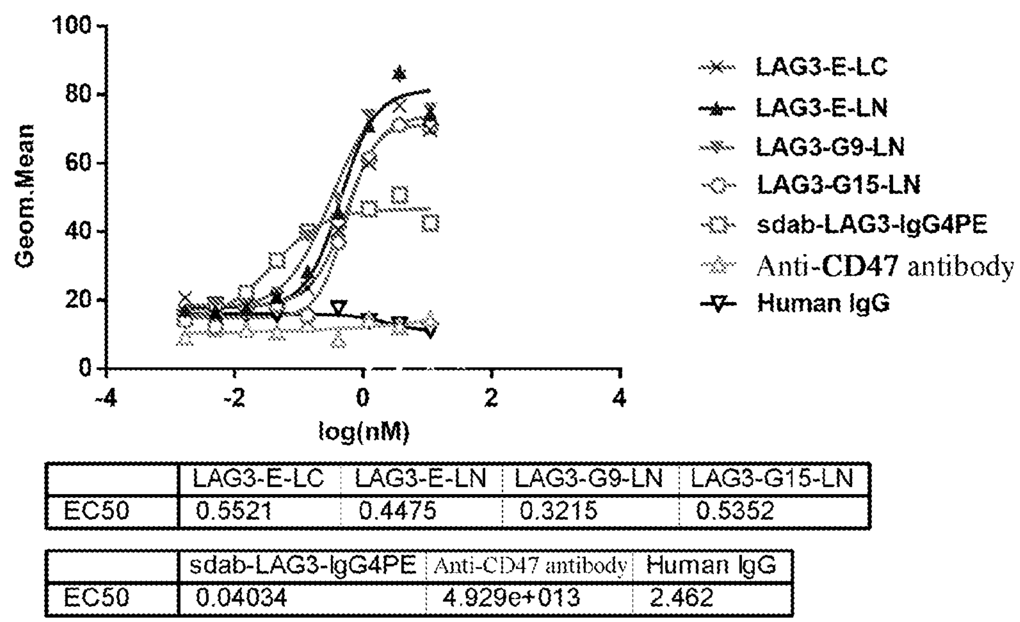
FIG. 2 shows the affinity between a sample and CHO-K1 cells expressing human LAG-3 measured by a flow cytometer.

For the affinity analysis of the LAG-3 antigen, after the bispecific antibody produced when the LAG-3 sdAb was fused to the N-terminus or C-terminus of the heavy chain or light chain of the anti-CD47 mAb was incubated on the CHO-K1 cells expressing the LAG-3 antigen, it was found through FACS detection that, considering the $EC_{50}$ value and the Y-axis response value, compared with a control of the LAG-3 sdAb fused to IgG4 Fc (sdAb-LAG3-IgG4PE), the affinity between all bispecific antibodies and the LAG-3 antigen was significantly higher than that of the sdAb control (shown in FIG. 1 and FIG. 2). The affinity between the LAG-3 antigen and the bispecific antibody that was produced when the LAG-3 sdAb was fused to the C-terminus of the heavy chain of the anti-CD47 mAb was slightly higher than the affinity between the LAG-3 antigen and the bispecific antibody that was produced when the sdAb was fused to the N-terminus of the heavy chain of the anti-CD47 mAb (shown in FIG. 1). The affinity between the LAG-3 antigen and the bispecific antibody that was produced when the LAG-3 sdAb was fused to the N-terminus of the light chain of the anti-CD47 mAb was close to the affinity between the LAG-3 antigen and the bispecific antibody that was produced when the sdAb was fused to the C-terminus of the light chain of the anti-CD47 mAb (shown in FIG. 2). Therefore, no matter which terminus of the heavy or light chain of the anti-CD47 mAb the LAG-3 sdAb is fused to, it will enhance the binding of the LAG-3 sdAb to the LAG-3 antigen. More importantly, when the LAG-3 sdAb is linked to the C-terminus of the heavy or light chain of the anti-CD47 mAb, it will further enhance the affinity between the LAG-3 sdAb and the LAG-3 antigen.

Figure 3:
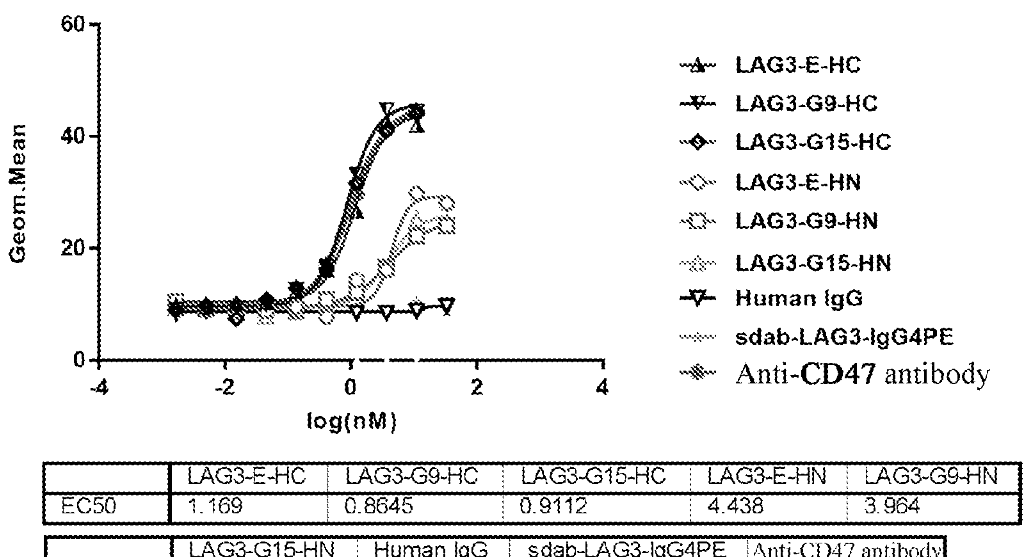
FIG. 3 shows the affinity between a sample and CHO-K1 cells expressing human CD47 measured by a flow cytometer.
Figure 4:
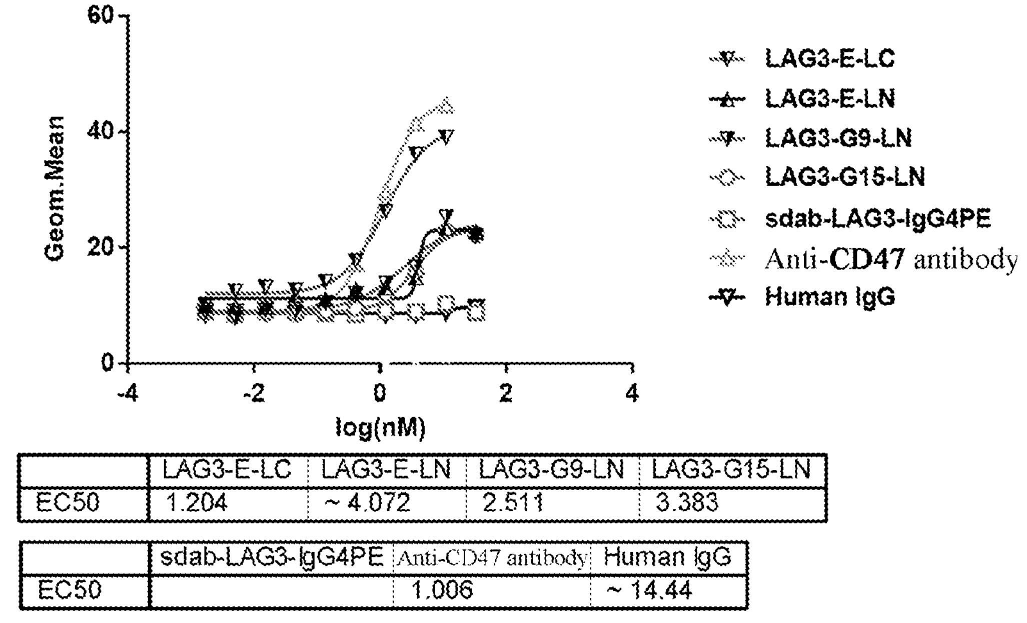
FIG. 4 shows the affinity between a sample and CHO-K1 cells expressing human CD47 measured by a flow cytometer.

For the affinity analysis of the CD47 antigen, after the bispecific antibody produced when the LAG-3 sdAb was fused to the N-terminus or C-terminus of the heavy or light chain of the anti-CD47 mAb was incubated on the CHO-K1 cells expressing the CD47 antigen, it was found through FACS detection that the affinity between the CD47 antigen and the bispecific antibody that was produced when the LAG-3 sdAb was fused to the C-terminus of the heavy chain or light chain of the anti-CD47 mAb was similar to the affinity between the CD47 antigen and the anti-CD47 mAb (shown in FIG. 3 and FIG. 4). The affinity between the CD47 antigen and the bispecific antibody that was produced when the LAG-3 sdAb was fused to the N-terminus of the heavy chain or light chain of the anti-CD47 mAb was significantly lower than the affinity between the CD47 antigen and the control of the anti-CD47 mAb (shown in FIG. 3). Therefore, linking the LAG-3 sdAb to the C-terminus of the anti-CD47 mAb maintains the binding of the anti-CD47 antibody to the CD47 antigen, and linking the LAG-3 sdAb to the N-terminus of the anti-CD47 mAb reduces the affinity between the CD47 antibody and the CD47 antigen.

Example 3 Biological Activity Measurement In Vitro

For the biological activity measurement in vitro of the anti-CD47/anti-LAG-3 bispecific antibody, there is no analytical system that can detect both CD47 and LAG-3 blockers at the same time. Therefore, the bioassay of the LAG-3 blocker is carried out by using the Promega test kit, and then the activity of the bispecific antibody is tested through a cell phagocytosis experiment of the anti-CD47 antibody.

The Promega LAG-3 blocking function reporter gene kit (LAGS Blockade Bioassay, Promega kit product number CS194804) is used in the experiment for testing the in vitro function of anti-LAG-3 mAb samples. The kit detection system consists of two genetically engineered cell lines. The stimulating cell line is aAPC/Raji cells, which express MHCII and can activate the TCR complex. The effector cell line is the Jurkat T cell line, which expresses human LAG3 and a luciferase reporter gene driven by a natural promoter that responds to TCR activation. When the two types of cells are co-cultured, LAG-3 inhibits MHCII activation and promoter-mediated luminescence. The addition of the anti-LAG-3 antibody can block the interaction between LAG3 and MHCII, thereby restoring promoter-mediated chemiluminescence.

The effector cell line Jurkat T cells were first plated in a 96-well plate, and the anti-CD47/anti-LAG-3 bispecific antibody sample and the stimulating cell line aAPC/Raji cells were then added. The resulting system was incubated at 37° C. for 6 h. Next, the Bio-Glo™ fluorescence detection reagent was added to the system, and then the system was incubated for 5-10 min at room temperature. Finally, fluorescence signals in the 96-well plate were read by using a chemical fluorescence signal plate reader. The experiment used the form of eight concentrations and triplicated wells, used the relative fluorescence value as the y-axis, and used the concentration of antibody samples as the x-axis, to plot a four-parameter curve. The curve was analyzed by using the GraphPad Prism software to obtain the $EC_{50}$ value of the anti-CD47/anti-LAG-3 bispecific antibody sample.

For the cell phagocytosis experiment of the anti-CD47 antibody, PBMCs were first extracted from human peripheral blood by the concentration gradient method. Monocytes were then isolated from the PBMCs by using the whole monocyte isolation kit (Miltenyi Biotech). These monocytes were stimulated into macrophages with GM-CSF within 14 days. On day 14, HL60 cells were stained with the PKH26 dye and then seeded in a 96-well culture plate, the monocyte-derived macrophage (MDM) was digested from a Petri dish by using Accutase and then added into the culture plate in which HL60 cells stained with PKH26 were seeded, then the anti-CD47/anti-LAG-3 bispecific antibody sample after serial dilution was added, and incubated at 37° C. for 1 h to carry out the cell phagocytosis reaction. One hour later, MDM was digested from the cell culture plate and stained with the fluorescently labeled anti-CD11b antibody. The cells in the cell culture plate were then analyzed by using the BD FACSCalibur flow cytometer. The phagocytic percentage was calculated by dividing the number of PKH26 and CD11b double-positive cells by the number of PKH26 single-positive cells. A dose-response curve used the phagocytic percentage as the y-axis and used the concentration of the anti-CD47/anti-LAG-3 bispecific antibody as the x-axis, and the GraphPad Prism software was used for analysis to obtain the $EC_{50}$ value and other curve parameters.

Figure 5:
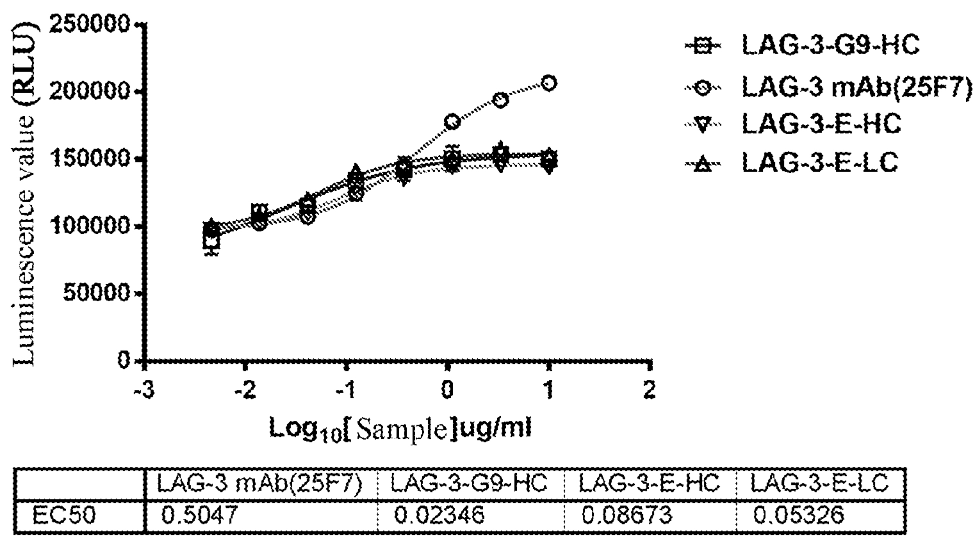
FIG. 5 shows the LAG-3 blocking activity of a sample measured by a LAG-3 blocking bioassay system.

It was indicated based on the biological activity measurement result of the LAG-3 blocker that the biological activities of the three bispecific antibodies LAGS-G9-HC, LAG3-E-HC, and LAG3-E-LC were similar (shown in FIG. 5), although the biological activities of these three bispecific antibodies were lower than the biological activity of the reference antibody 25F7.

Figure 6:
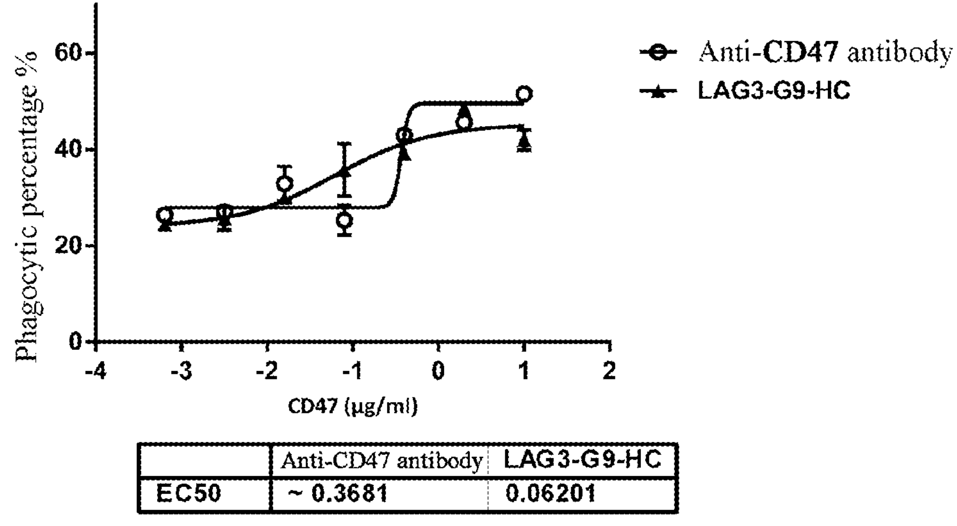
FIG. 6 shows the activity of the bispecific antibody LAG-3-G9-HC tested by a cell phagocytosis experiment of the anti-CD47 antibody.

It was indicated based on the cell phagocytosis experiment result of the anti-CD47 antibody that the $EC_{50}$ value of the bispecific antibody LAGS-G9-HC was significantly lower than that of the anti-CD47 antibody control (shown in FIG. 6), indicated that the biological activity of the bispecific antibody was higher than that of the anti-CD47 antibody control.

What is claimed is:

1. An isolated anti-CD47/anti-LAG-3 bispecific antigen-binding protein or a fragment thereof, comprising (a) a first antigen binding portion comprising a heavy chain variable region ($V_H$) and a light chain variable region ($V_L$), wherein the $V_H$ and $V_L$ form an antigen binding site that specifically binds to CD47; and (b) a second antigen binding portion comprising a single-domain antibody (sdAb) that specifically binds to LAG-3, wherein the first antigen binding portion and the second antigen binding portion are fused to each other;

wherein the $V_H$ of the first antigen binding portion comprises heavy chain CDRs HCDR1, HCDR2, and HCDR3 whose amino acid sequences are set forth in SEQ ID NO:33, SEQ ID NO:34, and SEQ ID NO:35, respectively, and the $V_L$ of the first antigen binding portion comprises light chain CDRs LCDR1, LCDR2, and LCDR3 whose amino acid sequences are set forth in SEQ ID NO:36, SEQ ID NO:37, and SEQ ID NO:38, respectively, and wherein the sdAb of the second antigen binding portion comprises CDRs CDR1, CDR2, and CDR3, amino acid sequences of the CDRs CDR1, CDR2, and CDR3 are respectively as set forth in SEQ ID NO:41, SEQ ID NO:42, and SEQ ID NO:43;

wherein the first antigen binding portion is a full-length antibody comprising two heavy chains and two light chains, the heavy chain comprises $V_H$, and the light chain comprises $V_L$, and the N-terminus of the second antigen binding portion is fused to the C-terminus of at least one heavy chain of the first antigen binding portion or the C-terminus of at least one light chain of the first antigen binding portion.

2. The bispecific antigen-binding protein or the fragment thereof according to claim 1, wherein the first antigen binding portion and the second antigen binding portion are fused by a peptide bond or a peptide linker.

3. The bispecific antigen-binding protein or the fragment thereof according to claim 2, wherein the peptide linker is selected from a mutated human IgG1 hinge region or a GS linker.

4. The bispecific antigen-binding protein or the fragment thereof according to claim 1, wherein the heavy chain of the first antigen binding portion comprises a sequence that is at least 95% identical to the amino acid sequence as set forth in SEQ ID NO:4, and the light chain of the first antigen binding portion comprises a sequence that is at least 95% identical to the amino acid sequence as set forth in SEQ ID NO:6.

5. The bispecific antigen-binding protein or the fragment thereof according to claim 1, wherein the second antigen binding portion comprises a sequence that is at least 95% identical to the amino acid sequence as set forth in SEQ ID NO:40.

6. The bispecific antigen-binding protein or the fragment thereof according to claim 1, wherein the first antigen binding portion comprises a humanized, or chimeric antibody or a fragment thereof, and the sdAb of the second antigen binding portion is a camelid, chimeric, humanized, or human antibody.

7. The bispecific antigen-binding protein or the fragment thereof according to claim 1, comprising an anti-CD47 antibody and an anti-LAG-3 sdAb, with the N-terminus of the anti-LAG-3 sdAb fused to the C-terminus of two heavy chains of the anti-CD47 antibody, wherein the heavy chain fusion polypeptide comprises a sequence that is at least 95% identical to the amino acid sequence as set forth in SEQ ID NO:8, SEQ ID NO: 12, or SEQ ID NO:24, and the light chain polypeptide comprises a sequence that is at least 95% identical to the amino acid sequence as set forth in SEQ ID NO:6; or the N-terminus of the anti-LAG-3 sdAb fused to the C-terminus of two light chains of the anti-CD47 antibody, wherein the light chain fusion polypeptide comprises a sequence that is at least 95% identical to the amino acid sequence as set forth in SEQ ID NO:16, SEQ ID NO:20, or SEQ ID NO:28, and the heavy chain polypeptide comprises a sequence that is at least 95% identical to the amino acid sequence as set forth in SEQ ID NO:4.

8. An isolated polynucleotide encoding the anti-CD47/anti-LAG-3 bispecific antigen-binding protein or the fragment thereof according to claim 1.

9. A vector comprising the isolated polynucleotide according to claim 8.

10. A host cell comprising the isolated polynucleotide according to claim 8.

11. A method for producing an isolated anti-CD47/anti-LAG-3 bispecific antigen-binding protein or a fragment thereof, comprising culturing the host cell according to claim 10 under proper conditions, and recovering an antibody or a fragment thereof from the cell or a cell culture medium.

12. A pharmaceutical composition, comprising the bispecific antigen-binding protein or the fragment thereof according to claim 1, and a pharmaceutically acceptable carrier.

13. A method of treating diseases related to abnormal expression of CD47 and/or LAG-3, comprising administering to a subject in need thereof an effective amount of the bispecific antigen-binding protein or the fragment thereof according to claim 1.

14. The method according to claim 13, wherein the diseases related to abnormal expression of CD47 and/or LAG-3 are cancers.

15. The method according to claim 14, wherein the cancers comprise lymphoma, melanoma, pancreatic cancer, non-small cell lung cancer, breast cancer, stomach cancer, colorectal cancer, head and neck cancer, hepatocellular carcinoma, ovarian cancer, and prostate cancer.

16. The bispecific antigen-binding protein or the fragment thereof according to claim 8, wherein an amino acid sequence of the peptide linker is as set forth in SEQ ID NO: 45, SEQ ID NO:47, or SEQ ID NO:49.

* * * * *

SEQUENCE LISTING

```
<160> NUMBER OF SEQ ID NOS: 51

<210> SEQ ID NO 1
<211> LENGTH: 57
<212> TYPE: DNA
<213> ORGANISM: Artificial Sequence
<220> FEATURE:
<223> OTHER INFORMATION: DNA sequence of secretion signal peptide
```

<400> SEQUENCE: 1
atgggctggt cctgcatcat cctgttcctg gtggctaccg ccaccggcgt gcactcc 57

<210> SEQ ID NO 2
<211> LENGTH: 19
<212> TYPE: PRT
<213> ORGANISM: Artificial Sequence
<220> FEATURE:
<223> OTHER INFORMATION: Amino acid sequence of secretion signal peptide

<400> SEQUENCE: 2

Met Gly Trp Ser Cys Ile Ile Leu Phe Leu Val Ala Thr Ala Thr Gly
1 5 10 15

Val His Ser

<210> SEQ ID NO 3
<211> LENGTH: 1332
<212> TYPE: DNA
<213> ORGANISM: Artificial Sequence
<220> FEATURE:
<223> OTHER INFORMATION: DNA sequence of polypeptide chain H0

<400> SEQUENCE: 3
gaggtgcagc tggtgcagtc cggagctgag gtgaagaagc caggatccag cgtgaaggtg 60
agctgcaagg ctagcggcta ctctttcacc caccattgga tccactgggt gaggcaggct 120
cctggacagg gactggagtg gatgggcatg atcgacgctt ccgatagcga gacaagactg 180
tctcagaagt ttaaggaccg cgtgaccatc acagccgata agtctacctc cacagcttac 240
atggagctgt cttccctgag atccgaggac accgccgtgt actattgtgc taggctgggc 300
cggtactatt tcgattattg gggccagggc accacagtga cagtgagctc tgccagcaca 360
aagggccctt ccgtgttccc actggctccc tgctccagaa gcacatctga gtccaccgcc 420
gctctgggct gtctggtgaa ggactacttc cctgagccag tgaccgtgtc ctggaacagc 480
ggcgccctga catctggcgt gcacaccttt ccagctgtgc tgcagtccag cggcctgtac 540
tccctgtctt ccgtggtgac agtgcccagc tcttccctgg gcaccaagac atatacctgc 600
aacgtggacc ataagccttc caataccaag gtggataaga gggtggagag caagtacgga 660
ccaccttgcc caccatgtcc agctcctgag tttgagggag gaccatccgt gttcctgttt 720
cctccaaagc ctaaggacac cctgatgatc agccggacac ctgaggtgac ctgcgtggtg 780
gtggacgtgt ctcaggagga tccagaggtg cagttcaact ggtacgtgga tggcgtggag 840
gtgcacaatg ctaagaccaa gccaagagag gagcagttta attccacata ccgcgtggtg 900
agcgtgctga ccgtgctgca tcaggattgg ctgaacggca aggagtataa gtgcaaggtg 960
tccaataagg gcctgcccag ctctatcgag aagacaatca gcaaggctaa gggacagcct 1020
agggagccac aggtgtacac cctgccccct tctcaggagg agatgacaaa gaaccaggtg 1080
tccctgacct gtctggtgaa gggcttctat ccaagcgaca tcgctgtgga gtgggagtct 1140
aatggccagc ccgagaacaa ttacaagacc acaccacccg tgctggactc tgatggctcc 1200
ttctttctgt attctaggct gacagtggat aagtcccggt ggcaggaggg caacgtgttt 1260
agctgctctg tgatgcacga ggccctgcac aatcattata cccagaagtc cctgagcctg 1320
tctctgggca ag 1332

<210> SEQ ID NO 4
<211> LENGTH: 444

```
<212> TYPE: PRT
<213> ORGANISM: Artificial Sequence
<220> FEATURE:
<223> OTHER INFORMATION: Amino acid sequence of polypeptide chain H0

<400> SEQUENCE: 4

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
            20                  25                  30

Trp Ile His Trp Val Arg Gln Ala Pro Gly Gln Gly Leu Glu Trp Met
        35                  40                  45

Gly Met Ile Asp Ala Ser Asp Ser Glu Thr Arg Leu Ser Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380
```

```
Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 5
<211> LENGTH: 642
<212> TYPE: DNA
<213> ORGANISM: Artificial Sequence
<220> FEATURE:
<223> OTHER INFORMATION: DNA sequence of polypeptide chain L0

<400> SEQUENCE: 5

gagatcgtgc tgacccagtc tccagccaca ctgtctctgt ccccaggaga gagggccacc     60

ctgagctgcc gggcttctga gaacgtgggc acatacatct cctggtatca gcagaagcca    120

ggacaggctc ctaggctgct gatctacggc gctagcaata gatataccgg catccctgct    180

cgcttcagcg gatctggatc cggcacagac tttaccctga caatctccag cctggagcca    240

gaggatttcg ccgtgtacta ttgtggcgag tcctacggcc acctgtatac ctttggcggc    300

ggcacaaagg tggagatcaa gcgaacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 6
<211> LENGTH: 214
<212> TYPE: PRT
<213> ORGANISM: Artificial Sequence
<220> FEATURE:
<223> OTHER INFORMATION: Amino acid sequence of polypeptide chain L0

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 7
<211> LENGTH: 1743
<212> TYPE: DNA
<213> ORGANISM: Artificial Sequence
<220> FEATURE:
<223> OTHER INFORMATION: DNA sequence of polypeptide chain H1

<400> SEQUENCE: 7

gaggtgcagc tggtgcagtc cggagctgag gtgaagaagc caggatccag cgtgaaggtg     60

agctgcaagg ctagcggcta ctctttcacc caccattgga tccactgggt gaggcaggct    120

cctggacagg gactggagtg gatgggcatg atcgacgctt ccgatagcga gacaagactg    180

tctcagaagt ttaaggaccg cgtgaccatc acagccgata agtctacctc cacagcttac    240

atggagctgt cttccctgag atccgaggac accgccgtgt actattgtgc taggctgggc    300

cggtactatt tcgattattg gggccagggc accacagtga cagtgagctc tgccagcaca    360

aagggccctt ccgtgttccc actggctccc tgctccagaa gcacatctga gtccaccgcc    420

gctctgggct gtctggtgaa ggactacttc cctgagccag tgaccgtgtc ctggaacagc    480

ggcgccctga catctggcgt gcacaccttt ccagctgtgc tgcagtccag cggcctgtac    540

tccctgtctt ccgtggtgac agtgcccagc tcttccctgg gcaccaagac atatacctgc    600

aacgtggacc ataagccttc caataccaag gtggataaga gggtggagag caagtacgga    660

ccaccttgcc caccatgtcc agctcctgag tttgagggag gaccatccgt gttcctgttt    720

cctccaaagc ctaaggacac cctgatgatc agccggacac ctgaggtgac ctgcgtggtg    780

gtggacgtgt ctcaggagga tccagaggtg cagttcaact ggtacgtgga tggcgtggag    840

gtgcacaatg ctaagaccaa gccaagagag gagcagttta attccacata ccgcgtggtg    900

agcgtgctga ccgtgctgca tcaggattgg ctgaacggca aggagtataa gtgcaaggtg    960

tccaataagg gcctgcccag ctctatcgag aagacaatca gcaaggctaa gggacagcct   1020

agggagccac aggtgtacac cctgccccct tctcaggagg agatgacaaa gaaccaggtg   1080

tccctgacct gtctggtgaa gggcttctat ccaagcgaca tcgctgtgga gtgggagtct   1140

aatggccagc ccgagaacaa ttacaagacc acaccacccg tgctggactc tgatggctcc   1200

ttctttctgt attctaggct gacagtggat aagtcccggt ggcaggaggg caacgtgttt   1260

agctgctctg tgatgcacga ggccctgcac aatcattata cccagaagtc cctgagcctg   1320

tctctgggca aggaacctaa gtctagcgac aaaactcata ccagcccccc tagtccagag   1380

gtgcagctgg tggagtccgg aggaggactg gtgcagccag gaggctccct gaggctgagc   1440

tgcgccgctt ctggctacac cgtgtccagc tattgtatgg gctggttcag gcaggctcct   1500
```

```
ggcaagggaa gggagggcgt gtccgctatc gacagcgatg gcagcgtgtc ttacgccgac   1560

agcgtgaagg gcagattcac catctctaag gataactcca agaatacact gtacctgcag   1620

atgaactctc tgcgcgccga ggacaccgcc gtgtactttt gcgctgctga cctgtgctgg   1680

gtggaccagg atcagggcga gtataataca tggggccagg gcaccctggt gacagtgtct   1740

tcc                                                                 1743


<210> SEQ ID NO 8
<211> LENGTH: 581
<212> TYPE: PRT
<213> ORGANISM: Artificial Sequence
<220> FEATURE:
<223> OTHER INFORMATION: Amino acid sequence of polypeptide chain H1

<400> SEQUENCE: 8

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
            20                  25                  30

Trp Ile His Trp Val Arg Gln Ala Pro Gly Gln Gly Leu Glu Trp Met
        35                  40                  45

Gly Met Ile Asp Ala Ser Asp Ser Glu Thr Arg Leu Ser Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

```
Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Glu Pro Lys Ser
        435                 440                 445

Ser Asp Lys Thr His Thr Ser Pro Pro Ser Pro Glu Val Gln Leu Val
    450                 455                 460

Glu Ser Gly Gly Gly Leu Val Gln Pro Gly Gly Ser Leu Arg Leu Ser
465                 470                 475                 480

Cys Ala Ala Ser Gly Tyr Thr Val Ser Ser Tyr Cys Met Gly Trp Phe
                485                 490                 495

Arg Gln Ala Pro Gly Lys Gly Arg Glu Gly Val Ser Ala Ile Asp Ser
            500                 505                 510

Asp Gly Ser Val Ser Tyr Ala Asp Ser Val Lys Gly Arg Phe Thr Ile
        515                 520                 525

Ser Lys Asp Asn Ser Lys Asn Thr Leu Tyr Leu Gln Met Asn Ser Leu
    530                 535                 540

Arg Ala Glu Asp Thr Ala Val Tyr Phe Cys Ala Ala Asp Leu Cys Trp
545                 550                 555                 560

Val Asp Gln Asp Gln Gly Glu Tyr Asn Thr Trp Gly Gln Gly Thr Leu
                565                 570                 575

Val Thr Val Ser Ser
            580


<210> SEQ ID NO 9
<211> LENGTH: 1743
<212> TYPE: DNA
<213> ORGANISM: Artificial Sequence
<220> FEATURE:
<223> OTHER INFORMATION: DNA sequence of polypeptide chain H2

<400> SEQUENCE: 9

gaggtgcagc tggtggagtc cggaggagga ctggtgcagc caggaggctc cctgaggctg      60

agctgcgccg cttctggcta caccgtgtcc agctattgta tgggctggtt caggcaggct     120

cctggcaagg gaagggaggg cgtgtccgct atcgacagcg atggcagcgt gtcttacgcc     180

gacagcgtga agggcagatt caccatctct aaggataact ccaagaatac actgtacctg     240

cagatgaact ctctgcgcgc cgaggacacc gccgtgtact tttgcgctgc tgacctgtgc     300

tgggtggacc aggatcaggg cgagtataat acatggggcc agggcaccct ggtgacagtg     360

tcttccgaac ctaagtctag cgacaaaact cataccagcc cccctagtcc agaggtgcag     420

ctggtgcagt ccggagctga ggtgaagaag ccaggatcca gcgtgaaggt gagctgcaag     480

gctagcggct actctttcac ccaccattgg atccactggg tgaggcaggc tcctggacag     540
```

```
ggactggagt ggatgggcat gatcgacgct tccgatagcg agacaagact gtctcagaag    600

tttaaggacc gcgtgaccat cacagccgat aagtctacct ccacagctta catggagctg    660

tcttccctga gatccgagga caccgccgtg tactattgtg ctaggctggg ccggtactat    720

ttcgattatt ggggccaggg caccacagtg acagtgagct ctgccagcac aaagggccct    780

tccgtgttcc cactggctcc ctgctccaga agcacatctg agtccaccgc cgctctgggc    840

tgtctggtga aggactactt ccctgagcca gtgaccgtgt cctggaacag cggcgccctg    900

acatctggcg tgcacacctt tccagctgtg ctgcagtcca gcggcctgta ctccctgtct    960

tccgtggtga cagtgcccag ctcttccctg ggcaccaaga catatacctg caacgtggac   1020

cataagcctt ccaataccaa ggtggataag agggtggaga gcaagtacgg accaccttgc   1080

ccaccatgtc cagctcctga gtttgaggga ggaccatccg tgttcctgtt tcctccaaag   1140

cctaaggaca ccctgatgat cagccggaca cctgaggtga cctgcgtggt ggtggacgtg   1200

tctcaggagg atccagaggt gcagttcaac tggtacgtgg atggcgtgga ggtgcacaat   1260

gctaagacca agccaagaga ggagcagttt aattccacat accgcgtggt gagcgtgctg   1320

accgtgctgc atcaggattg gctgaacggc aaggagtata agtgcaaggt gtccaataag   1380

ggcctgccca gctctatcga gaagacaatc agcaaggcta agggacagcc tagggagcca   1440

caggtgtaca ccctgccccc ttctcaggag gagatgacaa agaaccaggt gtccctgacc   1500

tgtctggtga agggcttcta tccaagcgac atcgctgtgg agtgggagtc taatggccag   1560

cccgagaaca attacaagac cacaccaccc gtgctggact ctgatggctc cttctttctg   1620

tattctaggc tgacagtgga taagtcccgg tggcaggagg gcaacgtgtt tagctgctct   1680

gtgatgcacg aggccctgca caatcattat acccagaagt ccctgagcct gtctctgggc   1740

aag                                                                 1743

<210> SEQ ID NO 10
<211> LENGTH: 581
<212> TYPE: PRT
<213> ORGANISM: Artificial Sequence
<220> FEATURE:
<223> OTHER INFORMATION: Amino acid sequence of polypeptide chain H2

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Pro Lys Ser Ser Asp
        115                 120                 125

Lys Thr His Thr Ser Pro Pro Ser Pro Glu Val Gln Leu Val Gln Ser
    130                 135                 140
```

```
Gly Ala Glu Val Lys Lys Pro Gly Ser Ser Val Lys Val Ser Cys Lys
145                 150                 155                 160

Ala Ser Gly Tyr Ser Phe Thr His His Trp Ile His Trp Val Arg Gln
                165                 170                 175

Ala Pro Gly Gln Gly Leu Glu Trp Met Gly Met Ile Asp Ala Ser Asp
            180                 185                 190

Ser Glu Thr Arg Leu Ser Gln Lys Phe Lys Asp Arg Val Thr Ile Thr
        195                 200                 205

Ala Asp Lys Ser Thr Ser Thr Ala Tyr Met Glu Leu Ser Ser Leu Arg
    210                 215                 220

Ser Glu Asp Thr Ala Val Tyr Tyr Cys Ala Arg Leu Gly Arg Tyr Tyr
225                 230                 235                 240

Phe Asp Tyr Trp Gly Gln Gly Thr Thr Val Thr Val Ser Ser Ala Ser
                245                 250                 255

Thr Lys Gly Pro Ser Val Phe Pro Leu Ala Pro Cys Ser Arg Ser Thr
            260                 265                 270

Ser Glu Ser Thr Ala Ala Leu Gly Cys Leu Val Lys Asp Tyr Phe Pro
        275                 280                 285

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Lys Thr Tyr Thr
                325                 330                 335

Cys Asn Val Asp His Lys Pro Ser Asn Thr Lys Val Asp Lys Arg Val
            340                 345                 350

Glu Ser Lys Tyr Gly Pro Pro Cys Pro Pro Cys Pro Ala Pro Glu Phe
        355                 360                 365

Glu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser Gln Glu Asp Pro Glu Val Gln Phe Asn Trp Tyr Val Asp Gly Val
                405                 410                 415

Glu Val His Asn Ala Lys Thr Lys Pro Arg Glu Glu Gln Phe Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Gly Leu Pro Ser
    450                 455                 460

Ser Ile Glu Lys Thr Ile Ser Lys Ala Lys Gly Gln Pro Arg Glu Pro
465                 470                 475                 480

Gln Val Tyr Thr Leu Pro Pro Ser Gln Glu Glu Met Thr Lys Asn Gln
                485                 490                 495

Val Ser Leu Thr Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
        515                 520                 525

Pro Pro Val Leu Asp Ser Asp Gly Ser Phe Phe Leu Tyr Ser Arg Leu
    530                 535                 540

Thr Val Asp Lys Ser Arg Trp Gln Glu Gly Asn Val Phe Ser Cys Ser
545                 550                 555                 560
```

```
Val Met His Glu Ala Leu His Asn His Tyr Thr Gln Lys Ser Leu Ser
                565                 570                 575

Leu Ser Leu Gly Lys
            580


<210> SEQ ID NO 11
<211> LENGTH: 1725
<212> TYPE: DNA
<213> ORGANISM: Artificial Sequence
<220> FEATURE:
<223> OTHER INFORMATION: DNA sequence of polypeptide chain H3

<400> SEQUENCE: 11

gaggtgcagc tggtgcagtc cggagctgag gtgaagaagc caggatccag cgtgaaggtg     60

agctgcaagg ctagcggcta ctctttcacc caccattgga tccactgggt gaggcaggct    120

cctggacagg gactggagtg gatgggcatg atcgacgctt ccgatagcga gacaagactg    180

tctcagaagt ttaaggaccg cgtgaccatc acagccgata agtctacctc cacagcttac    240

atggagctgt cttccctgag atccgaggac accgccgtgt actattgtgc taggctgggc    300

cggtactatt tcgattattg gggccagggc accacagtga cagtgagctc tgccagcaca    360

aagggccctt ccgtgttccc actggctccc tgctccagaa gcacatctga gtccaccgcc    420

gctctgggct gtctggtgaa ggactacttc cctgagccag tgaccgtgtc ctggaacagc    480

ggcgccctga catctggcgt gcacaccttt ccagctgtgc tgcagtccag cggcctgtac    540

tccctgtctt ccgtggtgac agtgcccagc tcttccctgg gcaccaagac atatacctgc    600

aacgtggacc ataagccttc caataccaag gtggataaga gggtggagag caagtacgga    660

ccaccttgcc caccatgtcc agctcctgag tttgagggag gaccatccgt gttcctgttt    720

cctccaaagc ctaaggacac cctgatgatc agccggacac ctgaggtgac ctgcgtggtg    780

gtggacgtgt ctcaggagga tccagaggtg cagttcaact ggtacgtgga tggcgtggag    840

gtgcacaatg ctaagaccaa gccaagagag gagcagttta attccacata ccgcgtggtg    900

agcgtgctga ccgtgctgca tcaggattgg ctgaacggca aggagtataa gtgcaaggtg    960

tccaataagg gcctgcccag ctctatcgag aagacaatca gcaaggctaa gggacagcct   1020

agggagccac aggtgtacac cctgccccct tctcaggagg agatgacaaa gaaccaggtg   1080

tccctgacct gtctggtgaa gggcttctat ccaagcgaca tcgctgtgga gtgggagtct   1140

aatggccagc ccgagaacaa ttacaagacc acaccacccg tgctggactc tgatggctcc   1200

ttctttctgt attctaggct gacagtggat aagtcccggt ggcaggaggg caacgtgttt   1260

agctgctctg tgatgcacga ggccctgcac aatcattata cccagaagtc cctgagcctg   1320

tctctgggca agggtggagg cggtagtgga ggcggttcag aggtgcagct ggtggagtcc   1380

ggaggaggac tggtgcagcc aggaggctcc ctgaggctga gctgcgccgc ttctggctac   1440

accgtgtcca gctattgtat gggctggttc aggcaggctc ctggcaaggg aagggagggc   1500

gtgtccgcta tcgacagcga tggcagcgtg tcttacgccg acagcgtgaa gggcagattc   1560

accatctcta aggataactc caagaataca ctgtacctgc agatgaactc tctgcgcgcc   1620

gaggacaccg ccgtgtactt ttgcgctgct gacctgtgct gggtggacca ggatcagggc   1680

gagtataata catggggcca gggcaccctg gtgacagtgt cttcc                   1725


<210> SEQ ID NO 12
<211> LENGTH: 575
<212> TYPE: PRT
<213> ORGANISM: Artificial Sequence
```

```
<220> FEATURE:
<223> OTHER INFORMATION: Amino acid sequence of polypeptide chain H3

<400> SEQUENCE: 12

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
            20                  25                  30

Trp Ile His Trp Val Arg Gln Ala Pro Gly Gln Gly Leu Glu Trp Met
        35                  40                  45

Gly Met Ile Asp Ala Ser Asp Ser Glu Thr Arg Leu Ser Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400
```

```
Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys Gly Gly Gly Gly
        435                 440                 445

Ser Gly Gly Gly Ser Glu Val Gln Leu Val Glu Ser Gly Gly Gly Leu
    450                 455                 460

Val Gln Pro Gly Gly Ser Leu Arg Leu Ser Cys Ala Ala Ser Gly Tyr
465                 470                 475                 480

Thr Val Ser Ser Tyr Cys Met Gly Trp Phe Arg Gln Ala Pro Gly Lys
                485                 490                 495

Gly Arg Glu Gly Val Ser Ala Ile Asp Ser Asp Gly Ser Val Ser Tyr
            500                 505                 510

Ala Asp Ser Val Lys Gly Arg Phe Thr Ile Ser Lys Asp Asn Ser Lys
        515                 520                 525

Asn Thr Leu Tyr Leu Gln Met Asn Ser Leu Arg Ala Glu Asp Thr Ala
    530                 535                 540

Val Tyr Phe Cys Ala Ala Asp Leu Cys Trp Val Asp Gln Asp Gln Gly
545                 550                 555                 560

Glu Tyr Asn Thr Trp Gly Gln Gly Thr Leu Val Thr Val Ser Ser
                565                 570                 575
```

<210> SEQ ID NO 13
<211> LENGTH: 1725
<212> TYPE: DNA
<213> ORGANISM: Artificial Sequence
<220> FEATURE:
<223> OTHER INFORMATION: DNA sequence of polypeptide chain H4

<400> SEQUENCE: 13

```
gaggtgcagc tggtggagtc cggaggagga ctggtgcagc caggaggctc cctgaggctg      60

agctgcgccg cttctggcta caccgtgtcc agctattgta tggctggtt caggcaggct     120

cctggcaagg gaagggaggg cgtgtccgct atcgacagcg atggcagcgt gtcttacgcc     180

gacagcgtga agggcagatt caccatctct aaggataact ccaagaatac actgtacctg     240

cagatgaact ctctgcgcgc cgaggacacc gccgtgtact tttgcgctgc tgacctgtgc     300

tgggtggacc aggatcaggg cgagtataat acatggggcc agggcaccct ggtgacagtg     360

tcttccggtg gaggcggtag tggaggcggt tcagaggtgc agctggtgca gtccggagct     420

gaggtgaaga agccaggatc cagcgtgaag gtgagctgca aggctagcgg ctactctttc     480

acccaccatt ggatccactg ggtgaggcag gctcctggac agggactgga gtggatgggc     540

atgatcgacg cttccgatag cgagacaaga ctgtctcaga agtttaagga ccgcgtgacc     600

atcacagccg ataagtctac ctccacagct tacatggagc tgtcttccct gagatccgag     660

gacaccgccg tgtactattg tgctaggctg ggccggtact atttcgatta ttggggccag     720

ggcaccacag tgacagtgag ctctgccagc acaaagggcc cttccgtgtt cccactggct     780

ccctgctcca gaagcacatc tgagtccacc gccgctctgg gctgtctggt gaaggactac     840

ttccctgagc cagtgaccgt gtcctggaac agcggcgccc tgacatctgg cgtgcacacc     900

tttccagctg tgctgcagtc cagcggcctg tactccctgt cttccgtggt gacagtgccc     960

agctcttccc tgggcaccaa gacatatacc tgcaacgtgg accataagcc ttccaatacc    1020

aaggtggata agagggtgga gagcaagtac ggaccacctt gcccaccatg tccagctcct    1080
```

```
gagtttgagg gaggaccatc cgtgttcctg tttcctccaa agcctaagga caccctgatg   1140

atcagccgga cacctgaggt gacctgcgtg gtggtggacg tgtctcagga ggatccagag   1200

gtgcagttca actggtacgt ggatggcgtg gaggtgcaca atgctaagac caagccaaga   1260

gaggagcagt ttaattccac ataccgcgtg gtgagcgtgc tgaccgtgct gcatcaggat   1320

tggctgaacg gcaaggagta taagtgcaag gtgtccaata agggcctgcc cagctctatc   1380

gagaagacaa tcagcaaggc taagggacag cctagggagc cacaggtgta caccctgccc   1440

ccttctcagg aggagatgac aaagaaccag gtgtccctga cctgtctggt gaagggcttc   1500

tatccaagcg acatcgctgt ggagtgggag tctaatggcc agcccgagaa caattacaag   1560

accacaccac ccgtgctgga ctctgatggc tccttctttc tgtattctag gctgacagtg   1620

gataagtccc ggtggcagga gggcaacgtg tttagctgct ctgtgatgca cgaggccctg   1680

cacaatcatt atacccagaa gtccctgagc ctgtctctgg gcaag                 1725


<210> SEQ ID NO 14
<211> LENGTH: 575
<212> TYPE: PRT
<213> ORGANISM: Artificial Sequence
<220> FEATURE:
<223> OTHER INFORMATION: Amino acid sequence of polypeptide chain H4

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Gly Gly Gly Gly Ser Gly
        115                 120                 125

Gly Gly Ser Glu Val Gln Leu Val Gln Ser Gly Ala Glu Val Lys Lys
    130                 135                 140

Pro Gly Ser Ser Val Lys Val Ser Cys Lys Ala Ser Gly Tyr Ser Phe
145                 150                 155                 160

Thr His His Trp Ile His Trp Val Arg Gln Ala Pro Gly Gln Gly Leu
                165                 170                 175

Glu Trp Met Gly Met Ile Asp Ala Ser Asp Ser Glu Thr Arg Leu Ser
            180                 185                 190

Gln Lys Phe Lys Asp Arg Val Thr Ile Thr Ala Asp Lys Ser Thr Ser
        195                 200                 205

Thr Ala Tyr Met Glu Leu Ser Ser Leu Arg Ser Glu Asp Thr Ala Val
    210                 215                 220

Tyr Tyr Cys Ala Arg Leu Gly Arg Tyr Tyr Phe Asp Tyr Trp Gly Gln
225                 230                 235                 240
```

```
Gly Thr Thr Val Thr Val Ser Ser Ala Ser Thr Lys Gly Pro Ser Val
                245                 250                 255

Phe Pro Leu Ala Pro Cys Ser Arg Ser Thr Ser Glu Ser Thr Ala Ala
            260                 265                 270

Leu Gly Cys Leu Val Lys Asp Tyr Phe Pro Glu Pro Val Thr Val Ser
        275                 280                 285

Trp Asn Ser Gly Ala Leu Thr Ser Gly Val His Thr Phe Pro Ala Val
    290                 295                 300

Leu Gln Ser Ser Gly Leu Tyr Ser Leu Ser Ser Val Val Thr Val Pro
305                 310                 315                 320

Ser Ser Ser Leu Gly Thr Lys Thr Tyr Thr Cys Asn Val Asp His Lys
                325                 330                 335

Pro Ser Asn Thr Lys Val Asp Lys Arg Val Glu Ser Lys Tyr Gly Pro
            340                 345                 350

Pro Cys Pro Pro Cys Pro Ala Pro Glu Phe Glu Gly Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Val Asp Val Ser Gln Glu Asp Pro Glu
385                 390                 395                 400

Val Gln Phe Asn Trp Tyr Val Asp Gly Val Glu Val His Asn Ala Lys
                405                 410                 415

Thr Lys Pro Arg Glu Glu Gln Phe Asn Ser Thr Tyr Arg Val Val Ser
            420                 425                 430

Val Leu Thr Val Leu His Gln Asp Trp Leu Asn Gly Lys Glu Tyr Lys
        435                 440                 445

Cys Lys Val Ser Asn Lys Gly Leu Pro Ser Ser Ile Glu Lys Thr Ile
    450                 455                 460

Ser Lys Ala Lys Gly Gln Pro Arg Glu Pro Gln Val Tyr Thr Leu Pro
465                 470                 475                 480

Pro Ser Gln Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Arg Leu Thr Val Asp Lys Ser Arg
    530                 535                 540

Trp Gln Glu Gly Asn Val Phe Ser Cys Ser Val Met His Glu Ala Leu
545                 550                 555                 560

His Asn His Tyr Thr Gln Lys Ser Leu Ser Leu Ser Leu Gly Lys
                565                 570                 575
```

<210> SEQ ID NO 15
<211> LENGTH: 1053
<212> TYPE: DNA
<213> ORGANISM: Artificial Sequence
<220> FEATURE:
<223> OTHER INFORMATION: DNA sequence of polypeptide chain L1

<400> SEQUENCE: 15

```
gagatcgtgc tgacccagtc tccagccaca ctgtctctgt ccccaggaga gagggccacc      60

ctgagctgcc gggcttctga gaacgtgggc acatacatct cctggtatca gcagaagcca     120

ggacaggctc ctaggctgct gatctacggc gctagcaata gatataccgg catccctgct     180
```

```
cgcttcagcg gatctggatc cggcacagac tttaccctga caatctccag cctggagcca    240

gaggatttcg ccgtgtacta ttgtggcgag tcctacggcc acctgtatac ctttggcggc    300

ggcacaaagg tggagatcaa gcgaacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gtgaacctaa gtctagcgac    660

aaaactcata ccagcccccc tagtccagag gtgcagctgg tggagtccgg aggaggactg    720

gtgcagccag gaggctccct gaggctgagc tgcgccgctt ctggctacac cgtgtccagc    780

tattgtatgg gctggttcag gcaggctcct ggcaagggaa gggagggcgt gtccgctatc    840

gacagcgatg gcagcgtgtc ttacgccgac agcgtgaagg gcagattcac catctctaag    900

gataactcca agaatacact gtacctgcag atgaactctc tgcgcgccga ggacaccgcc    960

gtgtactttt gcgctgctga cctgtgctgg gtggaccagg atcagggcga gtataataca   1020

tggggccagg gcaccctggt gacagtgtct tcc                                1053
```

<210> SEQ ID NO 16
<211> LENGTH: 351
<212> TYPE: PRT
<213> ORGANISM: Artificial Sequence
<220> FEATURE:
<223> OTHER INFORMATION: Amino acid sequence of polypeptide chain L1

<400> SEQUENCE: 16

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys Glu Pro Lys Ser Ser Asp Lys Thr His Thr
    210                 215                 220

Ser Pro Pro Ser Pro Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Thr Val Ser Ser Tyr Cys Met Gly Trp Phe Arg Gln Ala Pro Gly Lys
            260                 265                 270

Gly Arg Glu Gly Val Ser Ala Ile Asp Ser Asp Gly Ser Val Ser Tyr
        275                 280                 285

Ala Asp Ser Val Lys Gly Arg Phe Thr Ile Ser Lys Asp Asn Ser Lys
    290                 295                 300

Asn Thr Leu Tyr Leu Gln Met Asn Ser Leu Arg Ala Glu Asp Thr Ala
305                 310                 315                 320

Val Tyr Phe Cys Ala Ala Asp Leu Cys Trp Val Asp Gln Asp Gln Gly
                325                 330                 335

Glu Tyr Asn Thr Trp Gly Gln Gly Thr Leu Val Thr Val Ser Ser
            340                 345                 350
```

<210> SEQ ID NO 17
<211> LENGTH: 1053
<212> TYPE: DNA
<213> ORGANISM: Artificial Sequence
<220> FEATURE:
<223> OTHER INFORMATION: DNA sequence of polypeptide chain L2

<400> SEQUENCE: 17

```
gaggtgcagc tggtggagtc cggaggagga ctggtgcagc caggaggctc cctgaggctg     60
agctgcgccg cttctggcta caccgtgtcc agctattgta tgggctggtt caggcaggct    120
cctggcaagg gaagggaggg cgtgtccgct atcgacagcg atggcagcgt gtcttacgcc    180
gacagcgtga agggcagatt caccatctct aaggataact ccaagaatac actgtacctg    240
cagatgaact ctctgcgcgc cgaggacacc gccgtgtact tttgcgctgc tgacctgtgc    300
tgggtggacc aggatcaggg cgagtataat acatggggcc agggcaccct ggtgacagtg    360
tcttccgaac ctaagtctag cgacaaaact cataccagcc cccctagtcc agagatcgtg    420
ctgacccagt ctccagccac actgtctctg tccccaggag agagggccac cctgagctgc    480
cgggcttctg agaacgtggg cacatacatc tcctggtatc agcagaagcc aggacaggct    540
cctaggctgc tgatctacgg cgctagcaat agatataccg gcatccctgc tcgcttcagc    600
ggatctggat ccggcacaga ctttaccctg acaatctcca gcctggagcc agaggatttc    660
gccgtgtact attgtggcga gtcctacggc cacctgtata cctttggcgg cggcacaaag    720
gtggagatca agcgaacggt ggctgcacca tctgtcttca tcttcccgcc atctgatgag    780
cagttgaaat ctggaactgc ctctgttgtg tgcctgctga ataacttcta tcccagagag    840
gccaaagtac agtggaaggt ggataacgcc ctccaatcgg gtaactccca ggagagtgtc    900
acagagcagg acagcaagga cagcacctac agcctcagca gcaccctgac gctgagcaaa    960
gcagactacg agaaacacaa agtctacgcc tgcgaagtca cccatcaggg cctgagctcg   1020
cccgtcacaa agagcttcaa caggggagag tgt                                1053
```

<210> SEQ ID NO 18
<211> LENGTH: 351
<212> TYPE: PRT
<213> ORGANISM: Artificial Sequence

```
<220> FEATURE:
<223> OTHER INFORMATION: Amino acid sequence of polypeptide chain L2

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Pro Lys Ser Ser Asp
        115                 120                 125

Lys Thr His Thr Ser Pro Pro Ser Pro Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Glu Asn Val Gly Thr Tyr Ile Ser Trp Tyr Gln Gln Lys
                165                 170                 175

Pro Gly Gln Ala Pro Arg Leu Leu Ile Tyr Gly Ala Ser Asn Arg Tyr
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Glu Pro Glu Asp Phe Ala Val Tyr Tyr
    210                 215                 220

Cys Gly Glu Ser Tyr Gly His Leu Tyr Thr Phe Gly Gly Gly Thr Lys
225                 230                 235                 240

Val Glu Ile Lys Arg Thr Val Ala Ala Pro Ser Val Phe Ile Phe Pro
                245                 250                 255

Pro Ser Asp Glu Gln Leu Lys Ser Gly Thr Ala Ser Val Val Cys Leu
            260                 265                 270

Leu Asn Asn Phe Tyr Pro Arg Glu Ala Lys Val Gln Trp Lys Val Asp
        275                 280                 285

Asn Ala Leu Gln Ser Gly Asn Ser Gln Glu Ser Val Thr Glu Gln Asp
    290                 295                 300

Ser Lys Asp Ser Thr Tyr Ser Leu Ser Ser Thr Leu Thr Leu Ser Lys
305                 310                 315                 320

Ala Asp Tyr Glu Lys His Lys Val Tyr Ala Cys Glu Val Thr His Gln
                325                 330                 335

Gly Leu Ser Ser Pro Val Thr Lys Ser Phe Asn Arg Gly Glu Cys
            340                 345                 350


<210> SEQ ID NO 19
<211> LENGTH: 1035
<212> TYPE: DNA
<213> ORGANISM: Artificial Sequence
<220> FEATURE:
<223> OTHER INFORMATION: DNA sequence of polypeptide chain L3
```

<400> SEQUENCE: 19

```
gagatcgtgc tgacccagtc tccagccaca ctgtctctgt ccccaggaga gagggccacc      60

ctgagctgcc gggcttctga gaacgtgggc acatacatct cctggtatca gcagaagcca     120

ggacaggctc ctaggctgct gatctacggc gctagcaata gatataccgg catccctgct     180

cgcttcagcg gatctggatc cggcacagac tttaccctga caatctccag cctggagcca     240

gaggatttcg ccgtgtacta ttgtggcgag tcctacggcc acctgtatac ctttggcggc     300

ggcacaaagg tggagatcaa gcgaacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gtggtggagg cggtagtgga     660

ggcggttcag aggtgcagct ggtggagtcc ggaggaggac tggtgcagcc aggaggctcc     720

ctgaggctga gctgcgccgc ttctggctac accgtgtcca gctattgtat gggctggttc     780

aggcaggctc ctggcaaggg aagggagggc gtgtccgcta tcgacagcga tggcagcgtg     840

tcttacgccg acagcgtgaa gggcagattc accatctcta aggataactc caagaataca     900

ctgtacctgc agatgaactc tctgcgcgcc gaggacaccg ccgtgtactt ttgcgctgct     960

gacctgtgct gggtggacca ggatcagggc gagtataata catggggcca gggcaccctg    1020

gtgacagtgt cttcc                                                     1035
```

<210> SEQ ID NO 20
<211> LENGTH: 345
<212> TYPE: PRT
<213> ORGANISM: Artificial Sequence
<220> FEATURE:
<223> OTHER INFORMATION: Amino acid sequence of polypeptide chain L3

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Ser Glu
    210                 215                 220

Val Gln Leu Val Glu Ser Gly Gly Gly Leu Val Gln Pro Gly Gly Ser
225                 230                 235                 240

Leu Arg Leu Ser Cys Ala Ala Ser Gly Tyr Thr Val Ser Ser Tyr Cys
                245                 250                 255

Met Gly Trp Phe Arg Gln Ala Pro Gly Lys Gly Arg Glu Gly Val Ser
            260                 265                 270

Ala Ile Asp Ser Asp Gly Ser Val Ser Tyr Ala Asp Ser Val Lys Gly
        275                 280                 285

Arg Phe Thr Ile Ser Lys Asp Asn Ser Lys Asn Thr Leu Tyr Leu Gln
    290                 295                 300

Met Asn Ser Leu Arg Ala Glu Asp Thr Ala Val Tyr Phe Cys Ala Ala
305                 310                 315                 320

Asp Leu Cys Trp Val Asp Gln Asp Gln Gly Glu Tyr Asn Thr Trp Gly
                325                 330                 335

Gln Gly Thr Leu Val Thr Val Ser Ser
            340                 345


<210> SEQ ID NO 21
<211> LENGTH: 1035
<212> TYPE: DNA
<213> ORGANISM: Artificial Sequence
<220> FEATURE:
<223> OTHER INFORMATION: DNA sequence of polypeptide chain L4

<400> SEQUENCE: 21

gaggtgcagc tggtggagtc cggaggagga ctggtgcagc caggaggctc cctgaggctg     60

agctgcgccg cttctggcta caccgtgtcc agctattgta tgggctggtt caggcaggct    120

cctggcaagg gaagggaggg cgtgtccgct atcgacagcg atggcagcgt gtcttacgcc    180

gacagcgtga agggcagatt caccatctct aaggataact ccaagaatac actgtacctg    240

cagatgaact ctctgcgcgc cgaggacacc gccgtgtact tttgcgctgc tgacctgtgc    300

tgggtggacc aggatcaggg cgagtataat acatggggcc agggcaccct ggtgacagtg    360

tcttccggtg gaggcggtag tggaggcggt tcagagatcg tgctgaccca gtctccagcc    420

acactgtctc tgtccccagg agagagggcc accctgagct gccgggcttc tgagaacgtg    480

ggcacataca tctcctggta tcagcagaag ccaggacagg ctcctaggct gctgatctac    540

ggcgctagca atagatatac cggcatccct gctcgcttca gcggatctgg atccggcaca    600

gactttaccc tgacaatctc cagcctggag ccagaggatt tcgccgtgta ctattgtggc    660

gagtcctacg gccacctgta tacctttggc ggcggcacaa aggtggagat caagcgaacg    720

gtggctgcac catctgtctt catcttcccg ccatctgatg agcagttgaa atctggaact    780

gcctctgttg tgtgcctgct gaataacttc tatcccagag aggccaaagt acagtggaag    840

gtggataacg ccctccaatc gggtaactcc caggagagtg tcacagagca ggacagcaag    900

gacagcacct acagcctcag cagcaccctg acgctgagca aagcagacta cgagaaacac    960
```

```
aaagtctacg cctgcgaagt cacccatcag ggcctgagct cgcccgtcac aaagagcttc   1020

aacaggggag agtgt                                                    1035


<210> SEQ ID NO 22
<211> LENGTH: 345
<212> TYPE: PRT
<213> ORGANISM: Artificial Sequence
<220> FEATURE:
<223> OTHER INFORMATION: Amino acid sequence of polypeptide chain L4

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Gly Gly Gly Gly Ser Gly
        115                 120                 125

Gly Gly Ser Glu Ile Val Leu Thr Gln Ser Pro Ala Thr Leu Ser Leu
    130                 135                 140

Ser Pro Gly Glu Arg Ala Thr Leu Ser Cys Arg Ala Ser Glu Asn Val
145                 150                 155                 160

Gly Thr Tyr Ile Ser Trp Tyr Gln Gln Lys Pro Gly Gln Ala Pro Arg
                165                 170                 175

Leu Leu Ile Tyr Gly Ala Ser Asn Arg Tyr Thr Gly Ile Pro Ala Arg
            180                 185                 190

Phe Ser Gly Ser Gly Ser Gly Thr Asp Phe Thr Leu Thr Ile Ser Ser
        195                 200                 205

Leu Glu Pro Glu Asp Phe Ala Val Tyr Tyr Cys Gly Glu Ser Tyr Gly
    210                 215                 220

His Leu Tyr Thr Phe Gly Gly Gly Thr Lys Val Glu Ile Lys Arg Thr
225                 230                 235                 240

Val Ala Ala Pro Ser Val Phe Ile Phe Pro Pro Ser Asp Glu Gln Leu
                245                 250                 255

Lys Ser Gly Thr Ala Ser Val Val Cys Leu Leu Asn Asn Phe Tyr Pro
            260                 265                 270

Arg Glu Ala Lys Val Gln Trp Lys Val Asp Asn Ala Leu Gln Ser Gly
        275                 280                 285

Asn Ser Gln Glu Ser Val Thr Glu Gln Asp Ser Lys Asp Ser Thr Tyr
    290                 295                 300

Ser Leu Ser Ser Thr Leu Thr Leu Ser Lys Ala Asp Tyr Glu Lys His
305                 310                 315                 320

Lys Val Tyr Ala Cys Glu Val Thr His Gln Gly Leu Ser Ser Pro Val
                325                 330                 335

Thr Lys Ser Phe Asn Arg Gly Glu Cys
            340                 345
```

<210> SEQ ID NO 23
<211> LENGTH: 1743
<212> TYPE: DNA
<213> ORGANISM: Artificial Sequence
<220> FEATURE:
<223> OTHER INFORMATION: DNA sequence of polypeptide chain H5

<400> SEQUENCE: 23
gaggtgcagc tggtgcagtc cggagctgag gtgaagaagc caggatccag cgtgaaggtg 60
agctgcaagg ctagcggcta ctctttcacc caccattgga tccactgggt gaggcaggct 120
cctggacagg gactggagtg gatgggcatg atcgacgctt ccgatagcga gacaagactg 180
tctcagaagt ttaaggaccg cgtgaccatc acagccgata agtctacctc cacagcttac 240
atggagctgt cttccctgag atccgaggac accgccgtgt actattgtgc taggctgggc 300
cggtactatt tcgattattg gggccagggc accacagtga cagtgagctc tgccagcaca 360
aagggccctt ccgtgttccc actggctccc tgctccagaa gcacatctga gtccaccgcc 420
gctctgggct gtctggtgaa ggactacttc cctgagccag tgaccgtgtc ctggaacagc 480
ggcgccctga catctggcgt gcacaccttt ccagctgtgc tgcagtccag cggcctgtac 540
tccctgtctt ccgtggtgac agtgcccagc tcttccctgg gcaccaagac atatacctgc 600
aacgtggacc ataagccttc caataccaag gtggataaga gggtggagag caagtacgga 660
ccaccttgcc caccatgtcc agctcctgag tttgagggag gaccatccgt gttcctgttt 720
cctccaaagc ctaaggacac cctgatgatc agccggacac ctgaggtgac ctgcgtggtg 780
gtggacgtgt ctcaggagga tccagaggtg cagttcaact ggtacgtgga tggcgtggag 840
gtgcacaatg ctaagaccaa gccaagagag gagcagttta attccacata ccgcgtggtg 900
agcgtgctga ccgtgctgca tcaggattgg ctgaacggca aggagtataa gtgcaaggtg 960
tccaataagg gcctgcccag ctctatcgag aagacaatca gcaaggctaa gggacagcct 1020
agggagccac aggtgtacac cctgccccct tctcaggagg agatgacaaa gaaccaggtg 1080
tccctgacct gtctggtgaa gggcttctat ccaagcgaca tcgctgtgga gtgggagtct 1140
aatggccagc ccgagaacaa ttacaagacc acaccacccg tgctggactc tgatggctcc 1200
ttctttctgt attctaggct gacagtggat aagtcccggt ggcaggaggg caacgtgttt 1260
agctgctctg tgatgcacga ggccctgcac aatcattata cccagaagtc cctgagcctg 1320
tctctgggca agggtggagg cggtagtgga ggcggtggtt caggcggagg cggatctgag 1380
gtgcagctgg tggagtccgg aggaggactg gtgcagccag gaggctccct gaggctgagc 1440
tgcgccgctt ctggctacac cgtgtccagc tattgtatgg gctggttcag gcaggctcct 1500
ggcaagggaa gggagggcgt gtccgctatc gacagcgatg gcagcgtgtc ttacgccgac 1560
agcgtgaagg gcagattcac catctctaag gataactcca agaatacact gtacctgcag 1620
atgaactctc tgcgcgccga ggacaccgcc gtgtactttt gcgctgctga cctgtgctgg 1680
gtggaccagg atcagggcga gtataataca tggggccagg gcaccctggt gacagtgtct 1740
tcc 1743

<210> SEQ ID NO 24
<211> LENGTH: 581
<212> TYPE: PRT
<213> ORGANISM: Artificial Sequence
<220> FEATURE:
<223> OTHER INFORMATION: Amino acid sequence of polypeptide chain H5

<400> SEQUENCE: 24

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr His His
            20                  25                  30

Trp Ile His Trp Val Arg Gln Ala Pro Gly Gln Gly Leu Glu Trp Met
        35                  40                  45

Gly Met Ile Asp Ala Ser Asp Ser Glu Thr Arg Leu Ser Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Arg Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415
```

```
Gly Asn Val Phe Ser Cys Ser Val Met His Glu Ala Leu His Asn His
            420                 425                 430

Tyr Thr Gln Lys Ser Leu Ser Leu Ser Leu Gly Lys Gly Gly Gly Gly
        435                 440                 445

Ser Gly Gly Gly Gly Ser Gly Gly Gly Gly Ser Glu Val Gln Leu Val
    450                 455                 460

Glu Ser Gly Gly Gly Leu Val Gln Pro Gly Gly Ser Leu Arg Leu Ser
465                 470                 475                 480

Cys Ala Ala Ser Gly Tyr Thr Val Ser Ser Tyr Cys Met Gly Trp Phe
                485                 490                 495

Arg Gln Ala Pro Gly Lys Gly Arg Glu Gly Val Ser Ala Ile Asp Ser
            500                 505                 510

Asp Gly Ser Val Ser Tyr Ala Asp Ser Val Lys Gly Arg Phe Thr Ile
        515                 520                 525

Ser Lys Asp Asn Ser Lys Asn Thr Leu Tyr Leu Gln Met Asn Ser Leu
    530                 535                 540

Arg Ala Glu Asp Thr Ala Val Tyr Phe Cys Ala Ala Asp Leu Cys Trp
545                 550                 555                 560

Val Asp Gln Asp Gln Gly Glu Tyr Asn Thr Trp Gly Gln Gly Thr Leu
                565                 570                 575

Val Thr Val Ser Ser
            580
```

<210> SEQ ID NO 25
<211> LENGTH: 1743
<212> TYPE: DNA
<213> ORGANISM: Artificial Sequence
<220> FEATURE:
<223> OTHER INFORMATION: DNA sequence of polypeptide chain H6

<400> SEQUENCE: 25

```
gaggtgcagc tggtggagtc cggaggagga ctggtgcagc caggaggctc cctgaggctg      60

agctgcgccg cttctggcta caccgtgtcc agctattgta tgggctggtt caggcaggct     120

cctggcaagg gaagggaggg cgtgtccgct atcgacagcg atggcagcgt gtcttacgcc     180

gacagcgtga agggcagatt caccatctct aaggataact ccaagaatac actgtacctg     240

cagatgaact ctctgcgcgc cgaggacacc gccgtgtact tttgcgctgc tgacctgtgc     300

tgggtggacc aggatcaggg cgagtataat acatggggcc agggcaccct ggtgacagtg     360

tcttccggtg gaggcggtag tggaggcggt ggttcaggcg gaggcggatc tgaggtgcag     420

ctggtgcagt ccggagctga ggtgaagaag ccaggatcca gcgtgaaggt gagctgcaag     480

gctagcggct actctttcac ccaccattgg atccactggg tgaggcaggc tcctggacag     540

ggactggagt ggatgggcat gatcgacgct tccgatagcg agacaagact gtctcagaag     600

tttaaggacc gcgtgaccat cacagccgat aagtctacct ccacagctta catggagctg     660

tcttccctga gatccgagga caccgccgtg tactattgtg ctaggctggg ccggtactat     720

ttcgattatt ggggccaggg caccacagtg acagtgagct ctgccagcac aaagggccct     780

tccgtgttcc cactggctcc ctgctccaga agcacatctg agtccaccgc cgctctgggc     840

tgtctggtga aggactactt ccctgagcca gtgaccgtgt cctggaacag cggcgccctg     900

acatctggcg tgcacacctt tccagctgtg ctgcagtcca gcggcctgta ctccctgtct     960

tccgtggtga cagtgcccag ctcttccctg ggcaccaaga catatacctg caacgtggac    1020

cataagcctt ccaataccaa ggtggataag agggtggaga gcaagtacgg accaccttgc    1080
```

```
ccaccatgtc cagctcctga gtttgaggga ggaccatccg tgttcctgtt tcctccaaag   1140

cctaaggaca ccctgatgat cagccggaca cctgaggtga cctgcgtggt ggtggacgtg   1200

tctcaggagg atccagaggt gcagttcaac tggtacgtgg atggcgtgga ggtgcacaat   1260

gctaagacca agccaagaga ggagcagttt aattccacat accgcgtggt gagcgtgctg   1320

accgtgctgc atcaggattg gctgaacggc aaggagtata agtgcaaggt gtccaataag   1380

ggcctgccca gctctatcga gaagacaatc agcaaggcta agggacagcc tagggagcca   1440

caggtgtaca ccctgccccc ttctcaggag gagatgacaa agaaccaggt gtccctgacc   1500

tgtctggtga agggcttcta tccaagcgac atcgctgtgg agtgggagtc taatggccag   1560

cccgagaaca attacaagac cacaccaccc gtgctggact ctgatggctc cttctttctg   1620

tattctaggc tgacagtgga taagtcccgg tggcaggagg gcaacgtgtt tagctgctct   1680

gtgatgcacg aggccctgca caatcattat acccagaagt ccctgagcct gtctctgggc   1740

aag                                                                1743


<210> SEQ ID NO 26
<211> LENGTH: 581
<212> TYPE: PRT
<213> ORGANISM: Artificial Sequence
<220> FEATURE:
<223> OTHER INFORMATION: Amino acid sequence of polypeptide chain H6

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Val Gln Leu Val Gln Ser
    130                 135                 140

Gly Ala Glu Val Lys Lys Pro Gly Ser Ser Val Lys Val Ser Cys Lys
145                 150                 155                 160

Ala Ser Gly Tyr Ser Phe Thr His His Trp Ile His Trp Val Arg Gln
                165                 170                 175

Ala Pro Gly Gln Gly Leu Glu Trp Met Gly Met Ile Asp Ala Ser Asp
            180                 185                 190

Ser Glu Thr Arg Leu Ser Gln Lys Phe Lys Asp Arg Val Thr Ile Thr
        195                 200                 205

Ala Asp Lys Ser Thr Ser Thr Ala Tyr Met Glu Leu Ser Ser Leu Arg
    210                 215                 220

Ser Glu Asp Thr Ala Val Tyr Tyr Cys Ala Arg Leu Gly Arg Tyr Tyr
225                 230                 235                 240
```

```
Phe Asp Tyr Trp Gly Gln Gly Thr Thr Val Thr Val Ser Ser Ala Ser
                245                 250                 255

Thr Lys Gly Pro Ser Val Phe Pro Leu Ala Pro Cys Ser Arg Ser Thr
            260                 265                 270

Ser Glu Ser Thr Ala Ala Leu Gly Cys Leu Val Lys Asp Tyr Phe Pro
        275                 280                 285

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Lys Thr Tyr Thr
                325                 330                 335

Cys Asn Val Asp His Lys Pro Ser Asn Thr Lys Val Asp Lys Arg Val
            340                 345                 350

Glu Ser Lys Tyr Gly Pro Pro Cys Pro Pro Cys Pro Ala Pro Glu Phe
        355                 360                 365

Glu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser Gln Glu Asp Pro Glu Val Gln Phe Asn Trp Tyr Val Asp Gly Val
                405                 410                 415

Glu Val His Asn Ala Lys Thr Lys Pro Arg Glu Glu Gln Phe Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Gly Leu Pro Ser
    450                 455                 460

Ser Ile Glu Lys Thr Ile Ser Lys Ala Lys Gly Gln Pro Arg Glu Pro
465                 470                 475                 480

Gln Val Tyr Thr Leu Pro Pro Ser Gln Glu Glu Met Thr Lys Asn Gln
                485                 490                 495

Val Ser Leu Thr Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
        515                 520                 525

Pro Pro Val Leu Asp Ser Asp Gly Ser Phe Phe Leu Tyr Ser Arg Leu
    530                 535                 540

Thr Val Asp Lys Ser Arg Trp Gln Glu Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Leu Gly Lys
            580
```

<210> SEQ ID NO 27
<211> LENGTH: 1053
<212> TYPE: DNA
<213> ORGANISM: Artificial Sequence
<220> FEATURE:
<223> OTHER INFORMATION: DNA sequence of polypeptide chain L5

<400> SEQUENCE: 27

```
gagatcgtgc tgacccagtc tccagccaca ctgtctctgt ccccaggaga gagggccacc      60
ctgagctgcc gggcttctga gaacgtgggc acatacatct cctggtatca gcagaagcca     120
ggacaggctc ctaggctgct gatctacggc gctagcaata gatataccgg catccctgct     180
cgcttcagcg gatctggatc cggcacagac tttaccctga caatctccag cctggagcca     240
gaggatttcg ccgtgtacta ttgtggcgag tcctacggcc acctgtatac ctttggcggc     300
ggcacaaagg tggagatcaa gcgaacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gtggtggagg cggtagtgga     660
ggcggtggtt caggcggagg cggatctgag gtgcagctgg tggagtccgg aggaggactg     720
gtgcagccag gaggctccct gaggctgagc tgcgccgctt ctggctacac cgtgtccagc     780
tattgtatgg gctggttcag gcaggctcct ggcaagggaa gggagggcgt gtccgctatc     840
gacagcgatg gcagcgtgtc ttacgccgac agcgtgaagg gcagattcac catctctaag     900
gataactcca agaatacact gtacctgcag atgaactctc tgcgcgccga ggacaccgcc     960
gtgtactttt gcgctgctga cctgtgctgg gtggaccagg atcagggcga gtataataca    1020
tggggccagg gcaccctggt gacagtgtct tcc                                 1053
```

<210> SEQ ID NO 28
<211> LENGTH: 351
<212> TYPE: PRT
<213> ORGANISM: Artificial Sequence
<220> FEATURE:
<223> OTHER INFORMATION: Amino acid sequence of polypeptide chain L5

<400> SEQUENCE: 28

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Asn Val Gly Thr Tyr
            20                  25                  30

Ile Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gly Glu Ser Tyr Gly His Leu Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Glu Val Gln Leu Val Glu Ser Gly Gly Gly Leu
225                 230                 235                 240

Val Gln Pro Gly Gly Ser Leu Arg Leu Ser Cys Ala Ala Ser Gly Tyr
                245                 250                 255

Thr Val Ser Ser Tyr Cys Met Gly Trp Phe Arg Gln Ala Pro Gly Lys
            260                 265                 270

Gly Arg Glu Gly Val Ser Ala Ile Asp Ser Asp Gly Ser Val Ser Tyr
        275                 280                 285

Ala Asp Ser Val Lys Gly Arg Phe Thr Ile Ser Lys Asp Asn Ser Lys
    290                 295                 300

Asn Thr Leu Tyr Leu Gln Met Asn Ser Leu Arg Ala Glu Asp Thr Ala
305                 310                 315                 320

Val Tyr Phe Cys Ala Ala Asp Leu Cys Trp Val Asp Gln Asp Gln Gly
                325                 330                 335

Glu Tyr Asn Thr Trp Gly Gln Gly Thr Leu Val Thr Val Ser Ser
            340                 345                 350
```

<210> SEQ ID NO 29
<211> LENGTH: 1053
<212> TYPE: DNA
<213> ORGANISM: Artificial Sequence
<220> FEATURE:
<223> OTHER INFORMATION: DNA sequence of polypeptide chain L6

<400> SEQUENCE: 29

```
gaggtgcagc tggtggagtc cggaggagga ctggtgcagc caggaggctc cctgaggctg     60

agctgcgccg cttctggcta caccgtgtcc agctattgta tgggctggtt caggcaggct    120

cctggcaagg gaagggaggg cgtgtccgct atcgacagcg atggcagcgt gtcttacgcc    180

gacagcgtga agggcagatt caccatctct aaggataact ccaagaatac actgtacctg    240

cagatgaact ctctgcgcgc cgaggacacc gccgtgtact tttgcgctgc tgacctgtgc    300

tgggtggacc aggatcaggg cgagtataat acatggggcc agggcaccct ggtgacagtg    360

tcttccggtg gaggcggtag tggaggcggt ggttcaggcg gaggcggatc tgagatcgtg    420

ctgacccagt ctccagccac actgtctctg tccccaggag agagggccac cctgagctgc    480

cgggcttctg agaacgtggg cacatacatc tcctggtatc agcagaagcc aggacaggct    540

cctaggctgc tgatctacgg cgctagcaat agatataccg gcatccctgc tcgcttcagc    600

ggatctggat ccggcacaga ctttaccctg acaatctcca gcctggagcc agaggatttc    660

gccgtgtact attgtggcga gtcctacggc cacctgtata cctttggcgg cggcacaaag    720

gtggagatca agcgaacggt ggctgcacca tctgtcttca tcttcccgcc atctgatgag    780

cagttgaaat ctggaactgc ctctgttgtg tgcctgctga ataacttcta tcccagagag    840

gccaaagtac agtggaaggt ggataacgcc ctccaatcgg gtaactccca ggagagtgtc    900
```

acagagcagg acagcaagga cagcacctac agcctcagca gcaccctgac gctgagcaaa 960
gcagactacg agaaacacaa agtctacgcc tgcgaagtca cccatcaggg cctgagctcg 1020
cccgtcacaa agagcttcaa caggggagag tgt 1053

<210> SEQ ID NO 30
<211> LENGTH: 351
<212> TYPE: PRT
<213> ORGANISM: Artificial Sequence
<220> FEATURE:
<223> OTHER INFORMATION: Amino acid sequence of polypeptide chain L6

<400> SEQUENCE: 30

Glu Val Gln Leu Val Glu Ser Gly Gly Gly Leu Val Gln Pro Gly Gly
1 5 10 15

Ser Leu Arg Leu Ser Cys Ala Ala Ser Gly Tyr Thr Val Ser Ser Tyr
20 25 30

Cys Met Gly Trp Phe Arg Gln Ala Pro Gly Lys Gly Arg Glu Gly Val
35 40 45

Ser Ala Ile Asp Ser Asp Gly Ser Val Ser Tyr Ala Asp Ser Val Lys
50 55 60

Gly Arg Phe Thr Ile Ser Lys Asp Asn Ser Lys Asn Thr Leu Tyr Leu
65 70 75 80

Gln Met Asn Ser Leu Arg Ala Glu Asp Thr Ala Val Tyr Phe Cys Ala
85 90 95

Ala Asp Leu Cys Trp Val Asp Gln Asp Gln Gly Glu Tyr Asn Thr Trp
100 105 110

Gly Gln Gly Thr Leu Val Thr Val Ser Ser Gly Gly Gly Gly Ser Gly
115 120 125

Gly Gly Gly Ser Gly Gly Gly Gly Ser Glu Ile Val Leu Thr Gln Ser
130 135 140

Pro Ala Thr Leu Ser Leu Ser Pro Gly Glu Arg Ala Thr Leu Ser Cys
145 150 155 160

Arg Ala Ser Glu Asn Val Gly Thr Tyr Ile Ser Trp Tyr Gln Gln Lys
165 170 175

Pro Gly Gln Ala Pro Arg Leu Leu Ile Tyr Gly Ala Ser Asn Arg Tyr
180 185 190

Thr Gly Ile Pro Ala Arg Phe Ser Gly Ser Gly Ser Gly Thr Asp Phe
195 200 205

Thr Leu Thr Ile Ser Ser Leu Glu Pro Glu Asp Phe Ala Val Tyr Tyr
210 215 220

Cys Gly Glu Ser Tyr Gly His Leu Tyr Thr Phe Gly Gly Gly Thr Lys
225 230 235 240

Val Glu Ile Lys Arg Thr Val Ala Ala Pro Ser Val Phe Ile Phe Pro
245 250 255

Pro Ser Asp Glu Gln Leu Lys Ser Gly Thr Ala Ser Val Val Cys Leu
260 265 270

Leu Asn Asn Phe Tyr Pro Arg Glu Ala Lys Val Gln Trp Lys Val Asp
275 280 285

Asn Ala Leu Gln Ser Gly Asn Ser Gln Glu Ser Val Thr Glu Gln Asp
290 295 300

Ser Lys Asp Ser Thr Tyr Ser Leu Ser Ser Thr Leu Thr Leu Ser Lys
305 310 315 320

Ala Asp Tyr Glu Lys His Lys Val Tyr Ala Cys Glu Val Thr His Gln
325 330 335

```
Gly Leu Ser Ser Pro Val Thr Lys Ser Phe Asn Arg Gly Glu Cys
            340                 345                 350


<210> SEQ ID NO 31
<211> LENGTH: 1053
<212> TYPE: DNA
<213> ORGANISM: Artificial Sequence
<220> FEATURE:
<223> OTHER INFORMATION: DNA sequence of polypeptide chain H7

<400> SEQUENCE: 31

gaggtgcagc tggtggagtc cggaggagga ctggtgcagc caggaggctc cctgaggctg     60

agctgcgccg cttctggcta caccgtgtcc agctattgta tgggctggtt caggcaggct    120

cctggcaagg gaagggaggg cgtgtccgct atcgacagcg atggcagcgt gtcttacgcc    180

gacagcgtga agggcagatt caccatctct aaggataact ccaagaatac actgtacctg    240

cagatgaact ctctgcgcgc cgaggacacc gccgtgtact tttgcgctgc tgacctgtgc    300

tgggtggacc aggatcaggg cgagtataat acatggggcc agggcaccct ggtgacagtg    360

tcttccgaga gcaagtacgg accaccttgc ccaccatgtc cagctcctga gtttgaggga    420

ggaccatccg tgttcctgtt tcctccaaag cctaaggaca ccctgatgat cagccggaca    480

cctgaggtga cctgcgtggt ggtggacgtg tctcaggagg atccagaggt gcagttcaac    540

tggtacgtgg atggcgtgga ggtgcacaat gctaagacca agccaagaga ggagcagttt    600

aattccacat accgcgtggt gagcgtgctg accgtgctgc atcaggattg gctgaacggc    660

aaggagtata agtgcaaggt gtccaataag ggcctgccca gctctatcga gaagacaatc    720

agcaaggcta agggacagcc tagggagcca caggtgtaca ccctgccccc ttctcaggag    780

gagatgacaa agaaccaggt gtccctgacc tgtctggtga agggcttcta tccaagcgac    840

atcgctgtgg agtgggagtc taatggccag cccgagaaca attacaagac cacaccaccc    900

gtgctggact ctgatggctc cttctttctg tattctaggc tgacagtgga taagtcccgg    960

tggcaggagg gcaacgtgtt tagctgctct gtgatgcacg aggccctgca caatcattat   1020

acccagaagt ccctgagcct gtctctgggc aag                                1053


<210> SEQ ID NO 32
<211> LENGTH: 351
<212> TYPE: PRT
<213> ORGANISM: Artificial Sequence
<220> FEATURE:
<223> OTHER INFORMATION: Amino acid sequence of polypeptide chain H7

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95
```

```
Ala Asp Leu Cys Trp Val Asp Gln Asp Gln Gly Glu Tyr Asn Thr Trp
            100                 105                 110

Gly Gln Gly Thr Leu Val Thr Val Ser Ser Glu Ser Lys Tyr Gly Pro
        115                 120                 125

Pro Cys Pro Pro Cys Pro Ala Pro Glu Phe Glu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys
            340                 345                 350


<210> SEQ ID NO 33
<211> LENGTH: 10
<212> TYPE: PRT
<213> ORGANISM: Artificial Sequence
<220> FEATURE:
<223> OTHER INFORMATION: Heavy chain CDR1 sequence of anti-CD47 antibody

<400> SEQUENCE: 33

Gly Tyr Ser Phe Thr His His Trp Ile His
1               5                   10


<210> SEQ ID NO 34
<211> LENGTH: 17
<212> TYPE: PRT
<213> ORGANISM: Artificial Sequence
<220> FEATURE:
<223> OTHER INFORMATION: Heavy chain CDR2 sequence of anti-CD47 antibody

<400> SEQUENCE: 34

Met Ile Asp Ala Ser Asp Ser Glu Thr Arg Leu Ser Gln Lys Phe Lys
1               5                   10                  15

Asp


<210> SEQ ID NO 35
```

<211> LENGTH: 8
<212> TYPE: PRT
<213> ORGANISM: Artificial Sequence
<220> FEATURE:
<223> OTHER INFORMATION: Heavy chain CDR3 sequence of anti-CD47 antibody

<400> SEQUENCE: 35

Leu Gly Arg Tyr Tyr Phe Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: Light chain CDR1 sequence of anti-CD47 antibody

<400> SEQUENCE: 36

Arg Ala Ser Glu Asn Val Gly Thr Tyr Ile Ser
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Light chain CDR2 sequence of anti-CD47 antibody

<400> SEQUENCE: 37

Gly Ala Ser Asn Arg Tyr Thr
1               5

<210> SEQ ID NO 38
<211> LENGTH: 9
<212> TYPE: PRT
<213> ORGANISM: Artificial Sequence
<220> FEATURE:
<223> OTHER INFORMATION: Light chain CDR3 sequence of anti-CD47 antibody

<400> SEQUENCE: 38

Gly Glu Ser Tyr Gly His Leu Tyr Thr
1               5

<210> SEQ ID NO 39
<211> LENGTH: 366
<212> TYPE: DNA
<213> ORGANISM: Artificial Sequence
<220> FEATURE:
<223> OTHER INFORMATION: DNA sequence of LAG-3 sdAb

<400> SEQUENCE: 39
gaggtgcagc tggtggagtc cggaggagga ctggtgcagc caggaggctc cctgaggctg      60
agctgcgccg cttctggcta caccgtgtcc agctattgta tgggctggtt caggcaggct     120
cctggcaagg gaagggaggg cgtgtccgct atcgacagcg atggcagcgt gtcttacgcc     180
gacagcgtga agggcagatt caccatctct aaggataact ccaagaatac actgtacctg     240
cagatgaact ctctgcgcgc cgaggacacc gccgtgtact tttgcgctgc tgacctgtgc     300
tgggtggacc aggatcaggg cgagtataat acatggggcc agggcaccct ggtgacagtg     360
tcttcc                                                                366

<210> SEQ ID NO 40
<211> LENGTH: 122
<212> TYPE: PRT
<213> ORGANISM: Artificial Sequence

```
<220> FEATURE:
<223> OTHER INFORMATION: Amino acid sequence of LAG-3 sdAb

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Val Ser Ser Tyr
            20                  25                  30

Cys Met Gly Trp Phe Arg Gln Ala Pro Gly Lys Gly Arg Glu Gly Val
        35                  40                  45

Ser Ala Ile Asp Ser Asp Gly Ser Val Ser Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Ala Asp Leu Cys Trp Val Asp Gln Asp Gln Gly Glu Tyr Asn Thr Trp
            100                 105                 110

Gly Gln Gly Thr Leu Val Thr Val Ser Ser
        115                 120


<210> SEQ ID NO 41
<211> LENGTH: 10
<212> TYPE: PRT
<213> ORGANISM: Artificial Sequence
<220> FEATURE:
<223> OTHER INFORMATION: CDR1 amino acid sequence of LAG-3 sdAb

<400> SEQUENCE: 41

Gly Tyr Thr Val Ser Ser Tyr Cys Met Gly
1               5                   10


<210> SEQ ID NO 42
<211> LENGTH: 16
<212> TYPE: PRT
<213> ORGANISM: Artificial Sequence
<220> FEATURE:
<223> OTHER INFORMATION: CDR2 amino acid sequence of LAG-3 sdAb

<400> SEQUENCE: 42

Ala Ile Asp Ser Asp Gly Ser Val Ser Tyr Ala Asp Ser Val Lys Gly
1               5                   10                  15


<210> SEQ ID NO 43
<211> LENGTH: 14
<212> TYPE: PRT
<213> ORGANISM: Artificial Sequence
<220> FEATURE:
<223> OTHER INFORMATION: CDR3 amino acid sequence of LAG-3 sdAb

<400> SEQUENCE: 43

Asp Leu Cys Trp Val Asp Gln Asp Gln Gly Glu Tyr Asn Thr
1               5                   10


<210> SEQ ID NO 44
<211> LENGTH: 45
<212> TYPE: DNA
<213> ORGANISM: Artificial Sequence
<220> FEATURE:
<223> OTHER INFORMATION: DNA sequence of E-Linker

<400> SEQUENCE: 44

gaacctaagt ctagcgacaa aactcatacc agcccccta gtcca                     45
```

<210> SEQ ID NO 45
<211> LENGTH: 15
<212> TYPE: PRT
<213> ORGANISM: Artificial Sequence
<220> FEATURE:
<223> OTHER INFORMATION: Amino acid sequence of E-Linker

<400> SEQUENCE: 45

Glu Pro Lys Ser Ser Asp Lys Thr His Thr Ser Pro Pro Ser Pro
1               5                   10                  15

<210> SEQ ID NO 46
<211> LENGTH: 45
<212> TYPE: DNA
<213> ORGANISM: Artificial Sequence
<220> FEATURE:
<223> OTHER INFORMATION: DNA sequence of G15-Linker

<400> SEQUENCE: 46
ggtggaggcg gtagtggagg cggtggttca ggcggaggcg gatct 45

<210> SEQ ID NO 47
<211> LENGTH: 15
<212> TYPE: PRT
<213> ORGANISM: Artificial Sequence
<220> FEATURE:
<223> OTHER INFORMATION: Amino acid sequence of G15-Linker

<400> SEQUENCE: 47

Gly Gly Gly Gly Ser Gly Gly Gly Gly Ser Gly Gly Gly Gly Ser
1               5                   10                  15

<210> SEQ ID NO 48
<211> LENGTH: 27
<212> TYPE: DNA
<213> ORGANISM: Artificial Sequence
<220> FEATURE:
<223> OTHER INFORMATION: DNA sequence of G9-Linker

<400> SEQUENCE: 48
ggtggaggcg gtagtggagg cggttca 27

<210> SEQ ID NO 49
<211> LENGTH: 9
<212> TYPE: PRT
<213> ORGANISM: Artificial Sequence
<220> FEATURE:
<223> OTHER INFORMATION: Amino acid sequence of G9-Linker

<400> SEQUENCE: 49

Gly Gly Gly Gly Ser Gly Gly Gly Ser
1               5

<210> SEQ ID NO 50
<211> LENGTH: 687
<212> TYPE: DNA
<213> ORGANISM: Artificial Sequence
<220> FEATURE:
<223> OTHER INFORMATION: DNA sequence of IgG4 Fc

<400> SEQUENCE: 50
gagagcaagt acggaccacc ttgcccacca tgtccagctc ctgagtttga gggaggacca 60
tccgtgttcc tgtttcctcc aaagcctaag gacaccctga tgatcagccg gacacctgag 120
gtgacctgcg tggtggtgga cgtgtctcag gaggatccag aggtgcagtt caactggtac 180

-continued gtggatggcg tggaggtgca caatgctaag accaagccaa gagaggagca gtttaattcc 240
acataccgcg tggtgagcgt gctgaccgtg ctgcatcagg attggctgaa cggcaaggag 300
tataagtgca aggtgtccaa taagggcctg cccagctcta tcgagaagac aatcagcaag 360
gctaagggac agcctaggga gccacaggtg tacaccctgc cccttctca ggaggagatg 420 acaaagaacc aggtgtccct gacctgtctg gtgaagggct tctatccaag cgacatcgct 480
gtggagtggg agtctaatgg ccagcccgag aacaattaca agaccacacc acccgtgctg 540
gactctgatg gctccttctt tctgtattct aggctgacag tggataagtc ccggtggcag 600
gagggcaacg tgtttagctg ctctgtgatg cacgaggccc tgcacaatca ttatacccag 660
aagtccctga gcctgtctct gggcaag 687

<210> SEQ ID NO 51
<211> LENGTH: 229
<212> TYPE: PRT
<213> ORGANISM: Artificial Sequence
<220> FEATURE:
<223> OTHER INFORMATION: Amino acid sequence of IgG4 Fc

<400> SEQUENCE: 51

Glu Ser Lys Tyr Gly Pro Pro Cys Pro Pro Cys Pro Ala Pro Glu Phe
1 5 10 15

Glu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225